United States Patent
Wilson et al.

(10) Patent No.: US 11,420,998 B2
(45) Date of Patent: *Aug. 23, 2022

(54) AROMATIC-CATIONIC PEPTIDES AND METHODS FOR USING SAME

(71) Applicants: Stealth Biotherapeutics Inc., Needham, MA (US); Mayo Foundation for Medical Education and Research, Rochester, MN (US)

(72) Inventors: D. Travis Wilson, Newton, MA (US); Lilach O. Lerman, Rochester, MN (US); Stephen C. Textor, Rochester, MN (US)

(73) Assignees: Stealth Biotherapeutics Inc., Needham, MA (US); Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/724,037

(22) Filed: Dec. 20, 2019

(65) Prior Publication Data

US 2020/0223887 A1 Jul. 16, 2020

Related U.S. Application Data

(60) Division of application No. 15/840,700, filed on Dec. 13, 2017, now abandoned, which is a continuation of application No. 14/347,998, filed as application No. PCT/US2012/058091 on Sep. 28, 2012, now Pat. No. 9,988,422.

(60) Provisional application No. 61/681,444, filed on Aug. 9, 2012, provisional application No. 61/642,282, filed on May 3, 2012, provisional application No. 61/596,455, filed on Feb. 8, 2012, provisional application No. 61/558,177, filed on Nov. 10, 2011, provisional application No. 61/540,910, filed on Sep. 29, 2011.

(51) Int. Cl.
| | |
|---|---|
| C07K 5/09 | (2006.01) |
| A61K 38/07 | (2006.01) |
| A61K 38/06 | (2006.01) |
| A61K 45/06 | (2006.01) |

(52) U.S. Cl.
CPC ............ *C07K 5/0817* (2013.01); *A61K 38/06* (2013.01); *A61K 38/07* (2013.01); *A61K 45/06* (2013.01)

(58) Field of Classification Search
CPC .................................. C07K 5/10; A61K 38/07
See application file for complete search history.

(56) References Cited

U.S. PATENT DOCUMENTS

| | | | |
|---|---|---|---|
| 4,522,811 A | 6/1985 | Eppstein et al. | |
| 5,573,957 A | 11/1996 | Cardone et al. | |
| 5,674,534 A | 10/1997 | Zale et al. | |
| 5,716,644 A | 2/1998 | Zale et al. | |
| 6,468,798 B1 | 10/2002 | Debs et al. | |
| 6,653,336 B1 | 11/2003 | Guez et al. | |
| 7,576,061 B2 | 8/2009 | Szeto et al. | |
| 7,718,620 B2 | 5/2010 | Szeto et al. | |
| 9,988,422 B2* | 6/2018 | Wilson | A61K 45/06 |
| 2007/0293552 A1 | 12/2007 | Gorczynski | |
| 2009/0221514 A1* | 9/2009 | Szeto | A61P 13/12 514/1.1 |
| 2010/0184708 A1 | 7/2010 | Bevec | |
| 2010/0305183 A1 | 12/2010 | Nimmo et al. | |
| 2011/0082324 A1 | 4/2011 | Wellenhofer et al. | |
| 2011/0082328 A1 | 4/2011 | Gozzi et al. | |
| 2012/0329730 A1 | 12/2012 | Szeto et al. | |
| 2014/0294796 A1 | 10/2014 | Wilson et al. | |
| 2017/0218016 A1 | 8/2017 | Wilson | |

FOREIGN PATENT DOCUMENTS

| | | |
|---|---|---|
| CN | 1787831 A | 6/2006 |
| EP | 0 278 787 | 8/1988 |
| EP | 0 350 221 B1 | 10/1990 |
| JP | 01-502158 | 8/1989 |
| JP | 2002-535358 A | 10/2002 |
| JP | 2006-516652 A | 7/2006 |
| JP | 2007-503461 A | 2/2007 |
| JP | 2007-518818 A | 7/2007 |
| JP | 2007-537160 A | 12/2007 |
| JP | 2009-504570 A | 2/2009 |
| JP | 2011-513241 A | 4/2011 |
| WO | WO-88/06187 A1 | 8/1988 |
| WO | WO-96/40073 A2 | 12/1996 |

(Continued)

OTHER PUBLICATIONS

Endothelix, "About Vascular Function/Reactivity", https://www.endothelix.com/patients/about-vascular-function-reactivity/; accessed on Apr. 2, 202 (Year: 2021).*
Carroll et al. "Renal System and Urinary Tract" Elsevier's Integrated Physiology, 2007, pp. 117-137 (Year: 2007).*
Main "Atherosclerotic Renal Artery Stenosis, ACE Inhibitors, and Avoiding Cardiovascular Death", Heart 2005;91:548-552 (Year: 2005).*

(Continued)

*Primary Examiner* — Lianko G Garyu
(74) *Attorney, Agent, or Firm* — Foley & Lardner LLP

(57) ABSTRACT

The present disclosure provides methods of preventing or treating renal ischemia-reperfusion injury in a mammalian subject and methods for chronic treatment of ARVD, including administering an effective amount of an aromatic-cationic peptide to a subject in need thereof. The methods include administering aromatic-cationic peptides to prevent or treat renal injury during the treatment of renal artery stenosis. The methods include administering an effective amount of an aromatic-cationic peptide to subjects in need thereof.

11 Claims, 18 Drawing Sheets

(56) References Cited

FOREIGN PATENT DOCUMENTS

| WO | WO-99/15154 A1 | 4/1999 |
|---|---|---|
| WO | WO-00/38651 A1 | 7/2000 |
| WO | WO-00/44365 A1 | 8/2000 |
| WO | WO-2004/070054 A2 | 8/2004 |
| WO | WO-2005/001023 | 1/2005 |
| WO | WO-2004/070054 A3 | 4/2005 |
| WO | WO-2005/072295 A2 | 8/2005 |
| WO | WO-2005/097172 | 10/2005 |
| WO | WO-2007/012947 | 2/2007 |
| WO | WO-2009/108695 A2 | 9/2009 |
| WO | WO-2009/123486 | 10/2009 |
| WO | WO-2009/123487 A1 | 10/2009 |
| WO | WO-2010/120431 A2 | 10/2010 |
| WO | WO-2011/082324 A1 | 7/2011 |
| WO | WO-2011/082328 A1 | 7/2011 |
| WO | WO-2011/116007 A1 | 9/2011 |

OTHER PUBLICATIONS

Amselem, S., et al., "A Large Scale Method for the Preparation of Sterile and Non-Pyrogenic Liposomal Formulations of Defined Size Distributions for Clinical Use", (1993) In: Liposome Technology: Entrapment of Drugs and Other Materials, vol. 1, 2nd Edition, Ed. Gregory Gregoriadis, Chapter 28, pp. 501-526 (26 pages).

Bakker, Erik N.T.P. et al., "Small Artery Remodeling Depends on Tissue-Type Transglutaminase," Circulation Research (Jan. 2005), vol. 96, Issue 1, pp. 119-126.

Balk, Ethan et al., "Effectiveness of Management Strategies for Renal Artery Stenosis: A Systematic Review," Annals of Internal Medicine, (Dec. 19), 2006, vol. 145, No. 12, pp. 901-912 and W248-W249.

Carmichael, Paul et al., "Atherosclerotic renal artery stenosis: from diagnosis to treatment," Postgrad Med J, (1999), vol. 75, pp. 527-536.

Chade, Alejandro R. et al., "Antioxidant Intervention Blunts Renal Injury in Experimental Renovascular Disease," J Am Soc Nephrol, (2004), vol. 15, No. 4, pp. 958-966.

Chade, Alejandro R. et al., "Antioxidant Intervention Prevents Renal Neovascularization in Hypercholesterolemic Pigs," J Am Soc Nephrol, (2004), vol. 15, No. 7, pp. 1816-1825.

Chade, Alejandro R. et al., "Beneficial Effects of Antioxidant Vitamins on the Stenotic Kidney," Hypertension, (Oct. 2003), vol. 42, No. 4, pp. 605-612.

Chade, Alejandro R. et al., "Comparison of acute and chronic antioxidant interventions in experimental renovascular disease," Am J Physiol Renal Physiol, (2004), vol. 286, pp. F1079-F1086.

Chade, Alejandro R. et al., "Distinct Renal Injury in Early Atherosclerosis and Renovascular Disease," Circulation, (Aug. 27, 2002), vol. 106, No. 9, pp. 1165-1171.

Chade, Alejandro R. et al., "Endothelin-1 receptor blockade prevents renal injury in experimental hypercholesterolemia," Kidney Int, (Sep. 2003), vol. 64, No. 3, pp. 962-969.

Chade, Alejandro R. et al., "Mechanisms of Renal Structural Alterations in Combined Hypercholesterolemia and Renal Artery Stenosis," Arterioscler Thromb Vasc Biol, (Jul. 2003), vol. 23, No. 7, pp. 1295-1301.

Chade, Alejandro R et al., "Renal Microvascular Disease Determines the Responses to Revascularization in Experimental Renovascular Disease," Circ Cardiovasc Interv, (2010), vol. 3, Issue 4, pp. 376-383.

Chade, Alejandro R. et al., "Simvastatin promotes angiogenesis and prevents microvascular remodeling in chronic renal ischemia," FASEB Journal, (Jun. 21, 2006), vol. 20, No. 10, pp. 1706-1708.

Cheng, Feng-Ying et al., "Mitochondria-Targeted Antioxidant Peptide Promotes ATP Recovery and Reduces Renal Ischemia-Reperfusion Injury", The Faseb Journal, Federation of American Societies for Experimental Biology, US, (Apr. 1, 2010), vol. 24, Abstract only (2 pp.).

Cho, Sunghee et al., "$201CA Novel Cell-permeable Antioxidant Peptide, SS31, Attenuates Ischemic Brain Injury by Down-regulating CD36,$201D J. Biol. Chem., (Feb. 2007), vol. 282, No. 7, pp. 4634-4642.

Chonn et al. "Recent Advances in Liposomal Drug-Delivery Systems," Curr. Opin. Biotechnol., (1995), vol. 6, Issue 6, pp. 698-708.

Daemen, Marc A.R.C. et al., "Inhibition of apoptosis induced by ischemia-reperfusion prevents inflammation," J Clin Invest, (Sep. 1999), vol. 104, No. 5, pp. 541-549.

Dai, Dao-Fu et al., "Mitochondrial targeted antioxidant peptide ameliorates hypertensive cardiomyopathy," J. Am. Coll. Cardiol., (2011), vol. 58, No. 1, pp. 73-82.

Epstein, Franklin H. et al., "Effect of Diabetes on Renal Medullary Oxygenation During Water Diuresis," Diabetes Care, (Mar. 2002), vol. 25, No. 3, pp. 575-578.

Epstein, Franklin H. et al., "Effects of furosemide on medullary oxygenation in younger and older subjects," Kidney Int., (May 2000), vol. 57, No. 5, pp. 2080-2083.

Favreau, Frederic et al., "Revascularization of swine renal artery stenosis improves renal function but not the changes in vascular structure," Kidney Int., (Dec. 2010), vol. 78, No. 11, pp. 1110-1118.

Gerwins, Par et al., "Function of fibroblast growth factors and vascular endothelial growth factors and their receptors in angiogenesis," Crit Rev Oncol Hematol., (Jun. 2000), vol. 34, Issue 3, pp. 185-194.

Gloviczki, Monika L. et al., "Comparison of 1.5 and 3 T BOLD MR to Study Oxygenation of Kidney Cortex and Medulla in Human Renovascular Disease," (Sep. 2009), vol. 44, Issue 9, pp. 566-572.

Gloviczki, Monika L. et al., "Preserved Oxygenation Despite Reduced Blood Flow in Poststenotic Kidneys in Human Atherosclerotic Renal Artery Stenosis," Hypertension, (Apr. 2010), vol. 55, pp. 961-966.

Gomez, Ludovic et al., "Inhibition of mitochondrial permeability transition pore opening: translation to patients," Cardiovascular Research, (Feb. 2009), 83, pp. 226-233.

Gomez, Sabas I. et al., "Increased hypoxia and reduced renal tubular response to furosemide detected by BOLD magnetic resonance imaging in swine renovascular hypertension," Am J Physiol Renal Physiol, (Oct. 2009), vol. 297, Issue 4, pp. F981-F986.

Gregoriadis, "Engineering Liposomes for Drug Delivery: Progress and Problems," Trends in Biotechnology, (Dec. 1995), vol. 13, No. 12, pp. 527-537.

Hansen, Kimberley J. et al., "Prevalence of renovascular disease in the elderly: A population-based study," J Vasc Surg, (Oct. 2002), vol. 36, Issue 3, pp. 443-451.

Heil, Matthias et al., "Influence of Mechanical, Cellular, and Molecular Factors on Collateral Artery Growth (Arteriogenesis)," Circulation Research, (Sep. 3, 2004), vol. 95, No. 5, pp. 449-458.

Hricik, Donald E. et al., "Captopril-Induced Functional Renal Insufficiency in Patients with Bilateral Renal-Artery Stenoses or Renal-Artery Stenosis in a Solitary Kidney," N Engl J Med, (1983), vol. 308, pp. 373-376.

Iliescu, Radu et al, "Role of renal microcirculation in experimental renovascular disease", Nephrology Dialysis Transplantation, (Nov. 2009), vol. 25, No. 4, pp. 1079-1087.

International Search Report and Written Opinion on Application No. PCT/US2011/034846, dated Jul. 12, 2011, 14 pages.

International Search Report and Written Opinion on Application No. PCT/US2012/058091, dated Dec. 4, 2012, 35 pages.

Juillard, Laurent et al., "Blood oxygen level-dependent measurement of acute intra-renal ischemia," Kidney Int., (Mar. 2004), vol. 65, No. 3, pp. 944-950.

Kalra, Philip A. et al., "Atherosclerotic renovascular disease in United States patients aged 67 years or older: Risk factors, revascularization, and prognosis," Kidney Int., (Jul. 2005), vol. 68, No. 1, pp. 293-301.

Langille, B.L. et al., "Cross-linking vasomotor tone and vascular remodeling: A novel function for tissue transglutaminase?" Circ Res, (Jan. 2005), vol. 96, No. 1, pp. 9-11.

Lavi, Ronit et al., "Simvastatin Decreases Endothelial Progenitor Cell Apoptosis in the Kidney of Hypertensive Hypercholesterolemic Pigs," Arterioscler Thromb Vasc Biol, (May 2010), vol. 30, No. 5, pp. 976-983.

(56) References Cited

OTHER PUBLICATIONS

Lerman, Lilach O. et al., "Noninvasive Evaluation of a Novel Swine Model of Renal Artery Stenosis," J Am Soc Nephrol, (Jul. 1, 1999), vol. 10, No. 7, pp. 1455-1465.
Lichtenberg et al. "Liposomes: Preparation, Characterization, and Preservation," Methods Biochem. Anal., (1998), vol. 33, pp. 337-462.
Lim, Kelvin H.H. et al., "The effects of ischaemic preconditioning, diazoxide and 5-hydroxydecanoate on rat heart mitochondrial volume and respiration," J Physiol, (2002), vol. 545, Issue 3, pp. 961-974.
Liu, Shaoyi et al., "Boosting mitochondrial function to minimize ischemia-reperfusion (IR) injury", The Faseb Journal, Federation of American Societies for Experimental Biology, US, (Apr. 2011) vol. 25, Abstract only (2 pp.).
Mizuguchi, H., et al., "Intratumor adminstration of fusogenic liposomes containing fragment A of diphtheria toxin suppresses tumor growth," Cancer Letters, (1996), vol. 100, No. 1-2, pp. 63-69.
Mizuguchi, Yasunori et al., "A novel cell-permeable antioxidant peptide decreases renal tubular apoptosis and damage in unilateral ureteral obstruction," Am. J. Physiol. Renal Physiol., (2008), 295, pp. F1545-F1553.
Nogae, Shoji et al., "Induction of Apoptosis in Ischemia-Reperfusion Model of Mouse Kidney: Possible Involvement of Fas," (Apr. 1998), vol. 9, No. 4, pp. 620-631.
Orrenius, Sten, "Reactive Oxygen Species in Mitochondria-Mediated Ceil Death," Drug Metab Rev, (2007), vol. 39, No. 2-3, pp. 443-455.
Plouin, Pierre-Francois et al., "Blood Pressure Outcome of Angioplasty in Atherosclerotic Renal Artery Stenosis: A Randomized Trial," Hypertension, (Mar. 1998), vol. 31, No. 3, pp. 823-829.
Prasad, Pottumarthi V. et al., "Changes in renal medullary pO2 during water diuresis as evaluated by blood oxygenation level-dependent magnetic resonance imaging: Effects of aging and cyclooxygenase inhibition," Kidney Int., (Jan. 1999), vol. 55, No. 1, pp. 294-298.
Prasad, Pottumarthi V. et al., "Noninvasive Evaluation of Intrarenal Oxygenation with BOLD MRI," Circulation, (Dec. 15, 1996), No. 94, No. 12, pp. 3271-3275.
Reddy, "Controlled-Release, Pegylation, Liposomal Formulations: New Mechanisms in the Delivery of Injectable Drugs," Ann Pharmacother., (Jul./Aug. 2000), vol. 34, pp. 915-923.
Rosenberger, Christian et al., "Up-regulation of HIF in experimental acute renal failure: Evidence for a protective transcriptional response to hypoxia," Kidney Int., (Feb. 2005), vol. 67, No. 2, pp. 531-542.
Sachse, Anja et al., "Angiotensin II-Induced Reactive Oxygen Species and the Kidney," J Am Soc Nephrol, (Sep. 2007), vol. 18, No. 9, pp. 2439-2446.
Schechter et al., Inhibitors Can Activate Proteases to Catalyze the Synthesis and Hydrolysis of Peptides, Biochemistry, dated Nov. 14, 2006, pp. 14567-14572, vol. 45, No. 49, Accelerated Publications, US.
Schiller, Peter W. et al., "Synthesis and In Vitro Opioid Activity Profiles of DALDA Analogues," European Journal of Medicinal Chemistry, (Oct. 2000), vol. 35, Issue 10, pp. 895-901.
Shanley, Paul F., "The pathology of chronic renal ischemia," Semin Nephrol, (Jan. 1996), vol. 16, No. 1, pp. 21-32.
Stulak, John M. et al., "Renal Vascular Function in Hypercholesterolemia is Preserved by Chronic Antioxidant Supplementation," J Am Soc Nephrol, (Sep. 2001), vol. 12, No. 9, pp. 1882-1891.
Suzuki, Kenji et al., "Studies on Analgesic Oligopeotides, IV, Synthesis and Analgesic Activity of N-Terminal Shorter Analogs of [D-Arg2]Dermorphin and Des-Tyr1-Dermorphin Analogs," Chem. Pharm. Bull., (1985), vol. 33(11), pp. 4865-4869.
Szeto et al., "Mitochondria-Targeted Peptide Accelerates ATP Recovery and Reduces Ischemic Kidney Injury," Journal of the American Society of Nephrol, vol. 22, No. 6, Jun. 1, 2011, pp. 1041-1052.
Szeto, Hazel H. "Mitochondria-targeted peptide antioxidants: Novel Neuroprotective Agents," The AAPS Journal, (2006), 8(3), Article 62, pp. E521-E531.
Szeto, Hazel H. et al., "Mitochondria-Targeted Peptide Accelerates ATP Recovery and Reduces Ischemic Kidney Injury," J. Am. Soc. Nephrol., (2011), 22, pp. 1041-1052.
Szeto, Hazel H., "Mitochondria-Targeted Peptide Antioxidants: Novel Neuroprotective Agents," The AAPS Journal, (2006), vol. 8, No. 3, Article 62, pp. E521-E531.
Szeto, Hazel H., "Mitochondria-targeted Cytoprotective Peptides for Ischemia-Reperfusion Injury," Antioxid. Redox Signal, (2008), vol. 10, No. 3, pp. 601-619.
Textor, Stephen C. et al., "Renal Artery Stenosis: A Common, Treatable Cause of Renal Failure?," (Feb. 2001), vol. 52, pp. 421-442.
The Merck Manual, 18th Edition, Japanese Edition, 2006, p. 2102-2108, 2156-2158, 8 pages.
Urbieta-Caceres, Victor H. et al., "Early atherosclerosis aggravates the effect of renal artery stenosis on the swine kidney," Am J Physiol Renal Physiol, (2010), vol. 299, pp. F135-F140.
Van Jaarsveld, BC et al., "The effect of balloon angioplasty on hypertension in atherosclerotic renal-artery stenosis," Dutch Renal Artery Stenosis Intervention Cooperative Study Group, N Engl J Med, (2000), 342, pp. 1007-1014.
Vedder, N.B. et al., "Inhibition of leukocyte adherence by anti-CD 18 monoclonal antibody attenuates reperfusion injury in the rabbit ear," Proc. Natl. Acad. Sci. USA, (Apr. 1990), vol. 87, No. 7, pp. 2643-2646.
Verhoeff, Bart-Jan et al., "Influence of Percutaneous Coronary Intervention on Coronary Microvascular Resistance Index," Circulation, (Jan. 4, 2005), vol. 111, No. 1, pp. 76-82.
Webster, J. et al., "Randomised comparison of percutaneous angioplasty vs continued medical therapy for hypertensive patients with atheromatous renal artery stenosis," J. Hum. Hypertens, (May 1998), vol. 12, No. 5, pp. 329-335.
Weiner, Alan L., "Liposomes for Protein Delivery: Selecting Manufacture and Development Processes," Immunomethods, (1994), 4(3), pp. 201-209.
Wheatley, Keith et al., "Revascularization versus Medical Therapy for Renal-Artery Stenosis," N Engl J Med, (Nov. 2009), vol. 361, pp. 1953-1962.
Yao, En-Hui et al., "Oxidative Stress on Progenitor and Stem Cells in Cardiovascular Diseases," Curr Pharm Biotechnol, (2006), vol. 7, Issue 2, pp. 101-108.
Zhao, Guo-Min et al., "Comparison of [Dmt1]DALDA and DAMGO in Binding and G Protein Activation at μ, δ, and κ Opioid Receptors," J. Parmacology and Experimental Therapeutics, (2003), vol. 307, No. 3, pp. 947-954.
Zhao, Kesheng et al., "Transcellular Transport of a Highly Polar 3+ Net Charge Opioid Tetrapeptide," Journal of Pharmacology and Experimental Therapeutics, (2003), vol. 304, No. 1, pp. 425-432.
Zhu, Xiang-Yang et al., "Antioxidant Intervention Attenuates Myocardial Neovascularization in Hypercholesterolemia," Circulation, (May 4, 2004), vol. 109, No. 17, pp. 2109-2115.
Zhu, Xiang-Yang et al., "Cortical Microvascular Remodeling in the Stenotic Kidney: Role of Increased Oxidative Stress," Arterioscler Thromb Vase Biol, (Oct. 2004), vol. 24, No. 10, pp. 1854-1859.
Zhu, Xiang-Yang et al., "Redox-sensitive myocardial remodeling and dysfunction in swine diet-induced experimental hypercholesterolemia," Atherosclerosis, (Jul. 2007), vol. 193, Issue 1, pp. 62-69.
Zhu, Xiang-Yang et al., "Simvastatin Prevents Coronary Microvascular Remodeling in Renovascular Hypertensive Pigs," J Am Soc Nephrol, (Apr. 2007), vol. 18, No. 4, pp. 1209-1217.
Zhu, Xiang-Yang et al., "The chemokine monocyte chemoattractant protein-1 contributes to renal dysfunction in swine renovascular hypertension," J Hypertension, (Oct. 2009), vol. 27, Issue 10, pp. 2063-2073.
Eirin et al., "MTP-131 Reduces Renal injury after percutaneous Transluminal Renal Angioplasty (PTRA) in Swine Atherosclerotic renal Artery Stenosis (ARAS)," Abstract TH-P0737, J. Am Sco. Nephrol., (2011).
Hackman et al., "Role of Renin-Angiotensin System Blockade in Atherosclerotic Renal Artery Stenosis and Renovascular Hypertension," Hypertension, pp. 998-1003 (2007).
Decision of Rejection in CN Patent Application No. 201710610548.1 dated Mar. 29, 2021 (with English Translation) (11 pages).

(56) References Cited

OTHER PUBLICATIONS

Eirin et al., "MTP-131 Reduces Renal Injury after Percutaneous Transluminal Renal Angioplasty (PTRA) in Swine Atherosclerotic Renal Artery Stenosis (ARAS)", Abstract TH-PO737, J Am Seo Nephrol; 2011 (Year: 2011).

Hackman et al., "Role of Renin-Angiotensin System Blockade in Atherosclerotic Renal Artery Stenosis and Renovascular Hypertension", Hypertension, 2007, pp. 998-1003 (Year: 2007).

Non-Final Office Action on U.S. Appl. No. 16/903,566 dated May 20, 2022 (10 pages).

\* cited by examiner

FIG. 8A
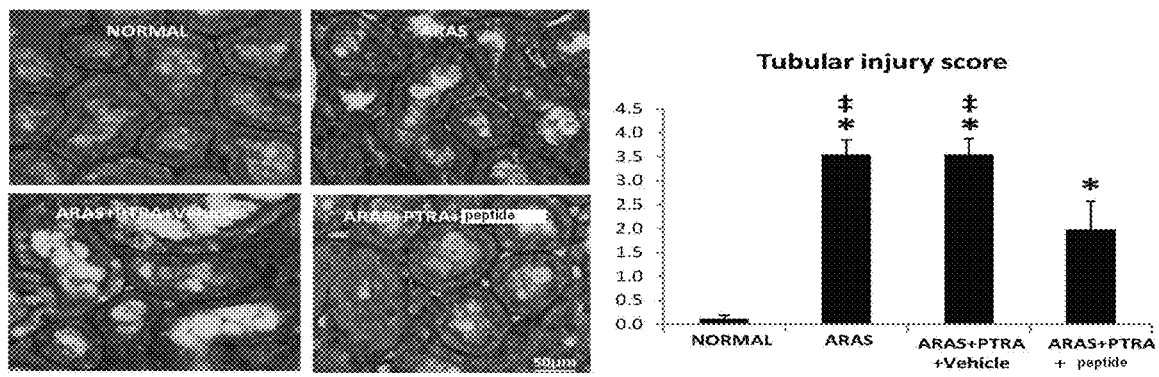
FIG. 8B
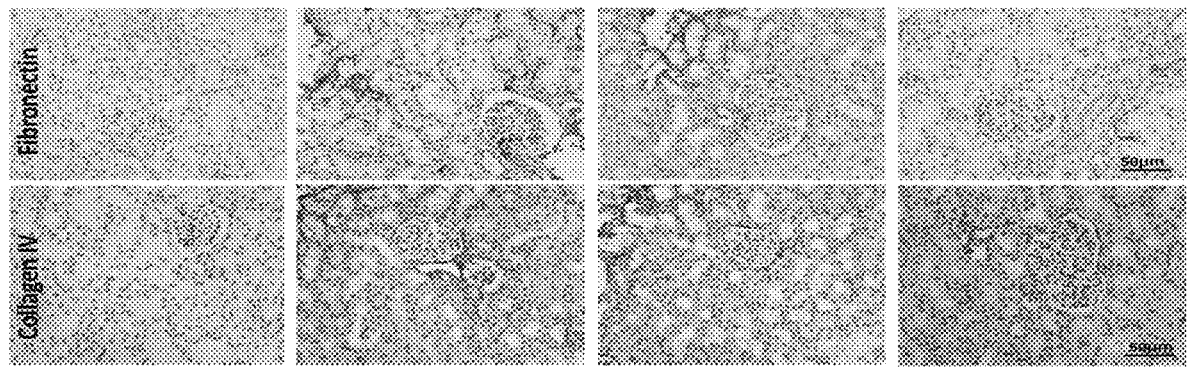
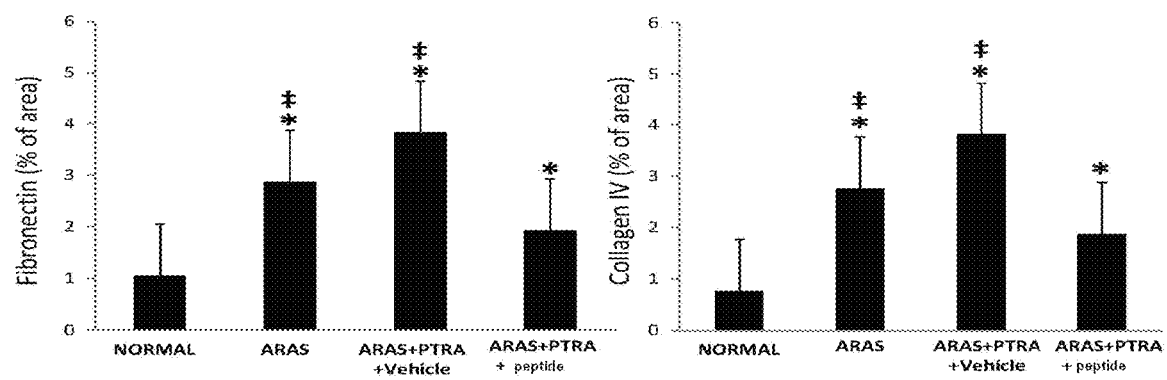
FIG. 8C

AROMATIC-CATIONIC PEPTIDES AND METHODS FOR USING SAME

CROSS-REFERENCE TO RELATED APPLICATIONS

This application claims the benefit of and priority to U.S. Provisional Application No. 61/540,910 filed Sep. 29, 2011, U.S. Provisional Application No. 61/596,455 filed Feb. 8, 2012, U.S. Provisional Application No. 61/558,177, filed Nov. 10, 2011, U.S. Provisional Application No. 61/642,282 filed May 3, 2012, and U.S. Provisional Application No. 61/681,444 filed Aug. 9, 2012, all of which are incorporated herein by reference in their entirety.

TECHNICAL FIELD

The present technology relates generally to compositions and methods of preventing or treating renal ischemia/reperfusion tissue injury. In particular, embodiments of the present technology relate to administering aromatic-cationic peptides in effective amounts to prevent or treat ischemia/reperfusion injury associated with restoration of renal artery patency in the treatment of renal artery stenosis and for chronic treatment of atherosclerotic renovascular disease (ARVD).

BACKGROUND

The following description is provided to assist the understanding of the reader. None of the information provided or references cited is admitted to be prior art.

Renal artery stenosis (RAS), most commonly caused by atherosclerosis, has an incidence of almost 7% in adults older than 65 years of age. Patients with atherosclerotic RAS or (ARVD) often develop hypertension or renovascular hypertension, which significantly increases the risk for coronary artery disease, stroke, peripheral vascular disease, and progression to end stage renal disease. Furthermore, a decrease in renal function per se is associated with increased cardiovascular morbidity and mortality.

In treating atherosclerotic renal artery stenosis (ARAS), the immediate therapeutic goal is to restore patency to the renal artery. Often, percutaneous transluminal renal angioplasty (PTRA) is the recommended course of treatment. However, the successful restoration of renal artery patency does not necessarily translate into restoration of tissue perfusion. Rarefaction of renal microvasculature and reperfusion injury can cause reduced renal perfusion and long-term renal insufficiency. Methods that reduce these effects will improve the long-term prognosis for patients undergoing PTRA therapy and patients with ARVD.

SUMMARY

The present technology relates to the treatment or prevention of renal ischemia-reperfusion injury and ARVD in mammals through administration of therapeutically effective amounts of aromatic-cationic peptides, such as D-Arg-2',6'-Dmt-Lys-Phe-NH$_2$, or pharmaceutically acceptable salts thereof, such as acetate salt or trifluoroacetate salt, to subjects in need thereof. In some embodiments, the present technology relates to methods useful in the treatment or prevention of a renal microvasculature rarefaction. In some aspects, the present technology relates to chronic treatment of subjects with ARVD with therapeutically effective amounts of aromatic-cationic peptides, such as D-Arg-2',6'-Dmt-Lys-Phe-NH$_2$, or pharmaceutically acceptable salts thereof, such as acetate salt or trifluoroacetate salt, to subjects in need thereof.

In some aspects, the disclosure provides a method of treating or preventing renal ischemia/reperfusion injury, renal microvasculature rarefaction, and/or chronic treatment of atherosclerotic renovascular disease (ARVD) comprising administering to a subject in need thereof a therapeutically effective amount of an aromatic-cationic peptide or a pharmaceutically acceptable salt thereof, e.g, D-Arg-2',6'-Dmt-Lys-Phe-NH$_2$, or pharmaceutically acceptable salts thereof, such as acetate salt or trifluoroacetate salt. In some embodiments, the method further comprises performing a revascularization procedure on the subject. In some embodiments, the aromatic-cationic peptide is a peptide having:

at least one net positive charge;
a minimum of four amino acids;
a maximum of about twenty amino acids;
a relationship between the minimum number of net positive charges ($p_m$) and the total number of amino acid residues (r) wherein $3p_m$ is the largest number that is less than or equal to r+1; and a relationship between the minimum number of aromatic groups (a) and the total number of net positive charges ($p_t$) wherein 2a is the largest number that is less than or equal to $p_t$+1, except that when a is 1, $p_t$ may also be 1. In particular embodiments, the subject is a human.

In some embodiments, $2p_m$ is the largest number that is less than or equal to r+1, and a may be equal to $p_t$. The aromatic-cationic peptide may be a water-soluble peptide having a minimum of two or a minimum of three positive charges. In some embodiments, the peptide comprises one or more non-naturally occurring amino acids, for example, one or more D-amino acids. In some embodiments, the C-terminal carboxyl group of the amino acid at the C-terminus is amidated. In certain embodiments, the peptide has a minimum of four amino acids. The peptide may have a maximum of about 6, a maximum of about 9, or a maximum of about 12 amino acids.

In some embodiments, the peptide comprises a tyrosine or a 2',6'-dimethyltyrosine (Dmt) residue at the N-terminus. For example, the peptide may have the formula Tyr-D-Arg-Phe-Lys-NH$_2$ or 2',6'-Dmt-D-Arg-Phe-Lys-NH$_2$. In another embodiment, the peptide comprises a phenylalanine or a 2',6'-dimethylphenylalanine residue at the N-terminus. For example, the peptide may have the formula Phe-D-Arg-Phe-Lys-NH$_2$ or 2',6'-Dmp-D-Arg-Phe-Lys-NH$_2$. In a particular embodiment, the aromatic-cationic peptide has the formula D-Arg-2',6'-Dmt-Lys-Phe-NH$_2$ or a pharmaceutically acceptable salt thereof such as acetate salt or trifluoroacetate salt.

In one embodiment, the peptide is defined by formula I:

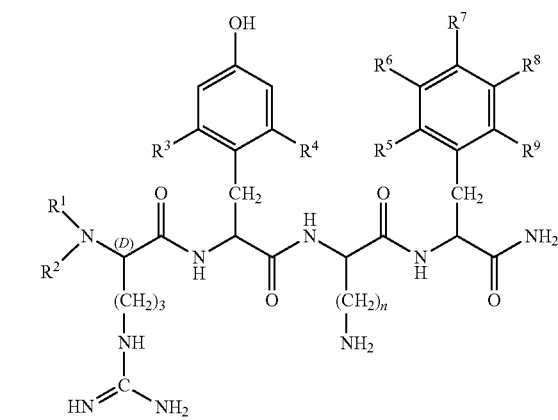

wherein $R^1$ and $R^2$ are each independently selected from
(i) hydrogen;
(ii) linear or branched $C_1$-$C_6$ alkyl;

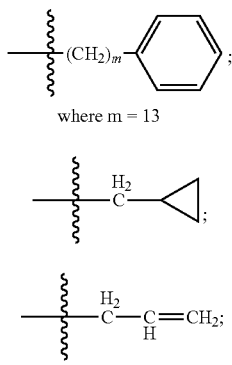

$R^3$ and $R^4$ are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo;
$R^5$, $R^6$, $R^7$, $R^8$, and $R^9$ are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo; and n is an integer from 1 to 5.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

In one embodiment, the peptide is defined by formula II:

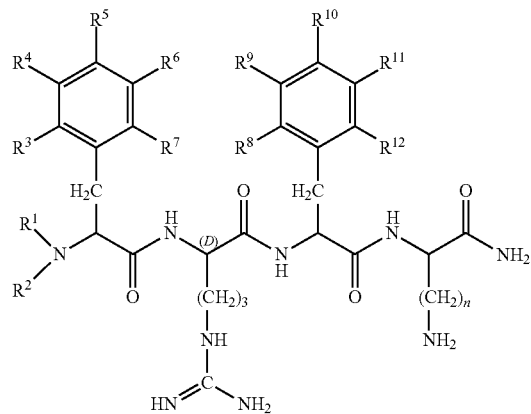

wherein $R^1$ and $R^2$ are each independently selected from
(i) hydrogen;
(ii) linear or branched $C_1$-$C_6$ alkyl;

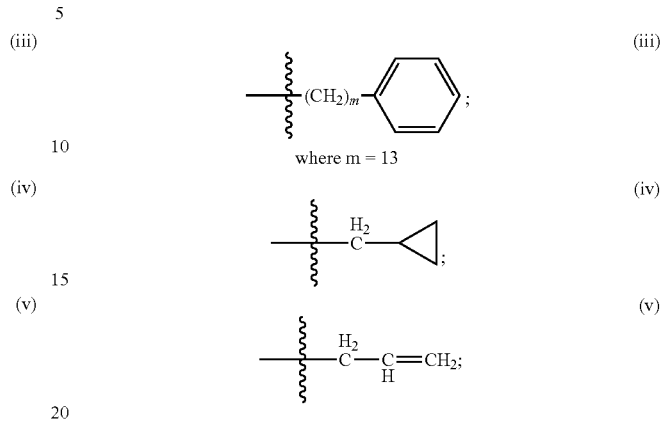

$R^3$, $R^4$, $R^5$, $R^6$, $R^7$, $R^8$, $R^9$, $R^{10}$, $R^{11}$ and $R^{12}$ are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo; and n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

The aromatic-cationic peptides may be administered in a variety of ways. In some embodiments, the peptides may be administered orally, topically, intranasally, intraperitoneally, intravenously, subcutaneously, or transdermally (e.g., by iontophoresis). In some embodiments, the aromatic-cationic peptide is administered by an intra-arterial route.

In one aspect, the present disclosure provides a method for treating atherosclerotic renal artery stenosis in a subject in need thereof, the method comprising administering to the subject a therapeutically effective amount of a peptide D-Arg-2',6'-Dmt-Lys-Phe-NH$_2$ or a pharmaceutically acceptable salt thereof.

In some embodiments, the method further comprises the step of performing a revascularization procedure on the subject. In some embodiments, the revascularization procedure comprises percutaneous transluminal renal angioplasty. In some embodiments, the atherosclerotic renal artery stenosis comprises a disruption or obstruction of the renal microvasculature of the subject. In some embodiments, the subject is at risk for, or suffering from, renal microvasculature rarefaction. In some embodiments, the subject is administered the peptide prior to onset of renal microvasculature rarefaction.

In some embodiments, the subject is administered the peptide prior to the revascularization procedure, after the revascularization procedure, during and after the revascularization procedure or continuously before, during, and after the revascularization procedure.

In some embodiments, the subject is administered the peptide for at least 3 hours after the revascularization procedure, for at least 5 hours after the revascularization procedure, for at least 8 hours after the revascularization procedure, for at least 12 hours after the revascularization procedure, or for at least 24 hours after the revascularization procedure.

In some embodiments, the subject is administered the peptide starting at least 8 hours before the revascularization procedure, starting at least 4 hours before the revascularization procedure, starting at least 2 hours before the revascularization procedure, starting at least 1 hour before the revascularization procedure, or starting at least 10 minutes before the revascularization procedure.

In some embodiments, the revascularization procedure comprises removal of a renal artery occlusion. In some embodiments, the revascularization procedure comprises administration of one or more thrombolytic agents. In some embodiments, the one or more thrombolytic agents are selected from the group consisting of: tissue plasminogen activator, urokinase, prourokinase, streptokinase, acylated form of plasminogen, acylated form of plasmin, and acylated streptokinase-plasminogen complex.

In another aspect, the present disclosure provides a method for treating atherosclerotic renal artery stenosis in a subject in need thereof, the method comprising performing percutaneous transluminal renal angioplasty on the subject and administering to the subject a therapeutically effective amount of a peptide D-Arg-2',6'-Dmt-Lys-Phe-NH$_2$ or a pharmaceutically acceptable salt thereof.

In some embodiments, the subject is at risk for, or suffering from, renal microvasculature rarefaction. In some embodiments, the subject is administered the peptide prior to onset of renal microvasculature rarefaction.

In some embodiments, the subject is administered the peptide prior to the angioplasty, after the angioplasty, during and after the angioplasty or continuously before, during, and after the angioplasty.

In some embodiments, the subject is administered the peptide for at least 3 hours after the angioplasty, for at least 5 hours after the angioplasty, for at least 8 hours after the angioplasty, for at least 12 hours after the angioplasty, or for at least 24 hours after the angioplasty.

In some embodiments, the subject is administered the peptide starting at least 8 hours before the angioplasty, starting at least 4 hours before the angioplasty, starting at least 2 hours before the angioplasty, starting at least 1 hour before the angioplasty, or starting at least 10 minutes before the angioplasty.

In some embodiments, method for treating atherosclerotic renal artery stenosis in a subject in need thereof, comprising performing percutaneous transluminal renal angioplasty on the subject and administering to the subject a therapeutically effective amount of a peptide D-Arg-2',6'-Dmt-Lys-Phe-NH$_2$ or a pharmaceutically acceptable salt thereof includes administering one or more thrombolytic agents to the subject. In some embodiments the one or more thrombolytic agents are selected from the group consisting of: tissue plasminogen activator, urokinase, prourokinase, streptokinase, acylated form of plasminogen, acylated form of plasmin, and acylated streptokinase-plasminogen complex.

In some aspects, the present disclosure provides a method for treating contralateral kidney injury associated with unilateral or bilateral atherosclerotic renal artery stenosis in a subject in need thereof, the method comprising administering to the subject a therapeutically effective amount of a peptide D-Arg-2',6'-Dmt-Lys-Phe-NH$_2$ or a pharmaceutically acceptable salt thereof.

In some aspects, the present disclosure provides a method for treating target organ injury (such as kidney or heart) associated with hypertension or renovascular hypertension in a subject in need thereof, the method comprising administering to the subject a therapeutically effective amount of a peptide D-Arg-2',6'-Dmt-Lys-Phe-NH$_2$ or a pharmaceutically acceptable salt thereof.

In some embodiments, the method further comprises the step of performing a renal revascularization procedure on the subject. In some embodiments, the revascularization procedure comprises percutaneous transluminal renal angioplasty. In some embodiments, the atherosclerotic renal artery stenosis comprises a disruption or obstruction of the renal microvasculature of the subject. In some embodiments, the subject is at risk for, or suffering from, renal microvasculature rarefaction. In some embodiments, the subject is administered the peptide prior to onset of renal microvasculature rarefaction.

In some embodiments, the subject is administered the peptide prior to the revascularization procedure, after the revascularization procedure, during and after the revascularization procedure or continuously before, during, and after the revascularization procedure.

In some embodiments, the subject is administered the peptide for at least 3 hours after the revascularization procedure, for at least 5 hours after the revascularization procedure, for at least 8 hours after the revascularization procedure, for at least 12 hours after the revascularization procedure, or for at least 24 hours after the revascularization procedure.

In some embodiments, the subject is administered the peptide starting at least 8 hours before the revascularization procedure, starting at least 4 hours before the revascularization procedure, starting at least 2 hours before the revascularization procedure, starting at least 1 hour before the revascularization procedure, or starting at least 10 minutes before the revascularization procedure.

In some embodiments, the revascularization procedure comprises removal of a renal artery occlusion. In some embodiments, the revascularization procedure comprises administration of one or more thrombolytic agents. In some embodiments, the one or more thrombolytic agents are selected from the group consisting of: tissue plasminogen activator, urokinase, prourokinase, streptokinase, acylated form of plasminogen, acylated form of plasmin, and acylated streptokinase-plasminogen complex.

In some aspects, the present disclosure provides a method for treating congestive heart failure associated with atherosclerotic renal artery stenosis in a subject in need thereof, the method comprising administering to the subject a therapeutically effective amount of a peptide D-Arg-2',6'-Dmt-Lys-Phe-NH$_2$ or a pharmaceutically acceptable salt thereof.

In some embodiments, the method further comprises the step of performing a renal revascularization procedure on the subject.

In some embodiments, the revascularization procedure comprises percutaneous transluminal renal angioplasty. In some embodiments, the atherosclerotic renal artery stenosis comprises a disruption or obstruction of the renal microvasculature of the subject. In some embodiments, the subject is at risk for, or suffering from, renal microvasculature rarefaction. In some embodiments, the subject is administered the peptide prior to onset of renal microvasculature rarefaction.

In some embodiments, the subject is administered the peptide prior to the revascularization procedure, after the revascularization procedure, during and after the revascularization procedure or continuously before, during, and after the revascularization procedure.

In some embodiments, the subject is administered the peptide for at least 3 hours after the revascularization procedure, for at least 5 hours after the revascularization procedure, for at least 8 hours after the revascularization procedure, for at least 12 hours after the revascularization procedure, or for at least 24 hours after the revascularization procedure.

In some embodiments, the subject is administered the peptide starting at least 8 hours before the revascularization procedure, starting at least 4 hours before the revascularization procedure, starting at least 2 hours before the revascularization procedure, starting at least 33 hour before the revascularization procedure, or starting at least 10 minutes before the revascularization procedure.

In some embodiments, the revascularization procedure comprises removal of a renal artery occlusion. In some embodiments, the revascularization procedure comprises administration of one or more thrombolytic agents. In some embodiments, the one or more thrombolytic agents are selected from the group consisting of: tissue plasminogen activator, urokinase, prourokinase, streptokinase, acylated form of plasminogen, acylated form of plasmin, and acylated streptokinase-plasminogen complex.

In one aspect, the present disclosure provides a method for treating ARVD in a subject in need thereof, the method comprising administering to the subject a therapeutically effective amount of a peptide D-Arg-2',6'-Dmt-Lys-Phe-NH$_2$ or a pharmaceutically acceptable salt thereof.

In some embodiments, the ARVD comprises atherosclerotic renal artery stenosis (ARAS). In some embodiments, the ARVD comprises impaired renal hemodynamics compared to a normal control.

In some embodiments, the impaired renal hemodynamics comprises increased mean renal arterial blood pressure. In some embodiments, the impaired renal hemodynamics comprises reduced renal volume. In some embodiments, the impaired renal hemodynamics comprises reduced cortical perfusion. In some embodiments, the impaired renal hemodynamics comprises reduced renal blood flow (RBF). In some embodiments, the impaired renal hemodynamics comprises a reduced glomerular filtration rate (GFR). In some embodiments, impaired renal hemodynamics comprises reduced cortical blood oxygenation. In some embodiments, the ARVD comprises tubulointerstitial fibrosis.

In some embodiments, treating comprises chronic administration of the peptide D-Arg-2',6'-Dmt-Lys-Phe-NH$_2$ or a pharmaceutically acceptable salt thereof. In some embodiments, chronic administration comprises administration of the peptide D-Arg-2',6'-Dmt-Lys-Phe-NH$_2$ or a pharmaceutically acceptable salt thereof for a period of greater than one week. In some embodiments, chronic administration comprises administration of the peptide D-Arg-2',6'-Dmt-Lys-Phe-NH$_2$ or a pharmaceutically acceptable salt thereof for a period of greater than one year.

In another aspect, the present disclosure provides a method for treating impaired renal hemodynamics caused by atherosclerotic renal artery stenosis (ARAS), the method comprising administering to the subject a therapeutically effective amount of a peptide D-Arg-2',6'-Dmt-Lys-Phe-NH$_2$ or a pharmaceutically acceptable salt thereof.

In some embodiments, the ARAS comprises impaired renal hemodynamics compared to a normal control. In some embodiments, the impaired renal hemodynamics comprises increased mean renal arterial blood pressure. In some embodiments, the impaired renal hemodynamics comprises reduced renal volume. In some embodiments, the impaired renal hemodynamics comprises reduced cortical perfusion. In some embodiments, the impaired renal hemodynamics comprises reduced renal blood flow (RBF). In some embodiments, the impaired renal hemodynamics comprises a reduced glomerular filtration rate (GFR). In some embodiments, the impaired renal hemodynamics comprises reduced cortical blood oxygenation. In some embodiments, the ARAS comprises tubulointerstitial fibrosis.

In some embodiments, treating comprises chronic administration of the peptide D-Arg-2',6'-Dmt-Lys-Phe-NH$_2$ or a pharmaceutically acceptable salt thereof. In some embodiments, chronic administration comprises administration of the peptide D-Arg-2',6'-Dmt-Lys-Phe-NH$_2$ or a pharmaceutically acceptable salt thereof for a period of greater than one week. In some embodiments, chronic administration comprises administration of the peptide D-Arg-2',6'-Dmt-Lys-Phe-NH$_2$ or a pharmaceutically acceptable salt thereof for a period of greater than one year.

In another aspect, the present disclosure provides a method for treating impaired renal hemodynamics caused by atherosclerotic renal artery stenosis (ARAS), the method comprising administering to the subject a therapeutically effective amount of a peptide D-Arg-2',6'-Dmt-Lys-Phe-NH$_2$ or a pharmaceutically acceptable salt thereof in conjunction with one or more antihypertensive agents.

In some embodiments, the one or more antihypertensive agents comprises diuretics, adrenergic receptor antagonists, calcium channel blockers, renin inhibitors, angiotensin converting enzyme (ACE) inhibitors, angiotensin II receptor antagonists, aldosterone antagonists, vasodilators, or alpha-2 agonists.

In some embodiments, the diuretics comprise loop diuretics, thiazide diuretics, thiazide-like diuretics, or potassium-sparing diuretics. In some embodiments, the diuretics comprise bumetanide, ethacrynic acid, furosemide, torsemide, epitizide, hydrochlorothiazide, chlorothiazide, bendroflumethiazide, indapamide, chlorthalidon, metolazone, amiloride, triamterene, or spironolactone.

In some embodiments, the adrenergic receptor antagonists comprise beta blockers, alpha blockers, or mixed alpha and beta blockers. In some embodiments, the adrenergic receptor antagonists comprise atenolol, metoprolol, nadolol, oxprenolol, pindolol, propranolol, timolol, doxazosin, phentolamine, indoramin, phenoxybenzamine, prazosin, terazosin, tolazoline, bucindolol, carvedilol, or labetalol.

In some embodiments, the calcium channel blockers comprise dihydropyridines or non-dihydropyridines. In some embodiments, the calcium channel blockers comprise amlodipine, felodipine, isradipine, lercanidipine, nicardipine, nifedipine, nimodipine, nitrendipine, diltiazem, or verapamil.

In some embodiments, the renin inhibitors comprise Aliskiren®. In some embodiments, the angiotensin converting enzyme (ACE) inhibitors comprise captopril, enalapril, fosinopril, lisinopril, perindopril, quinapril, ramipril, trandolapril, or benazepril. In some embodiments, the angiotensin II receptor antagonists comprise Irbesartan®. In some embodiments, the aldosterone antagonists comprise eplerenone or spironolactone. In some embodiments, the vasodilators antagonists comprise sodium nitroprusside or hydralazine. In some embodiments, the alpha-2 agonists antagonists comprise clonidine, guanabenz, methyldopa, moxonidine, guanethidine, or reserpine.

BRIEF DESCRIPTION OF THE FIGURES

FIG. 8A shows representative periodic acid-Schiff (PAS) staining of renal tissue from normal, ARAS, ARAS+PTRA+vehicle, and ARAS+PTRA+D-Arg-2',6'-Dmt-Lys-Phe-NH$_2$ peptide subjects, and the quantification of tubular injury. FIG. 8B shows representative fibronectin (upper panels) and collagen IV (lower panels) in renal tissue from normal, ARAS, ARAS+PTRA+vehicle, and ARAS+PTRA+D-Arg-2',6'-Dmt-Lys-Phe-NH$_2$ peptide subjects. FIG. 8C shows the quantification of fibronectin and collagen IV staining in renal tissue from normal, ARAS, ARAS+PTRA+vehicle, and ARAS+PTRA+D-Arg-2',6'-Dmt-Lys-Phe-NH$_2$ peptide subjects as a percent of total area. *$p<0.05$ vs. Normal; ‡$p<0.05$ vs. ARAS+PTRA+D-Arg-2',6'-Dmt-Lys-Phe-NH$_2$ peptide.

FIG. 16A is an overview of the experimental timeline. FIG. 16B is a timeline for D-Arg-2',6'-Dmt-Lys-Phe-NH$_2$ infusion. FIG. 16C provides time points for blood sample collection. FIG. 16D provides time points for urine sample collection.

DETAILED DESCRIPTION

Figure 1A:
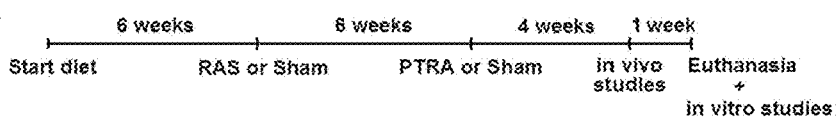
FIG. 1A is a schematic diagram of the experimental protocol showing time points and specific interventions.

It is to be appreciated that certain aspects, modes, embodiments, variations and features of the present disclosure are described below in various levels of detail in order to provide a substantial understanding of the present technology.

In practicing the present methods, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, N Y, 1987); and *Meth. Enzymol.*, Vols. 154 and 155, Wu & Grossman, and Wu, Eds., respectively.

The definitions of certain terms as used in this specification are provided below. Unless defined otherwise, all technical and scientific terms used herein generally have the same meaning as commonly understood by one of ordinary skill in the art to which this technology belongs.

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), intrathecally or topically. In some embodiments, the aromatic-cationic peptide is administered by an intra-arterial route. Administration includes self-administration and/or the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "effective amount" refers to a quantity sufficient to achieve a desired therapeutic and/or prophylactic effect, e.g., an amount which results in the prevention of, or a decrease in, renal ischemia-reperfusion injury, or one or more symptoms associated with renal ischemia, ischemia-reperfusion injury or atherosclerotic renal artery stenosis (ARAS). In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan were able to determine appropriate dosages depending on these and other factors. The compositions can also be administered in combination with one or more additional therapeutic compounds. In the methods described herein, the aromatic-cationic peptides may be administered to a subject having one or more signs or symptoms of renal ischemia injury, renal ischemia-reperfusion injury, hypertension, ARAS, or renovascular hypertension. In other embodiments, the mammal has one or more signs or symptoms of renal insufficiency, such as tiredness or fatigue, tissue swelling, back pain, changes in appetite, poor digestion, elevated serum creatinine, renal hypertension, or changes in amount color, or frequency of urination. For example, by "therapeutically effective amount" of the aromatic-cationic peptides is meant levels at which the physiological effects of renal ischemia-reperfusion injury or ARAS are, at a minimum, ameliorated.

As used herein the term "ischemia reperfusion injury" refers to the damage caused first by restriction of the blood supply to a tissue followed by a sudden resupply of blood and the attendant generation of free radicals. Ischemia is a decrease in the blood supply to the tissue and is followed by reperfusion, a sudden perfusion of oxygen into the deprived tissue. Ischemic injury is the damage caused by the restriction of blood supply to a tissue. Ischemic injury may be due to acute ischemia or chronic ischemia.

An "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, the terms "polypeptide", "peptide", and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the terms "treating" or "treatment" or "alleviation" refers to both therapeutic treatment and prophylactic or preventative measures, wherein the object is to prevent or slow down (lessen) the targeted pathologic condition or disorder. For example, a subject is successfully "treated" for renal ischemia/reperfusion injury associated with ARAS if, after receiving a therapeutic amount of the aromatic-cationic peptides according to the methods described herein, the subject shows observable and/or measurable reduction in renal ischemia-reperfusion injury associated with ARAS. It is also to be appreciated that the various modes of treatment or prevention of medical conditions as described are intended to mean "substantial", which includes total but also less than total treatment or prevention, and wherein some biologically or medically relevant result is achieved.

As used herein, the term "chronic treatment" refers to administering a mode of treatment in excess of a single administration. In some embodiments, the treatment is administered to a subject more than once. In some embodiments, the treatment is administered to a subject more than five times. In some embodiments, the treatment is administered to a subject more than 10, more than 20, more than 30, more than 40, more than 50, more than 60, more than 70, more than 80, more than 90, or more than 100 times. In some embodiments, the treatment is administered to a subject for a period of greater than about 1 week, greater than about 2 weeks, greater than about 3 weeks, greater than about 4 weeks, greater than about 5 weeks, greater than about 6 weeks, greater than about 7 weeks, greater than about 8 weeks, greater than about 9 weeks, greater than about 10 weeks, greater than about 11 weeks, greater than about 12 weeks, greater than about 13 weeks, greater than about 14 weeks, or greater than about 15 weeks. In some embodiments, the treatment is administered to a subject for a period of greater than 1 year, greater than five years, greater than 10 years, or greater than 20 years.

As used herein, "prevention" or "preventing" of a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. As used herein, preventing ischemia-reperfusion injury includes preventing oxidative damage or preventing mitochondrial permeability transitioning, thereby preventing or ameliorating the harmful effects of the loss and subsequent restoration of blood flow to the kidney.

I. Methods of Prevention or Treatment of Renal and Cardiac Injury Associated with Hypertension and/or Renal Artery Stenosis The restoration of blood flow to the kidney is an important part of treatment for renal stenosis. Rapid restoration of blood flow can damage renal microvascular, resulting in reduced kidney function and poor long-term prognosis. This effect is known as ischemia/reperfusion injury.

Reperfusion injury can occur in organs other than the kidney, such as heart, liver, kidney, brain, skin, etc. Tissue damage upon reperfusion was first suggested in brain ischemia. Brains of rabbits that suffered a brief 2½ minutes of ischemia had normal blood flow when the ischemia was relieved. When the rabbits were exposed to longer ischemic periods, normal flow to brain tissues was not restored, even after relief of the vessel obstruction. Prolonged ischemia resulted in significant changes in the microvasculature that interfered with normal flow to the brain cells. The existence of this phenomenon was confirmed in a variety of animal models of brain ischemia. It was also shown in a variety of other organs, including skin, skeletal muscle, and the kidney. Moreover, microcirculation alterations can modulate the organ damage induced by ischemia-reperfusion injury during organ transplantation.

The present technology relates to the treatment or prevention of ischemia injury and/or ischemia-reperfusion injury in mammals through administration of therapeutically effective amounts of aromatic-cationic peptides such as D-Arg-2',6'-Dmt-Lys-Phe-$NH_2$, or pharmaceutically acceptable salts thereof, such as acetate salt or trifluoroacetate salt to subjects in need thereof. In one aspect, the present technology relates to method useful in the treatment or prevention of renal injury associated with renal revascularization in subjects with renal artery stenosis.

In one aspect, the present technology relates to the treatment of ARVD comprising administering to a subject in need thereof therapeutically effective amounts of the peptide D-Arg-2',6'-Dmt-Lys-Phe-$NH_2$, or pharmaceutically acceptable salts thereof, such as acetate salt or trifluoroacetate salt to subjects in need thereof. In some embodiments, the treatment is chronic treatment, administered for a period of greater than 1 week.

In another aspect, the present technology relates to the treatment or prevention of ischemic injury in the absence of tissue reperfusion. For example, peptides may be administered to patients experiencing acute ischemia in one or more tissues or organs who, for example, are not suitable candidates for revascularization procedures or for whom revascularization procedures are not readily available. Additionally or alternatively, the peptides may be administered to patients with chronic ischemia in one or more tissues in order to forestall the need for a revascularization procedure. Patients administered aromatic-cationic peptides for the treatment or prevention of ischemic injury in the absence of tissue reperfusion may additionally be administered peptides prior to, during, and subsequent to revascularization procedures according to the methods described herein.

In one embodiment, the treatment of renal reperfusion injury includes increasing the amount or area of tissue perfusion in a subject compared to a similar subject not administered the aromatic-cationic peptide. In one embodiment, the prevention of renal reperfusion injury includes reducing the amount or area of microvascular damage caused by reperfusion in a subject compared to a similar subject not administered the aromatic-cationic peptide. In some embodiments, treatment or prevention of renal reperfusion injury includes reducing injury to the affected vessel upon reperfusion, reducing the effect of plugging by blood cells, and/or reducing endothelial cell swelling in a subject compared to a similar subject not administered the aromatic-cationic peptide. The extent of the prevention or treatment can be measured by any technique known in the art, including but not limited to measurement of renal volume, renal arterial pressure, renal blood flow (RBF), and glomerular filtration rate (GFR), as well as by imaging techniques known in the art, including, but not limited to CT and micro-CT. Successful prevention or treatment can be determined by comparing the extent of renal reperfusion injury in the subject observed by any of these imaging techniques compared to a control subject or a population of control subjects that are not administered the aromatic-cationic peptide.

In one aspect, the present technology relates to the treatment or prevention of renal reperfusion injury associated with renal revascularization by administration of certain aromatic-cationic peptides, such as D-Arg-2',6'-Dmt-Lys-Phe-NH$_2$, or pharmaceutically acceptable salts thereof, such as acetate salt or trifluoroacetate salt, to a subject in need thereof. Also provided is a method of treating a renal stenosis in a subject to prevent injury to the kidney upon reperfusion of the organ.

In one embodiment, the administration of the aromatic-cationic peptide(s) to a subject is before the occurrence of renal reperfusion injury. For example, in some embodiments, the peptide is administered to inhibit, prevent or treat ischemic injury in a subject in need thereof, and/or to forestall reperfusion treatment and/or alleviate or ameliorate reperfusion injury. Additionally or alternatively, in some embodiments, the administration of the aromatic-cationic peptide(s) to a subject is after the occurrence of renal reperfusion injury. In one embodiment, the method is performed in conjunction with a revascularization procedure. In one embodiment, the revascularization procedure is percutaneous transluminal renal angioplasty (PTRA). In one aspect, the present technology relates to a method of renal revascularization comprising administering to a mammalian subject a therapeutically effective amount of the aromatic cationic peptide and performing PTRA on the subject.

In one embodiment, the subject is administered a peptide such as D-Arg-2',6'-Dmt-Lys-Phe-NH$_2$, or pharmaceutically acceptable salts thereof, such as acetate salt or trifluoroacetate salt, prior to a revascularization procedure. In another embodiment, the subject is administered the peptide after the revascularization procedure. In another embodiment, the subject is administered the peptide during and after the revascularization procedure. In yet another embodiment, the subject is administered the peptide continuously before, during, and after the revascularization procedure. In another embodiment, the subject is administered the peptide regularly (i.e., chronically) following renal artery stenosis and/or a renal revascularization procedure.

In some embodiments, the subject is administered the peptide after the revascularization procedure. In one embodiment, the subject is administered the peptide for at least 3 hours, at least 5 hours, at least 8 hours, at least 12 hours, or at least 24 hours after the revascularization procedure. In some embodiments, the subject is administered the peptide prior to the revascularization procedure. In one embodiment, the subject is administered the peptide starting at least 8 hours, at least 4 hours, at least 2 hours, at least 1 hour, or at least 10 minutes prior to the revascularization procedure. In one embodiment, the subject is administered for at least one week, at least one month or at least one year after the revascularization procedure. In some embodiments, the subject is administered the peptide prior to and after the revascularization procedure. In some embodiments, the subject is administered the peptide as an infusion over a specified period of time. In some embodiments, the peptide is administered to the subject as a bolus.

In some embodiments, the present methods comprise administration of aromatic-cationic peptide in conjunction with one or more thrombolytic agents. In some embodiments, the one or more thrombolytic agents are selected from the group consisting of: tissue plasminogen activator, urokinase, prourokinase, streptokinase, acylated form of plasminogen, acylated form of plasmin, and acylated streptokinase-plasminogen complex.

Also provided herein are methods for the prevention or treatment of stenotic kidney and/or contralateral kidney injury in patients with hypertension, renovascular hypertension or unilateral renal artery stenosis. In such patients, injury to the contralateral kidney is the result of compensatory biological responses to renal artery stenosis. Increased amounts of renin are released from the stenotic kidney in response to diminished pulse pressure in renal arterioles. For example, a 50 percent reduction in renal perfusion pressure leads to an immediate and persistent increase in renin secretion from the ischemic kidney and concomitant suppression of secretion from the contralateral kidney. This has direct effects on sodium excretion, sympathetic nerve activity, intra-renal prostaglandin concentrations, and nitric oxide production; and thus causes renovascular hypertension. When renovascular hypertension is sustained, plasma renin activity decreases (referred to as "reverse tachyphylaxis"). Patients with renovascular hypertension of many years duration suffer extensive nephrosclerosis in the contralateral kidney.

Also provided herein are methods for preventing or treating cardiac injury in patients with hypertension, unilateral renal artery stenosis, or renovascular hypertension. In such patients, cardiac injury is the result of compensatory biological responses to renal artery stenosis and hypertension. As described above, increased amounts of renin are released from the stenotic kidney in response to diminished pulse pressure in renal arterioles, while renin levels are decreased from the contralateral kidney. This results in an overall reduction in plasma renin levels and/or activity. This is accompanied by expanded body fluid volume and increased cardiac output. Sustained increases in cardiac output lead to the development of congestive heart failure. Furthermore, the increase in arterial pressure increases afterload and leads to cardiac hypertrophy. In some embodiments, the peptides are administered in conjunction with a second active agent, e.g., anti-hypertensive agents. Exemplary agents include, without limitation, diuretics, adrenergic receptor agonists, calcium channel blockers, renin inhibitors, ACE inhibitors, angiotensin II receptor agonists, aldosterone antagonists, vasodilators and/or centrally acting adrenergic drugs.

Thus, in some aspects, the present disclosure provides a method for treating contralateral kidney injury associated with unilateral renal artery stenosis in a subject in need thereof, the method comprising administering to the subject a therapeutically effective amount of a peptide D-Arg-2',6'-Dmt-Lys-Phe-NH$_2$ or a pharmaceutically acceptable salt thereof.

In some embodiments, the method further comprises the step of performing a renal revascularization procedure on the subject. In some embodiments, the revascularization procedure comprises percutaneous transluminal renal angioplasty. In some embodiments, the atherosclerotic renal artery stenosis comprises a disruption or obstruction of the renal microvasculature of the subject. In some embodiments, the subject is at risk for, or suffering from, renal microvasculature rarefaction. In some embodiments, the subject is administered the peptide prior to onset of renal microvasculature rarefaction.

In some embodiments, the subject is administered the peptide prior to the revascularization procedure, after the revascularization procedure, during and after the revascularization procedure or continuously before, during, and after the revascularization procedure.

In some embodiments, the subject is administered the peptide for at least 3 hours after the revascularization procedure, for at least 5 hours after the revascularization procedure, for at least 8 hours after the revascularization procedure, for at least 12 hours after the revascularization procedure, or for at least 24 hours after the revascularization procedure.

In some embodiments, the subject is administered the peptide starting at least 8 hours before the revascularization procedure, starting at least 4 hours before the revascularization procedure, starting at least 2 hours before the revascularization procedure, starting at least 1 hour before the revascularization procedure, or starting at least 10 minutes before the revascularization procedure.

In some embodiments, the revascularization procedure comprises removal of a renal artery occlusion. In some embodiments, the revascularization procedure comprises administration of one or more thrombolytic agents. In some embodiments, the one or more thrombolytic agents are selected from the group consisting of: tissue plasminogen activator, urokinase, prourokinase, streptokinase, acylated form of plasminogen, acylated form of plasmin, and acylated streptokinase-plasminogen complex.

In some aspects, the present disclosure provides a method for treating congestive heart failure or cardiac hypertrophy associated with atherosclerotic renal artery stenosis in a subject in need thereof, the method comprising administering to the subject a therapeutically effective amount of a peptide D-Arg-2',6'-Dmt-Lys-Phe-NH$_2$ or a pharmaceutically acceptable salt thereof.

In some embodiments, the method further comprises the step of performing a renal revascularization procedure on the subject.

In some embodiments, the revascularization procedure comprises percutaneous transluminal renal angioplasty. In some embodiments, the atherosclerotic renal artery stenosis comprises a disruption or obstruction of the renal microvasculature of the subject. In some embodiments, the subject is at risk for, or suffering from, renal microvasculature rarefaction. In some embodiments, the subject is administered the peptide prior to onset of renal microvasculature rarefaction.

In some embodiments, the subject is administered the peptide prior to the revascularization procedure, after the revascularization procedure, during and after the revascularization procedure or continuously before, during, and after the revascularization procedure.

In some embodiments, the subject is administered the peptide for at least 3 hours after the revascularization procedure, for at least 5 hours after the revascularization procedure, for at least 8 hours after the revascularization procedure, for at least 12 hours after the revascularization procedure, or for at least 24 hours after the revascularization procedure.

In some embodiments, the subject is administered the peptide starting at least 8 hours before the revascularization procedure, starting at least 4 hours before the revascularization procedure, starting at least 2 hours before the revascularization procedure, starting at least 33 hour before the revascularization procedure, or starting at least 10 minutes before the revascularization procedure.

In some embodiments, the revascularization procedure comprises removal of a renal artery occlusion. In some embodiments, the revascularization procedure comprises administration of one or more thrombolytic agents. In some embodiments, the one or more thrombolytic agents are selected from the group consisting of: tissue plasminogen activator, urokinase, prourokinase, streptokinase, acylated form of plasminogen, acylated form of plasmin, and acylated streptokinase-plasminogen complex.

In some embodiments, the methods disclosed herein comprise administering one or more aromatic-cationic peptides to a subject in need thereof for the treatment or prevention ischemic injury in the absence of tissue reperfusion. In some embodiments, the methods comprise administering one or more peptides, such as D-Arg-2',6'-Dmt-Lys-Phe-NH$_2$ or a pharmaceutically acceptable salt thereof such as acetate or trifluoroacetate salt to patients experiencing acute ischemia in one or more tissues who are not suitable candidates for revascularization procedures or for whom revascularization procedures are not readily available. In some embodiments, the methods comprise administering one or more peptides to patients with chronic ischemia in one or more tissues in order to forestall the need for a revascularization procedure. In some embodiments, patients administered aromatic-cationic peptides for the treatment or prevention of ischemic injury in the absence of tissue reperfusion are additionally administered peptides prior to, during, and subsequent to a revascularization procedure.

II. Preparation of Aromatic-Cationic Peptides of the Present Technology

The aromatic-cationic peptides of the present technology are water-soluble and highly polar. Despite these properties, the peptides can readily penetrate cell membranes. The aromatic-cationic peptides typically include a minimum of three amino acids or a minimum of four amino acids, covalently joined by peptide bonds. The maximum number of amino acids present in the aromatic-cationic peptides is about twenty amino acids covalently joined by peptide bonds. Suitably, the maximum number of amino acids is about twelve, more preferably about nine, and most preferably about six.

The amino acids of the aromatic-cationic peptides can be any amino acid. As used herein, the term "amino acid" is used to refer to any organic molecule that contains at least one amino group and at least one carboxyl group. Typically, at least one amino group is at the a position relative to a carboxyl group. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan, (Trp), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea. Another example of a naturally occurring amino acid includes hydroxyproline (Hyp).

The peptides optionally contain one or more non-naturally occurring amino acids. In some embodiments, the peptide has no amino acids that are naturally occurring. The non-naturally occurring amino acids may be levorotary (L–), dextrorotatory (D–), or mixtures thereof. Non-naturally occurring amino acids are those amino acids that typically are not synthesized in normal metabolic processes in living organisms, and do not naturally occur in proteins. In addition, the non-naturally occurring amino acids suitably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include β-aminobutyric acid, β-aminobutyric acid, γ-aminobutyric acid, δ-aminovaleric acid, and ε-aminocaproic acid. Some examples of non-natural aryl amino acids include ortho-, meta, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are preferably resistant, and more preferably insensitive, to common proteases. Examples of non-naturally occurring amino acids that are resistant or insensitive to proteases include the dextrorotatory (D–) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides should have less than five, preferably less than four, more preferably less than three, and most preferably, less than two contiguous L-amino acids recognized by common proteases, irrespective of whether the amino acids are naturally or non-naturally occurring. In some embodiments, the peptide has only D-amino acids, and no L-amino acids. If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH were referred to below as ($p_m$). The total number of amino acid residues in the peptide were referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH. As an example of calculating net charge, the peptide Tyr-D-Arg-Phe-Lys-Glu-His-Trp-D-Arg has one negatively charged amino acid (i.e., Glu) and four positively charged amino acids (i.e., two Arg residues, one Lys, and one His). Therefore, the above peptide has a net positive charge of three.

In one embodiment, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 1

| Amino acid number and net positive charges ($3p_m \le p + 1$) | | | | | | | | | | | | | | | | | | |
|---|---|---|---|---|---|---|---|---|---|---|---|---|---|---|---|---|---|---|
| (r) | 3 | 4 | 5 | 6 | 7 | 8 | 9 | 10 | 11 | 12 | 13 | 14 | 15 | 16 | 17 | 18 | 19 | 20 |
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 2

Amino acid number and net positive charges ($2p_m \le p + 1$)

| (r)     | 3 | 4 | 5 | 6 | 7 | 8 | 9 | 10 | 11 | 12 | 13 | 14 | 15 | 16 | 17 | 18 | 19 | 20 |
|---------|---|---|---|---|---|---|---|----|----|----|----|----|----|----|----|----|----|----|
| ($p_m$) | 2 | 2 | 3 | 3 | 4 | 4 | 5 | 5  | 6  | 6  | 7  | 7  | 8  | 8  | 9  | 9  | 10 | 10 |

In one embodiment, the minimum number of net positive charges ($p_m$) and the total number of amino acid residues (r) are equal. In another embodiment, the peptides have three or four amino acid residues and a minimum of one net positive charge, suitably, a minimum of two net positive charges and more preferably a minimum of three net positive charges.

It is also important that the aromatic-cationic peptides have a minimum number of aromatic groups in comparison to the total number of net positive charges ($p_t$). The minimum number of aromatic groups were referred to below as (a). Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH ($p_t$) wherein 3a is the largest number that is less than or equal to $p_t+1$, except that when $p_t$ is 1, a may also be 1. In this embodiment, the relationship between the minimum number of aromatic groups (a) and the total number of net positive charges ($p_t$) is as follows:

TABLE 3

Aromatic groups and net positive charges ($3a \le p_t$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---------|---|---|---|---|---|---|---|---|---|----|----|----|----|----|----|----|----|----|----|----|
| (a)     | 1 | 1 | 1 | 1 | 2 | 2 | 2 | 2 | 3 | 3  | 3  | 4  | 4  | 4  | 5  | 5  | 5  | 6  | 6  | 7  |

In another embodiment, the aromatic-cationic peptides have a relationship between the minimum number of aromatic groups (a) and the total number of net positive charges ($p_t$) wherein 2a is the largest number that is less than or equal to $p_t+1$. In this embodiment, the relationship between the minimum number of aromatic amino acid residues (a) and the total number of net positive charges ($p_t$) is as follows:

TABLE 4

Aromatic groups and net positive charges ($2a \le p_t$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---------|---|---|---|---|---|---|---|---|---|----|----|----|----|----|----|----|----|----|----|----|
| (a)     | 1 | 1 | 2 | 2 | 3 | 3 | 4 | 4 | 5 | 5  | 6  | 6  | 7  | 7  | 8  | 8  | 9  | 9  | 10 | 10 |

In another embodiment, the number of aromatic groups (a) and the total number of net positive charges ($p_t$) are equal.

Carboxyl groups, especially the terminal carboxyl group of a C-terminal amino acid, are suitably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides may also be amidated wherever they occur within the peptide. The amidation at these internal positions may be with ammonia or any of the primary or secondary amines described above.

In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

Aromatic-cationic peptides include, but are not limited to, the following peptide examples:

2',6'-Dmp-D-Arg-2',6'-Dmt-Lys-NH$_2$
2',6'-Dmp-D-Arg-Phe-Lys-NH$_2$
2',6'-Dmt-D-Arg-Phe-Orn-NH$_2$
2',6'-Dmt-D-Arg-Phe-Ahp(2-aminoheptanoicacid)-NH$_2$
2',6'-Dmt-D-Arg-Phe-Lys-NH$_2$
2',6'-Dmt-D-Cit-Phe-Lys-NH$_2$ -continued Ala-D-Phe-D-Arg-Tyr-Lys-D-Trp-His-D-Tyr-Gly-Phe
Arg-D-Leu-D-Tyr-Phe-Lys-Glu-D-Lys-Arg-D-Trp-Lys-D-Phe-Tyr-D-Arg-Gly
Asp-Arg-D-Phe-Cys-Phe-D-Arg-D-Lys-Tyr-Arg-D-Tyr-Trp-D-His-Tyr- -continued D-Phe-Lys-Phe
Asp-D-Trp-Lys-Tyr-D-His-Phe-Arg-D-Gly-Lys-NH$_2$
D-Arg-2',6'-Dmt-Lys-Phe-NH$_2$
D-Glu-Asp-Lys-D-Arg-D-His-Phe-Phe-D-Val-Tyr-Arg-Tyr-D-Tyr-Arg-His-Phe-NH$_2$
D-His-Glu-Lys-Tyr-D-Phe-Arg
D-His-Lys-Tyr-D-Phe-Glu-D-Asp-D-Asp-D-His-D-Lys-Arg-Trp-NH$_2$ -continued D-Tyr-Trp-Lys-NH$_2$
Glu-Arg-D-Lys-Tyr-D-Val-Phe-D-His-Trp-Arg-D-Gly-Tyr-Arg-D-Met-NH$_2$
Gly-Ala-Lys-Phe-D-Lys-Glu-Arg-Tyr-His-D-Arg-D-Arg-Asp-Tyr-Trp-D-His-Trp-His-D-Lys-Asp.
Gly-D-Phe-Lys-His-D-Arg-Tyr-NH$_2$
His-Tyr-D-Arg-Trp-Lys-Phe-D-Asp-Ala-Arg-Cys-D-Tyr-His-Phe-D-Lys-Tyr-His-Ser-NH$_2$
Lys-D-Arg-Tyr-NH$_2$
Lys-D-Gln-Tyr-Arg-D-Phe-Trp-NH$_2$
Lys-Trp-D-Tyr-Arg-Asn-Phe-Tyr-D-His-NH$_2$
Met-Tyr-D-Arg-Phe-Arg-NH$_2$
Met-Tyr-D-Lys-Phe-Arg
Phe-Arg-D-His-Asp
Phe-D-Arg-2',6'-Dmt-Lys-NH$_2$
Phe-D-Arg-His
Phe-D-Arg-Lys-Trp-Tyr-D-Arg-His
Phe-D-Arg-Phe-Lys-NH$_2$
Phe-Phe-D-Tyr-Arg-Glu-Asp-D-Lys-Arg-D-Arg-His-Phe-NH$_2$
Phe-Tyr-Lys-D-Arg-Trp-His-D-Lys-D-Lys-Glu-Arg-D-Tyr-Thr
Thr-Gly-Tyr-Arg-D-His-Phe-Trp-D-His-Lys
Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH$_2$
Trp-D-Lys-Tyr-Arg-NH$_2$
Trp-Lys-Phe-D-Asp-Arg-Tyr-D-His-Lys
Tyr-Asp-D-Lys-Tyr-Phe-D-Lys-D-Arg-Phe-Pro-D-Tyr-His-Lys
Tyr-D-Arg-Phe-Lys-Glu-NH$_2$
Tyr-D-Arg-Phe-Lys-NH$_2$
Tyr-D-His-Phe-D-Arg-Asp-Lys-D-Arg-His-Trp-D-His-Phe
Tyr-His-D-Gly-Met
Val-D-Lys-His-Tyr-D-Phe-Ser-Tyr-Arg-NH$_2$ In one embodiment, the peptides have mu-opioid receptor agonist activity (i.e., they activate the mu-opioid receptor). Mu-opioid activity can be assessed by radioligand binding to cloned mu-opioid receptors or by bioassays using the guinea pig ileum (Schiller et al., *Eur. J. Med. Chem.*, 35:895-901, 2000; Zhao et al., *J. Pharmacol. Exp. Ther.*, 307:947-954, 2003). Activation of the mu-opioid receptor typically elicits an analgesic effect. In certain instances, an aromatic-cationic peptide having mu-opioid receptor agonist activity is preferred. For example, during short-term treatment, such as in an acute disease or condition, it may be beneficial to use an aromatic-cationic peptide that activates the mu-opioid receptor. Such acute diseases and conditions are often associated with moderate or severe pain. In these instances, the analgesic effect of the aromatic-cationic peptide may be beneficial in the treatment regimen of the human patient or other mammal. An aromatic-cationic peptide which does not activate the mu-opioid receptor, however, may also be used with or without an analgesic, according to clinical requirements.

Alternatively, in other instances, an aromatic-cationic peptide that does not have mu-opioid receptor agonist activity is preferred. For example, during long-term treatment, such as in a chronic disease state or condition, the use of an aromatic-cationic peptide that activates the mu-opioid receptor may be contraindicated. In these instances, the potentially adverse or addictive effects of the aromatic-cationic peptide may preclude the use of an aromatic-cationic peptide that activates the mu-opioid receptor in the treatment regimen of a human patient or other mammal. Potential adverse effects may include sedation, constipation and respiratory depression. In such instances an aromatic-cationic peptide that does not activate the mu-opioid receptor may be an appropriate treatment.

Peptides which have mu-opioid receptor agonist activity are typically those peptides which have a tyrosine residue or a tyrosine derivative at the N-terminus (i.e., the first amino acid position). Suitable derivatives of tyrosine include 2'-methyltyrosine (Mmt); 2',6'-dimethyltyrosine (2',6'-Dmt); 3',5'-dimethyltyrosine (3',5'Dmt); N,2',6'-trimethyltyrosine (Tmt); and 2'-hydroxy-6'-methyltryosine (Hmt).

In one embodiment, a peptide that has mu-opioid receptor agonist activity has the formula Tyr-D-Arg-Phe-Lys-NH$_2$. This peptide has a net positive charge of three, contributed by the amino acids tyrosine, arginine, and lysine and has two aromatic groups contributed by the amino acids phenylalanine and tyrosine. The tyrosine can be a modified derivative of tyrosine such as in 2',6'-dimethyltyrosine to produce the compound having the formula 2',6'-Dmt-D-Arg-Phe-Lys-NH$_2$. This peptide has a molecular weight of 640 and carries a net three positive charge at physiological pH. The peptide readily penetrates the plasma membrane of several mammalian cell types in an energy-independent manner (Zhao et al., *J. Pharmacol Exp Ther.*, 304:425-432, 2003).

Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine. In one embodiment, the amino acid at the N-terminus is phenylalanine or its derivative. Exemplary derivatives of phenylalanine include 2'-methylphenylalanine (Mmp), 2',6'-dimethylphenylalanine (2',6'-Dmp), N,2',6'-trimethylphenylalanine (Tmp), and 2'-hydroxy-6'-methylphenylalanine (Hmp).

An example of an aromatic-cationic peptide that does not have mu-opioid receptor agonist activity has the formula Phe-D-Arg-Phe-Lys-NH$_2$. Alternatively, the N-terminal phenylalanine can be a derivative of phenylalanine such as 2',6'-dimethylphenylalanine (2',6'-Dmp). In one embodiment, a peptide with 2',6'-dimethylphenylalanine at amino acid position 1 has the formula 2',6'-Dmp-D-Arg-Phe-Lys-NH$_2$. In one embodiment, the amino acid sequence is rearranged such that Dmt is not at the N-terminus. An example of such an aromatic-cationic peptide that does not have mu-opioid receptor agonist activity has the formula D-Arg-2',6'-Dmt-Lys-Phe-NH$_2$.

The peptides mentioned herein and their derivatives can further include functional analogs. A peptide is considered a functional analog if the analog has the same function as the stated peptide. The analog may, for example, be a substitution variant of a peptide, wherein one or more amino acids are substituted by another amino acid. Suitable substitution variants of the peptides include conservative amino acid substitutions. Amino acids may be grouped according to their physicochemical characteristics as follows:

(a) Non-polar amino acids: Ala(A) Ser(S) Thr(T) Pro(P) Gly(G) Cys (C);
(b) Acidic amino acids: Asn(N) Asp(D) Glu(E) Gln(Q);
(c) Basic amino acids: His(H) Arg(R) Lys(K);
(d) Hydrophobic amino acids: Met(M) Leu(L) Ile(I) Val (V); and
(e) Aromatic amino acids: Phe(F) Tyr(Y) Trp(W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group is generally more likely to alter the characteristics of the original peptide.

Examples of peptides that activate mu-opioid receptors include, but are not limited to, the aromatic-cationic peptides shown in Table 5.

TABLE 5

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Arg | Phe | Lys | $NH_2$ |
| Tyr | D-Arg | Phe | Orn | $NH_2$ |
| Tyr | D-Arg | Phe | Dab | $NH_2$ |
| Tyr | D-Arg | Phe | Dap | $NH_2$ |
| 2'6'Dmt | D-Arg | Phe | Lys | $NH_2$ |
| 2'6'Dmt | D-Arg | Phe | Lys-NH(CH$_2$)$_2$-NH-dns | $NH_2$ |
| 2'6'Dmt | D-Arg | Phe | Lys-NH(CH$_2$)$_2$-NH-atn | $NH_2$ |
| 2'6'Dmt | D-Arg | Phe | dnsLys | $NH_2$ |
| 2'6'Dmt | D-Cit | Phe | Lys | $NH_2$ |
| 2'6'Dmt | D-Cit | Phe | Ahp | $NH_2$ |
| 2'6'Dmt | D-Arg | Phe | Orn | $NH_2$ |
| 2'6'Dmt | D-Arg | Phe | Dab | $NH_2$ |
| 2'6'Dmt | D-Arg | Phe | Dap | $NH_2$ |
| 2'6'Dmt | D-Arg | Phe | Ahp(2-aminoheptanoic acid) | $NH_2$ |
| Bio-2'6'Dmt | D-Arg | Phe | Lys | $NH_2$ |
| 3'5'Dmt | D-Arg | Phe | Lys | $NH_2$ |
| 3'5'Dmt | D-Arg | Phe | Orn | $NH_2$ |
| 3'5'Dmt | D-Arg | Phe | Dab | $NH_2$ |
| 3'5'Dmt | D-Arg | Phe | Dap | $NH_2$ |
| Tyr | D-Arg | Tyr | Lys | $NH_2$ |
| Tyr | D-Arg | Tyr | Orn | $NH_2$ |
| Tyr | D-Arg | Tyr | Dab | $NH_2$ |
| Tyr | D-Arg | Tyr | Dap | $NH_2$ |
| 2'6'Dmt | D-Arg | Tyr | Lys | $NH_2$ |
| 2'6'Dmt | D-Arg | Tyr | Orn | $NH_2$ |
| 2'6'Dmt | D-Arg | Tyr | Dab | $NH_2$ |
| 2'6'Dmt | D-Arg | Tyr | Dap | $NH_2$ |
| 2'6'Dmt | D-Arg | 2'6'Dmt | Lys | $NH_2$ |
| 2'6'Dmt | D-Arg | 2'6'Dmt | Orn | $NH_2$ |
| 2'6'Dmt | D-Arg | 2'6'Dmt | Dab | $NH_2$ |
| 2'6'Dmt | D-Arg | 2'6'Dmt | Dap | $NH_2$ |
| 3'5'Dmt | D-Arg | 3'5'Dmt | Arg | $NH_2$ |
| 3'5'Dmt | D-Arg | 3'5'Dmt | Lys | $NH_2$ |
| 3'5'Dmt | D-Arg | 3'5'Dmt | Orn | $NH_2$ |
| 3'5'Dmt | D-Arg | 3'5'Dmt | Dab | $NH_2$ |
| Tyr | D-Lys | Phe | Dap | $NH_2$ |
| Tyr | D-Lys | Phe | Arg | $NH_2$ |
| Tyr | D-Lys | Phe | Lys | $NH_2$ |
| Tyr | D-Lys | Phe | Orn | $NH_2$ |
| 2'6'Dmt | D-Lys | Phe | Dab | $NH_2$ |
| 2'6'Dmt | D-Lys | Phe | Dap | $NH_2$ |
| 2'6'Dmt | D-Lys | Phe | Arg | $NH_2$ |
| 2'6'Dmt | D-Lys | Phe | Lys | $NH_2$ |
| 3'5'Dmt | D-Lys | Phe | Orn | $NH_2$ |
| 3'5'Dmt | D-Lys | Phe | Dab | $NH_2$ |
| 3'5'Dmt | D-Lys | Phe | Dap | $NH_2$ |
| 3'5'Dmt | D-Lys | Phe | Arg | $NH_2$ |
| Tyr | D-Lys | Tyr | Lys | $NH_2$ |
| Tyr | D-Lys | Tyr | Orn | $NH_2$ |
| Tyr | D-Lys | Tyr | Dab | $NH_2$ |
| Tyr | D-Lys | Tyr | Dap | $NH_2$ |
| 2'6'Dmt | D-Lys | Tyr | Lys | $NH_2$ |
| 2'6'Dmt | D-Lys | Tyr | Orn | $NH_2$ |
| 2'6'Dmt | D-Lys | Tyr | Dab | $NH_2$ |
| 2'6'Dmt | D-Lys | Tyr | Dap | $NH_2$ |
| 2'6'Dmt | D-Lys | 2'6'Dmt | Lys | $NH_2$ |
| 2'6'Dmt | D-Lys | 2'6'Dmt | Orn | $NH_2$ |
| 2'6'Dmt | D-Lys | 2'6'Dmt | Dab | $NH_2$ |
| 2'6'Dmt | D-Lys | 2'6'Dmt | Dap | $NH_2$ |
| 2'6'Dmt | D-Arg | Phe | dnsDap | $NH_2$ |
| 2'6'Dmt | D-Arg | Phe | atnDap | $NH_2$ |
| 3'5'Dmt | D-Lys | 3'5'Dmt | Lys | $NH_2$ |
| 3'5'Dmt | D-Lys | 3'5'Dmt | Orn | $NH_2$ |
| 3'5'Dmt | D-Lys | 3'5'Dmt | Dab | $NH_2$ |
| 3'5'Dmt | D-Lys | 3'5'Dmt | Dap | $NH_2$ |
| Tyr | D-Lys | Phe | Arg | $NH_2$ |
| Tyr | D-Orn | Phe | Arg | $NH_2$ |
| Tyr | D-Dab | Phe | Arg | $NH_2$ |
| Tyr | D-Dap | Phe | Arg | $NH_2$ |
| 2'6'Dmt | D-Arg | Phe | Arg | $NH_2$ |
| 2'6'Dmt | D-Lys | Phe | Arg | $NH_2$ |
| 2'6'Dmt | D-Orn | Phe | Arg | $NH_2$ |
| 2'6'Dmt | D-Dab | Phe | Arg | $NH_2$ |
| 3'5'Dmt | D-Dap | Phe | Arg | $NH_2$ |
| 3'5'Dmt | D-Arg | Phe | Arg | $NH_2$ |
| 3'5'Dmt | D-Lys | Phe | Arg | $NH_2$ |
| 3'5'Dmt | D-Orn | Phe | Arg | $NH_2$ |
| Tyr | D-Lys | Tyr | Arg | $NH_2$ |
| Tyr | D-Orn | Tyr | Arg | $NH_2$ |
| Tyr | D-Dab | Tyr | Arg | $NH_2$ |
| Tyr | D-Dap | Tyr | Arg | $NH_2$ |
| 2'6'Dmt | D-Arg | 2'6'Dmt | Arg | $NH_2$ |
| 2'6'Dmt | D-Lys | 2'6'Dmt | Arg | $NH_2$ |
| 2'6'Dmt | D-Orn | 2'6'Dmt | Arg | $NH_2$ |
| 2'6'Dmt | D-Dab | 2'6'Dmt | Arg | $NH_2$ |
| 3'5'Dmt | D-Dap | 3'5'Dmt | Arg | $NH_2$ |
| 3'5'Dmt | D-Arg | 3'5'Dmt | Arg | $NH_2$ |
| 3'5'Dmt | D-Lys | 3'5'Dmt | Arg | $NH_2$ |
| 3'5'Dmt | D-Orn | 3'5'Dmt | Arg | $NH_2$ |
| Mmt | D-Arg | Phe | Lys | $NH_2$ |
| Mmt | D-Arg | Phe | Orn | $NH_2$ |
| Mmt | D-Arg | Phe | Dab | $NH_2$ |
| Mmt | D-Arg | Phe | Dap | $NH_2$ |
| Tmt | D-Arg | Phe | Lys | $NH_2$ |
| Tmt | D-Arg | Phe | Orn | $NH_2$ |
| Tmt | D-Arg | Phe | Dab | $NH_2$ |
| Tmt | D-Arg | Phe | Dap | $NH_2$ |
| Hmt | D-Arg | Phe | Lys | $NH_2$ |
| Hmt | D-Arg | Phe | Orn | $NH_2$ |
| Hmt | D-Arg | Phe | Dab | $NH_2$ |
| Hmt | D-Arg | Phe | Dap | $NH_2$ |
| Mmt | D-Lys | Phe | Lys | $NH_2$ |
| Mmt | D-Lys | Phe | Orn | $NH_2$ |
| Mmt | D-Lys | Phe | Dab | $NH_2$ |
| Mmt | D-Lys | Phe | Dap | $NH_2$ |
| Mmt | D-Lys | Phe | Arg | $NH_2$ |
| Tmt | D-Lys | Phe | Lys | $NH_2$ |
| Tmt | D-Lys | Phe | Orn | $NH_2$ |
| Tmt | D-Lys | Phe | Dab | $NH_2$ |
| Tmt | D-Lys | Phe | Dap | $NH_2$ |
| Tmt | D-Lys | Phe | Arg | $NH_2$ |
| Hmt | D-Lys | Phe | Lys | $NH_2$ |
| Hmt | D-Lys | Phe | Orn | $NH_2$ |
| Hmt | D-Lys | Phe | Dab | $NH_2$ |
| Hmt | D-Lys | Phe | Dap | $NH_2$ |
| Hmt | D-Lys | Phe | Arg | $NH_2$ |
| Mmt | D-Orn | Phe | Arg | $NH_2$ |
| Mmt | D-Dab | Phe | Arg | $NH_2$ |
| Mmt | D-Dap | Phe | Arg | $NH_2$ |
| Mmt | D-Arg | Phe | Arg | $NH_2$ |
| Tmt | D-Lys | Phe | Arg | $NH_2$ |
| Tmt | D-Orn | Phe | Arg | $NH_2$ |
| Tmt | D-Dab | Phe | Arg | $NH_2$ |
| Tmt | D-Dap | Phe | Arg | $NH_2$ |
| Tmt | D-Arg | Phe | Arg | $NH_2$ |
| Hmt | D-Lys | Phe | Arg | $NH_2$ |
| Hmt | D-Orn | Phe | Arg | $NH_2$ |
| Hmt | D-Dab | Phe | Arg | $NH_2$ |
| Hmt | D-Dap | Phe | Arg | $NH_2$ |
| Hmt | D-Arg | Phe | Arg | $NH_2$ |

Dab = diaminobutyric
Dap = diaminopropionic acid
Dmt = dimethyltyrosine
Mmt = 2'-methyltyrosine
Tmt = N, 2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Dab=diaminobutyric
Dap=diaminopropionic acid
Dmt=dimethyltyrosine
Mmt=T-methyltyrosine Tmt=N, 2',6'-trimethyltyrosine
Hmt=2'-hydroxy,6'-methyltyrosine
dnsDap=β-dansyl-L-α,β-diaminopropionic acid
atnDap=β-anthraniloyl-L-α,β-diaminopropionic acid
Bio=biotin Examples of analogs that do not activate mu-opioid receptors include, but are not limited to, the aromatic-cationic peptides shown in Table 6.

TABLE 6

Peptide Analogs Lacking Mu-Opioid Activity

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | $NH_2$ |
| D-Arg | Dmt | Phe | Lys | $NH_2$ |
| D-Arg | Phe | Lys | Dmt | $NH_2$ |
| D-Arg | Phe | Dmt | Lys | $NH_2$ |
| D-Arg | Lys | Dmt | Phe | $NH_2$ |
| D-Arg | Lys | Phe | Dmt | $NH_2$ |
| Phe | Lys | Dmt | D-Arg | $NH_2$ |
| Phe | Lys | D-Arg | Dmt | $NH_2$ |
| Phe | D-Arg | Phe | Lys | $NH_2$ |
| Phe | D-Arg | Dmt | Lys | $NH_2$ |
| Phe | D-Arg | Lys | Dmt | $NH_2$ |
| Phe | Dmt | D-Arg | Lys | $NH_2$ |
| Phe | Dmt | Lys | D-Arg | $NH_2$ |
| Lys | Phe | D-Arg | Dmt | $NH_2$ |
| Lys | Phe | Dmt | D-Arg | $NH_2$ |
| Lys | Dmt | D-Arg | Phe | $NH_2$ |
| Lys | Dmt | Phe | D-Arg | $NH_2$ |
| Lys | D-Arg | Phe | Dmt | $NH_2$ |
| Lys | D-Arg | Dmt | Phe | $NH_2$ |
| D-Arg | Dmt | D-Arg | Phe | $NH_2$ |
| D-Arg | Dmt | D-Arg | Dmt | $NH_2$ |
| D-Arg | Dmt | D-Arg | Tyr | $NH_2$ |
| D-Arg | Dmt | D-Arg | Trp | $NH_2$ |
| Trp | D-Arg | Phe | Lys | $NH_2$ |
| Trp | D-Arg | Tyr | Lys | $NH_2$ |
| Trp | D-Arg | Trp | Lys | $NH_2$ |
| Trp | D-Arg | Dmt | Lys | $NH_2$ |
| D-Arg | Trp | Lys | Phe | $NH_2$ |
| D-Arg | Trp | Phe | Lys | $NH_2$ |
| D-Arg | Trp | Lys | Dmt | $NH_2$ |
| D-Arg | Trp | Dmt | Lys | $NH_2$ |
| D-Arg | Lys | Trp | Phe | $NH_2$ |
| D-Arg | Lys | Trp | Dmt | $NH_2$ |
| Cha | D-Arg | Phe | Lys | $NH_2$ |
| Ala | D-Arg | Phe | Lys | $NH_2$ |

Cha = cyclohexyl alanine

Cha=cyclohexyl alanine

The amino acids of the peptides shown in Table 5 and 6 may be in either the L- or the D-configuration.

The peptides may be synthesized by any of the methods well known in the art. Suitable methods for chemically synthesizing the protein include, for example, those described by Stuart and Young in *Solid Phase Peptide Synthesis*, Second Edition, Pierce Chemical Company (1984), and in *Methods Enzymol.*, 289, Academic Press, Inc, New York (1997).

III. Prophylactic and Therapeutic Uses of the Aromatic-Cationic Peptide of the Present Technology General. The aromatic-cationic peptides described herein, such as D-Arg-2',6'-Dmt-Lys-Phe-$NH_2$, or pharmaceutically acceptable salts thereof, such as acetate salt or trifluoroacetate salt, are useful to prevent or treat a disease or condition. Specifically, the disclosure provides for both prophylactic and therapeutic methods of treating a subject at risk of (or susceptible to) renal injury associated with renal artery stenosis or associated with treatment of renal artery stenosis. In some embodiments, the methods comprise performing a revascularization procedure on a subject in need thereof. In some embodiments, the revascularization procedure comprises percutaneous transluminal renal angioplasty (PTRA). Accordingly, the present methods provide for the prevention and/or treatment of renal reperfusion injury in a subject in need thereof by administering an effective amount of an aromatic-cationic peptide.

Determination of the Biological Effect of the Aromatic-Cationic Peptide-Based Therapeutic. In various embodiments, suitable in vitro or in vivo assays are performed to determine the effect of a specific aromatic-cationic peptide-based therapeutic and whether its administration is indicated for treatment. In various embodiments, in vitro assays are performed with representative animal models, to determine if a given aromatic-cationic peptide-based therapeutic exerts the desired effect in preventing or treating renal reperfusion injury. Compounds for use in therapy can be tested in suitable animal model systems including, but not limited to rats, mice, chicken, pigs, cows, monkeys, rabbits, sheep, guinea pig, and the like, prior to testing in human subjects. Similarly, for in vivo testing, any of the animal model systems known in the art can be used prior to administration to human subjects.

Prophylactic Methods. In one aspect, the present disclosure provides a method for preventing renal ischemic or reperfusion injury in a subject by administering to the subject an aromatic-cationic peptide that prevents the initiation or progression of the condition. Subjects at risk for renal reperfusion injury can be identified by, e.g., any or a combination of diagnostic or prognostic assays as described herein or as known in the art. In prophylactic applications, pharmaceutical compositions or medicaments of aromatic-cationic peptide is administered to a subject susceptible to, or otherwise at risk of a disease or condition in an amount sufficient to eliminate or reduce the risk, lessen the severity, or delay the outset of the disease or condition, including biochemical, histological and/or behavioral symptoms of the disease or condition, its complications and intermediate pathological phenotypes presenting during development of the disease or condition. Administration of a prophylactic aromatic-cationic peptide can occur prior to the manifestation of symptoms characteristic of the aberrancy, such that a disease or disorder is prevented or, alternatively, delayed in its progression. The appropriate compound can be determined based on screening assays described above.

In some embodiments, prophylactic methods comprise administration of aromatic-cationic peptide in conjunction with one or more thrombolytic agents. In some embodiments, the one or more thrombolytic agents are selected from the group consisting of: tissue plasminogen activator, urokinase, prourokinase, streptokinase, acylated form of plasminogen, acylated form of plasmin, and acylated streptokinase-plasminogen complex.

Therapeutic Methods. Another aspect of the technology includes methods of treating renal reperfusion injury in a subject by administering to the subject an aromatic-cationic peptide for therapeutic purposes. In therapeutic applications, compositions or medicaments are administered to a subject suspected of, or already suffering from such a disease or condition in an amount sufficient to cure, or at least partially arrest, the symptoms of the disease or condition, including its complications and intermediate pathological phenotypes in development of the disease. or condition As such, the technology provides methods of treating an individual afflicted with renal reperfusion injury.

In some embodiments, therapeutic methods comprise administration of aromatic-cationic peptide in conjunction with one or more active agents. In some embodiments, peptide administration is chronic.

In some embodiments the peptide is administered in conjunction with one or more thrombolytic agents. In some embodiments, the one or more thrombolytic agents are selected from the group consisting of: tissue plasminogen activator, urokinase, prourokinase, streptokinase, acylated form of plasminogen, acylated form of plasmin, and acylated streptokinase-plasminogen complex.

In some embodiments, therapeutic methods comprise administration of aromatic-cationic peptide in conjunction with one or more antihypertensive agents. In some embodiments, the one or more antihypertensive agents comprise diuretics, adrenergic receptor antagonists, calcium channel blockers, renin inhibitors, angiotensin converting enzyme (ACE) inhibitors, angiotensin II receptor antagonists, aldosterone antagonists, vasodilators, or alpha-2 agonists.

In some embodiments, the diuretics comprise loop diuretics, thiazide diuretics, thiazide-like diuretics, or potassium-sparing diuretics. In some embodiments, the diuretics comprise bumetanide, ethacrynic acid, furosemide, torsemide, epitizide, hydrochlorothiazide, chlorothiazide, bendroflumethiazide, indapamide, chlorthalidon, metolazone, amiloride, triamterene, or spironolactone.

In some embodiments, the adrenergic receptor antagonists comprise beta blockers, alpha blockers, or mixed alpha and beta blockers. In some embodiments, the adrenergic receptor antagonists comprise atenolol, metoprolol, nadolol, oxprenolol, pindolol, propranolol, timolol, doxazosin, phentolamine, indoramin, phenoxybenzamine, prazosin, terazosin, tolazoline, bucindolol, carvedilol, or labetalol.

In some embodiments, the calcium channel blockers comprise dihydropyridines or non-dihydropyridines. In some embodiments, the calcium channel blockers comprise amlodipine, felodipine, isradipine, lercanidipine, nicardipine, nifedipine, nimodipine, nitrendipine, diltiazem, or verapamil.

In some embodiments, the renin inhibitors comprise Aliskiren®.

In some embodiments, the angiotensin converting enzyme (ACE) inhibitors comprise captopril, enalapril, fosinopril, lisinopril, perindopril, quinapril, ramipril, trandolapril, or benazepril.

In some embodiments, the angiotensin II receptor antagonists comprise Irbesartan®.

In some embodiments, the aldosterone antagonists comprise eplerenone or spironolactone.

In some embodiments, the vasodilators antagonists comprise sodium nitroprusside or hydralazine.

In some embodiments, the alpha-2 agonists antagonists comprise clonidine, guanabenz, methyldopa, moxonidine, guanethidine, or reserpine.

V. Modes of Administration and Effective Dosages

Any method known to those in the art for contacting a cell, organ or tissue with a peptide may be employed. Suitable methods include in vitro, ex vivo, or in vivo methods. In vivo methods typically include the administration of an aromatic-cationic peptide, such as those described above, to a mammal, suitably a human. When used in vivo for therapy, the aromatic-cationic peptides are administered to the subject in effective amounts (i.e., amounts that have desired therapeutic effect). The dose and dosage regimen will depend upon the degree of the injury in the subject, the characteristics of the particular aromatic-cationic peptide used, e.g., its therapeutic index, the subject, and the subject's history.

The effective amount may be determined during preclinical trials and clinical trials by methods familiar to physicians and clinicians. An effective amount of a peptide useful in the methods may be administered to a mammal in need thereof by any of a number of well-known methods for administering pharmaceutical compounds. The peptide may be administered systemically or locally.

The peptide may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt is an acetate salt or a trifluoroacetate salt.

The aromatic-cationic peptides described herein, such as D-Arg-2',6'-Dmt-Lys-Phe-NH$_2$, or pharmaceutically acceptable salts thereof, such as acetate salt or trifluoroacetate salt, can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The aromatic-cationic peptide compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it were preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed my iontophoresis.

A therapeutic protein or peptide can be formulated in a carrier system. The carrier can be a colloidal system. The colloidal system can be a liposome, a phospholipid bilayer vehicle. In one embodiment, the therapeutic peptide is encapsulated in a liposome while maintaining peptide integrity. As one skilled in the art would appreciate, there are a variety of methods to prepare liposomes. (See Lichtenberg et al., *Methods Biochem. Anal.,* 33:337-462 (1988); Anselem et al., *Liposome Technology*, CRC Press (1993)). Liposomal formulations can delay clearance and increase cellular uptake (See Reddy, *Ann. Pharmacother.,* 34(7-8):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic peptide can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. (See Kozarich and Rich, *Chemical Biology*, 2:548-552 (1998)).

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods*, 4(3): 201-9 (1994); and Gregoriadis, "Engineering Liposomes for Drug Delivery: Progress and Problems," *Trends Biotechnol.*, 13(12):527-37 (1995). Mizguchi et al., *Cancer Lett.*, 100: 63-69 (1996), describes the use of fusogenic liposomes to deliver a protein to cells both in vivo and in vitro.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the aromatic-cationic peptides, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.1-10,000 micrograms per kg body weight. In one embodiment, aromatic-cationic peptide concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, and preferably until the subject shows partial or complete amelioration of symptoms of disease. Thereafter, the patient can be administered a prophylactic regime.

In some embodiments, a therapeutically effective amount of an aromatic-cationic peptide may be defined as a concentration of peptide at the target tissue of $10^{-12}$ to $10^{-6}$ molar, e.g., approximately $10^{-7}$ molar. This concentration may be delivered by systemic doses of 0.01 to 100 mg/kg or equivalent dose by body surface area. The schedule of doses would be optimized to maintain the therapeutic concentration at the target tissue, most preferably by single daily or weekly administration, but also including continuous administration (e.g., parenteral infusion or transdermal application).

In some embodiments, the dosage of the aromatic-cationic peptide is provided at a "low," "mid," or "high" dose level. In one embodiment, the low dose is provided from about 0.01 to about 0.5 mg/kg/h, suitably from about 0.0001 to about 0.1 mg/kg/h. In one embodiment, the mid-dose is provided from about 0.001 to about 1.0 mg/kg/h, suitably from about 0.01 to about 0.5 mg/kg/h. In one embodiment, the high dose is provided from about 0.005 to about 10 mg/kg/h, suitably from about 0.01 to about 2 mg/kg/h.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance present methods can be any mammal, including, for example, farm animals, such as sheep, pigs, cows, and horses; pet animals, such as dogs and cats; laboratory animals, such as rats, mice and rabbits. In a suitable embodiment, the mammal is a human.

V. Measurement of Renal Injury Associated Renal Artery Stenosis

Imaging techniques are useful in assessing the effect of the peptides of the present technology on renal reperfusion injury. For example, renal microvasculature architecture may be visualized by CT, micro-CT, or MRI. Alternatively, renal microvasculature architecture may be assessed using methods known in the art that are compatible with the methods described herein. Imaging methods are useful for evaluating the density and tortuosity of renal microvasculature density, as well as average vessel diameter.

Additionally or alternatively, renal reperfusion injury may be evaluated by measuring various parameters of renal function, including, but not limited to, arterial pressure, renal volume, renal blood flow, renal oxygenation, and glomerular filtration rate. Methods for measuring these parameters are known in the art, including, but not limited to blood oxygen level-dependent magnetic resonance imaging (BOLD-MRI), and multidetector computer tomography (MDCT).

Additionally or alternatively, renal reperfusion injury may be assessed by in vitro methods, including, but not limited to, measurement of apoptosis, renal morphology including inflammation and fibrosis, and renal oxidative stress. Apoptosis may be assessed using methods known in the art, such as, for example, detection of DNA fragmentation by terminal deoxynucleotidyl transferase dUTP nick end labeling (TUNEL), detection of caspase activation, and detection of pro-apoptotic proteins such as Bcl-xL and Bax. Renal morphology, including inflammation and fibrosis, may be detected using methods known in the art, including, but not limited to, hematoxylin and eosin (H & E) staining, trichrome staining, and detection of CD163, MMP-9, PAI-1, MCP-1, VEGF, TNF-$\alpha$, TGF-$\beta$, and VEGR1 levels. Oxidative stress may be measured by methods known in the art, including, but not limited to, measurement of isoprostanes, superoxides, NAD(P)H oxidase, DHE, MnCuZn-SOD, NO synthase, heme oxygenase and plasma nitrate/nitrate levels.

EXAMPLES

The present technology further illustrated by the following examples, which should not be construed as limiting in any way.

As noted above, ischemia can result in significant changes in the microvasculature that interferes with normal blood flow to many tissues/organs. As such, ischemia/reperfusion phenomenon can occur in a variety of tissues/organs including heart, liver, brain, skin, skeletal muscle, kidney, etc. It is predicted that the aromatic-cationic peptides of the present technology are useful in methods to prevent or treat ischemia/reperfusion injury in a variety of tissues/organs. It is further predicted that the aromatic-cationic peptides of the present technology are useful in methods for the chronic treatment of ARVD.

Example 1 Reduction of Renal Injury Following Percutaneous Transluminal Renal Angioplasty (PTRA) in Porcine Renal Atherosclerotic Artery Stenosis (ARAS) by Administration of D-Arg-2',6'-Dmt-Lys-Phe-NH$_2$ A. Summary This example demonstrates use of the aromatic-cationic peptide D-Arg-2',6'-Dmt-Lys-Phe-NH$_2$ in the prevention and treatment of renal injury associated with renal atherosclerotic artery stenosis (ARAS). According to the present methods, animal subjects were subjected to a period of ARAS followed by renal revascularization by percutaneous transluminal renal angioplasty (PTRA). Subjects were administered aromatic-cationic peptide in conjunction with PTRA, including defined time periods before and after the revascularization procedure. Control animals received either no infusion, or infusion of control vehicle alone. Multiple aspects of renal function were improved in subjects receiving the peptide as compared to control subjects, including renal volume, renal blood flow, glomerular filtration rate, renal microvasculature density, average vessel diameter, vessel tortuosity, and renal oxygenation. Administration of the peptide also reduced early renal inflammation, apoptosis, fibrosis, and oxidative stress. The results demonstrate that the peptide D-Arg-2',6'-Dmt-Lys-Phe-NH$_2$ is useful in methods for treating or preventing renal injury associated with revascularization by PTRA in the treatment of ARAS.

B. Overview of Experimental Design

A summary of the experimental timeline is shown in FIGS. 16A-16D and FIG. 1. All experiments were performed in accordance with guidelines and approved by the Institutional Animal Care and Use Committee (IACUC). Subjects comprised domestic juvenile female subjects (Manthei Hog Farm, LLC, MN) during 16 weeks of observation (FIG. 1). At baseline, animals were randomized in either normal (n=7) or ARAS (n=21) groups. Normal animals were fed normal pig chow, and ARAS subjects a high-cholesterol diet (TD-93296, Harlan-Teklad, Indianapolis, Ind., USA), which induces diffuse early-atherosclerosis, characterized by elevated cholesterol levels and renal functional compromise, inflammation and fibrosis in the RAS kidney, as previously shown. See Table 7.

After a period of six weeks, ARAS subjects underwent unilateral RAS, induced by placing a local-irritant coil in the main renal artery, while normal animals were sham-operated. For anesthesia, animals were induced with an intramuscular injection of ketamine and xylazine (0.5 g), and anesthesia was maintained with intravenous ketamine (0.2 mg/kg/min) and xylazine (0.03 mg/kg/min). A telemetry system (Data Sciences International, St Paul, Minn., USA) was implanted in the left femoral artery to continuously measure mean arterial pressure (MAP) for the 10 following weeks.

Six weeks after induction of RAS, animals were similarly anesthetized, the degree of stenosis determined by angiography, and subjects were treated with PTRA or sham. Heating pads maintained the animal's body temperature by about 37° C. during surgery, and PTRA and stenting performed under fluoroscopic guidance, as previously described. In addition, ARAS subjects were treated with a continuous intravenous infusion of peptide 0.050 mg/kg or an equal volume of saline vehicle from 30 min before to 3.5 hrs after PTRA or sham. Inferior vena cava (IVC) samples were collected for pharmacokinetic analysis as well as for inflammatory and injury biomarkers at baseline (immediately before peptide infusion), 30 minutes post-reperfusion, and 180 minutes post-reperfusion. Urinary samples were collected before peptide infusion and 210 min after PTRA.

Four weeks later, the subjects were again similarly anesthetized and the degree of stenosis determined by angiography. IVC samples were collected for PRA, creatinine, and cholesterol measurements. Urine samples were collected to quantify albumin concentration (ELISA, Bethyl Laboratories, Texas). Renal hemodynamics and function in each kidney were assessed using multi-detector computer tomography (MDCT).

TABLE 7

Overview of Experimental Design

| Group | Treatment |
|---|---|
| ARAS + PTRA + vehicle (vehicle control) | High cholesterol diet + RAS + PTRA + saline |
| ARAS + PTRA + D-Arg-2',6'-Dmt-Lys-Phe-NH$_2$ | High cholesterol diet + RAS + PTRA + D-Arg-2',6'-Dmt-Lys-Phe-NH$_2$ |
| Normal | Normal diet + sham |
| Normal + D-Arg-2',6'-Dmt-Lys-Phe-NH$_2$ | Normal diet + sham + D-Arg-2',6'-Dmt-Lys-Phe-NH$_2$ |
| ARAS + PTRA (non-infusion control) | High cholesterol diet + RAS + PTRA |
| Normal (non-infusion control) | Normal diet |

Three days after the completion of the in-vivo studies, animals were euthanized with sodium pentobarbital (100 mg/kg, Sleepaway®, Fort Dodge Laboratories, Fort Dodge, Iowa, USA). The kidneys were removed, dissected, and prepared for ex-vivo studies. Renal arteries from normal animals were harvested, and isolated rings suspended in organ chambers filled with Kreb's solution to evaluate vascular reactivity in response to peptide. Mitochondrial biogenesis, microvascular architecture, apoptosis, angiogenesis, inflammation, oxidative stress, tubular injury, and fibrosis were evaluated ex-vivo.

MDCT studies were performed for assessment of single-kidney renal hemodynamics and function. Following a central venous injection of iopamidol (0.5 mL/kg per 2 seconds), 140 consecutive scans were performed. Cross-sectional images were reconstructed, and analyzed with the Analyze™ software package (Biomedical Imaging Resource, Mayo Clinic, Rochester, Minn.). Cortical and medullary volume and perfusion, RBF, and GFR were calculated, as described in detail previously.

C. Methods

Pharmacokinetic Analysis 4 mL venous whole blood samples were collected from peptide-treated animals at baseline (immediately before peptide infusion), immediately before PTRA, and 30 and 180 min post-reperfusion. Venous blood were drawn using syringes into BD Vacutainer® PST™ Plasma Separation Tubes (lavender top) containing K2EDTA, 10 mL/tube. Tubes were gently inverted 8 times and kept in an ice water bath until centrifugation. Within an hour samples were centrifuged in a swing bucket centrifuge at 1000-1300 RCF (or approximately 1500×G) for 15 min at 4° C. Plasma were harvested from individual blood tubes, placed in a single polypropylene vials (or screw-cap tubes) and stored at approximately −80° C. until assay.

The plasma concentration of D-Arg-2',6'-Dmt-Lys-Phe-NH$_2$ was determined using a qualified LC/MS/MS assay in K2-EDTA pig plasma. The assay employed deuterium labeled d$_5$-D-Arg-2',6'-Dmt-Lys-Phe-NH$_2$ as the analytical internal standard (IS). In brief, samples were spiked with internal standard, processed by protein precipitation extraction (recovery approximately 90%), and analyzed using reversed-phase HPLC with Turbo Ion Spray®MS/MS detection. Positive (M+2H)$^{2+}$ ions for D-Arg-2',6'-Dmt-Lys-Phe-NH$_2$ and the IS (d$_5$-D-Arg-2',6'-Dmt-Lys-Phe-NH$_2$) were monitored in MRM mode. Drug-to-IS peak area ratios for the standards were used to create a linear calibration curve ranging from 2.5 to 1000 ng/mL. The inter-day coefficient of variation for assay precision was less than 10%, and the accuracy ranged from 3.6 to 11.8%.

Inflammatory and Injury Markers

IVC levels of tumor necrosis factor-α (TNF-α) (Invitrogen, Cat #KSC3011), interleukin-1β (IL-1β) (R&D systems DY681), monocyte chemoattractant protein (MCP-1) (Kingfisher Biotech, Cat #VS0081S-002), granulocyte colony-stimulating factor (G-CSF) (NovaTein Bio. Cat #BG-POR11157), and transforming growth factor-β (TGF-β) were measured by Enzyme-linked immunosorbent assay (ELISA) at baseline (before peptide infusion) and 30 min and 180 min after PTRA. Similarly, serum creatinine levels (baseline, 30 min, and 180 min post PTRA) as well as urinary levels of 8-epi-isoprostane, and proteins were measured by standard procedures at baseline and 210 min after PTRA.

Vascular Reactivity

Vasoconstrictor and vasodilator responses to peptide (or vehicle) were evaluated in dissected renal artery sections from normal animal, suspended in organ chambers filled with Kreb's solution, as previously described. Dissected renal artery sections (2-3 mm long, 2 per animal) were suspended in 25 ml organ chambers filled with Kreb's solution at 37° C. (pH=7.4, 95% O$_2$ and 5% CO$_2$). Isometric force was measured by suspending renal artery sections using 2 stainless clips passed through their lumen attached to a stationary post and a strain gauge. By using potassium chloride (KCl, 20 mM) vessel rings were progressively stretched to achieve the optimal point for their length-tension relationship.

Once optimal tension was determined vessel rings were allowed to equilibrate for 30 minutes after washing with control solution. In 4 vessel rings, increasing doses of peptide ($10^{-9}$ M to $10^{-4}$) were administered to test for the presence of vasoconstrictor response. In the other 4 rings, increasing doses of peptide were administered following precontraction with endothelin-1 (10 M) (Phoenix Pharmaceuticals, Mountain View, Calif., USA), to evaluate endothelial relaxation. Data was quantified using WinDaq Acquisition Software (DATAQ Instruments, Inc. Akron, Ohio, USA).

Apoptosis and Mitochondrial Biogenesis

Apoptosis was assessed in renal tissue sections stained with TUNEL (Promega, Madison, Wis., USA) and caspase-3 (1:200, Santa Cruz Biotechnology, Santa Cruz, Calif., USA). In addition, renal protein expression of the apoptosis staining regulator proteins Bcl-2 (Lifespan BioSciences, Seattle, Wash., USA; 1:1000) and Bax (Santa Cruz Biotechnology, 1:200) was evaluated by Western blot.

Mitochondrial biogenesis was evaluated by renal expression of PGC-1α (Abeam, 1:1000), NRF-1 (Abeam, Cambridge, Mass., USA; 1:300), GABP (Abeam, 1:1000), PPAR-α (Abeam, 1:1000), PPAR-6 (Abeam, 1:300), HO-1 (Abeam, 1:250), and SIRT-1 (Abeam, 1:1000).

Microvascular Architecture and Angiogenesis

To evaluate microvascular architecture, kidneys were perfused under physiologic perfusion pressure with a radio-opaque silicone polymer (Microfil MV122; Flow Tech, Carver, Mass., USA). Perfused kidney sections were scanned using a micro-CT scanner, and reconstructed images (18 μm voxels) displayed using Analyze™. Spatial density, average diameter, and tortuosity of renal cortical microvessels (diameters of 40-500 μm) were calculated, as previously described. In addition, renal protein expression of VEGF and its receptors (VEGFR-1 and 2) (Santa Cruz Biotechnology; 1:200) was measured by western blot.

Renal Morphology and Fibrosis

Renal fibrosis was assessed in 5 μm mid-hilar cross-sections of each kidney stained with Masson's trichrome by using the computer-aided image-analysis program AxioVision® 4.8.2.0 (Carl ZEISS SMT, Oberkochen, Germany). Tubulo-interstitial fibrosis and glomerular score (% of sclerotic out of 100 glomeruli) were quantified in 15-20 fields. In addition, tubular injury was scored in a blinded fashion in sections stained with Periodic acid-Schiff (PAS). Briefly, tubular injury (dilation, atrophy, cast formation, cell detachment, or thickening of tubular basement membrane) was scored from 1 to 5, 0 being normal tubules, 1: <10% of tubules injured, 2: 10-25% of tubules injured, 3: 26-50% of tubules injured, 4: 51-75% of tubules injured, 5: >75% of tubules injured.

Inflammation and Oxidative Stress

Renal inflammation was assessed in tissue sections stained with MCP-1 or CD163 (quantification of renal macrophages), and by protein expression of TNF-α (Santa Cruz Biotechnology; 1:200) measured by Western blot.

Oxidative stress was assessed by dihydroethidium (DHE) staining of kidney tissue, systemic levels of 8-epi-isoprostane (EIA kit), renal protein expression of the NADPH-oxidase sub-unit p47 (Santa Cruz 1:200), and nitrotyrosine (Cayman Chemical Co., Ann Arbor, Mich., USA; 1:200).

Statistical Methods

All data were analyzed using JMP software package version 8.0 (SAS Institute Inc., Cary, N.C., USA). The Shapiro-Wilk test was used to test for deviation from normality. Results were expressed as mean±standard deviation (SD) for normally distributed data, and medium (range) for non-normally distributed data. Parametric (ANOVA and unpaired Student t-test) and non-parametric (Wilcoxon and Kruskal Wallis) tests were used as appropriate. Values of $p<0.05$ were considered statistically significant.

D. Results

Induction and Alleviation of RAS

Figure 3A:
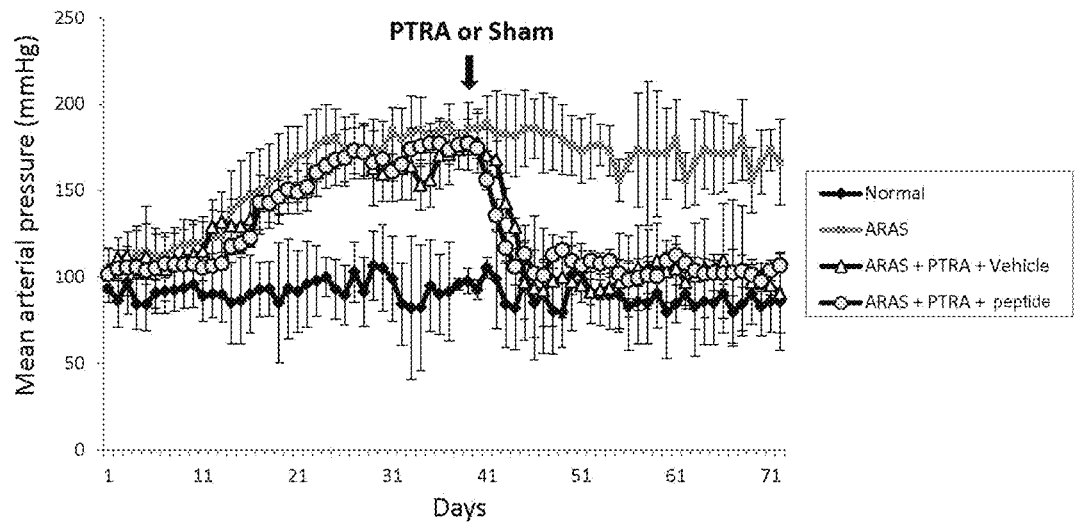
FIG. 3A is a chart showing mean arterial pressure in experimental subjects over a period of 71 days, as measured by telemetry.

Six weeks after the induction of RAS and before revascularization, significant degrees of stenosis were achieved in all ARAS animals (77.5% (65-95%)), and mean arterial pressure (MAP) was similarly elevated ($p<0.05$ vs. normal) (FIG. 3A).

Circulating Levels of Peptide and Injury Signals During PTRA

Systemic plasma peptide concentration increased to therapeutic levels (~100 ng/mL) by 30 min after infusion, and subsequently reached an apparent steady state concentration at 60-90 minutes post infusion, throughout the end of infusion (Table 8).

Figure 1B:
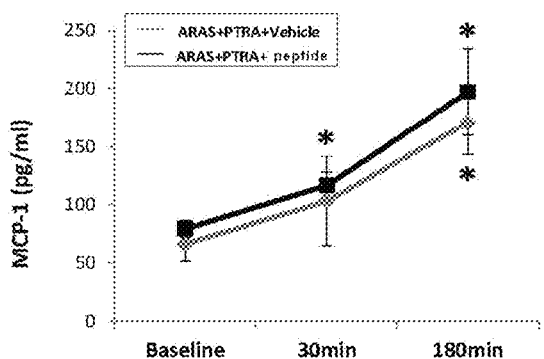
FIG. 1B-G are charts showing inferior vena cava levels of monocyte chemoattractant protein (MCP-1) (B), tumor necrosis factor (TNF)-α (C), interleukin (IL)-1β (D), granulocyte colony-stimulating factor (G-CSF) (E), transforming growth factor (TGF)-β (F), and serum creatinine (Scr) (G) in ARAS+PTRA+vehicle and ARAS+PTRA+D-Arg-2',6'-Dmt-Lys-Phe-NH$_2$ peptide pigs at baseline (before peptide infusion), 30 minutes post-PTRA, and 180 min post-PTRA. *$p<0.05$ vs. Baseline; #$p<0.05$ vs. ARAS+PTRA+vehicle.
Figure 1C:
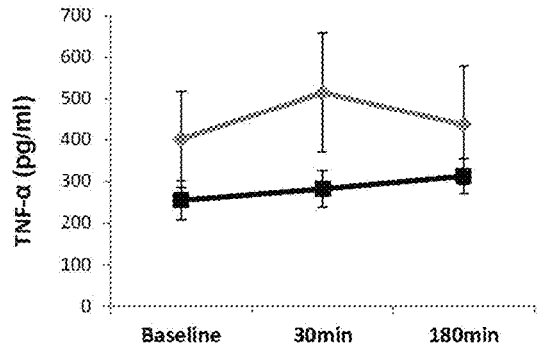
Figure 1D:
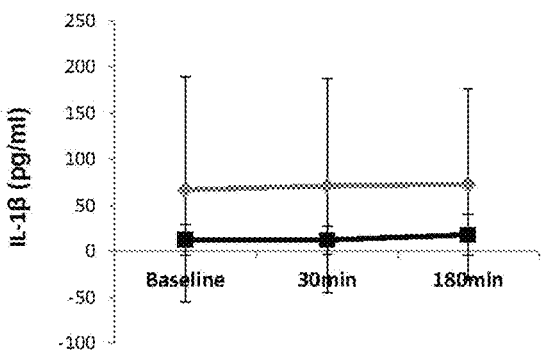
Figure 1E:
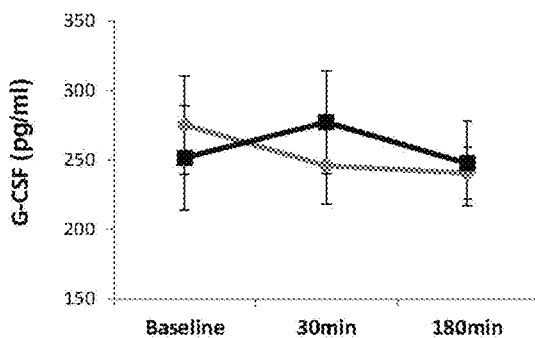
Figure 1F:
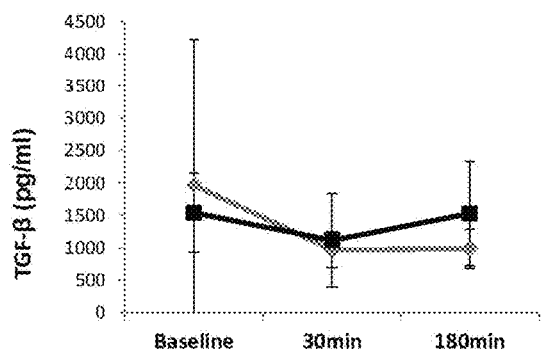
Figure 1G:
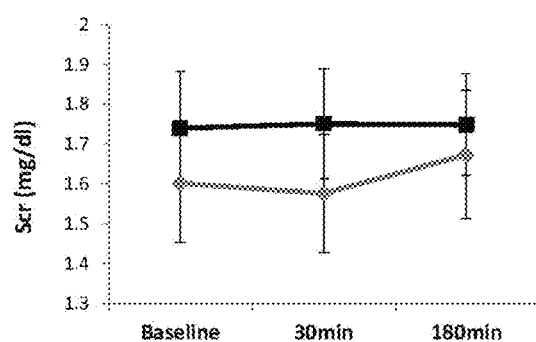
Figure 2A:
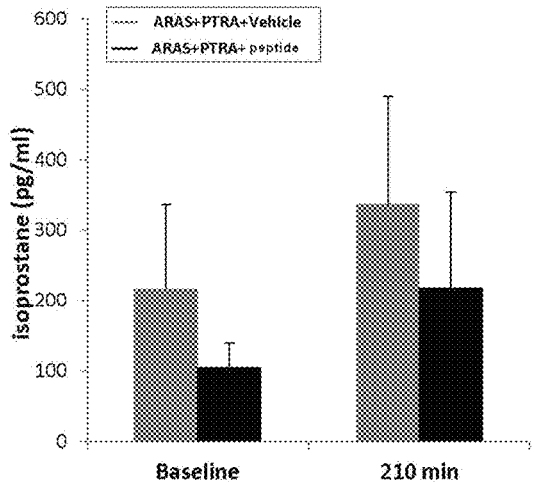
FIG. 2A-B are charts showing urinary levels of 8-isoprostane (A) and urinary proteins (B) at baseline and 210 min after PTRA in ARAS+PTRA+vehicle and ARAS+PTRA+D-Arg-2',6'-Dmt-Lys-Phe-NH$_2$ peptide subjects. #$p<0.05$ vs. ARAS+PTRA+vehicle.
Figure 2B:
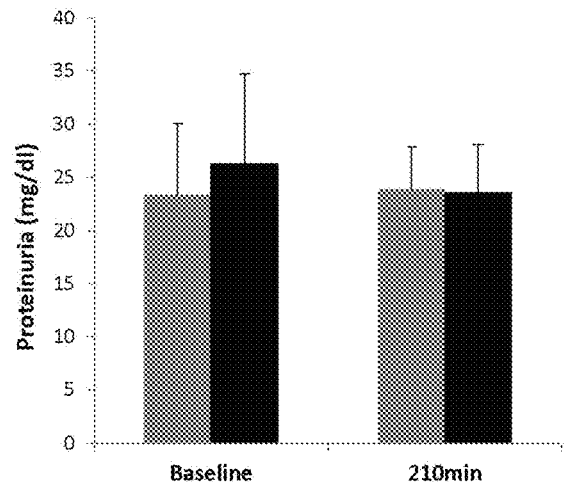

Systemic plasma levels of monocyte chemoattractant protein (MCP-1) similarly increased after revascularization in ARAS+PTRA+vehicle and ARAS+PTRA+peptide animals (FIG. 1B, both $p<0.05$ vs. baseline). Systemic levels of tumor necrosis factor (TNF)-α, interleukin (IL)-1β, granulocyte colony-stimulating factor (G-CSF), transforming growth factor (TGF)-β, and creatinine remained unchanged after revascularization (FIG. 1C-G), as did urinary protein and 8-epi-isoprostane levels (FIG. 2A-B).

Pharmacokinetic Analysis

Peptide IV infusion started at 30 minutes prior to the PTRA procedure and continued for 210 minutes at 0.05 mg/kg/h. Mean plasma concentration at 30 minutes into infusion (i.e. time of PTRA procedure) was 100.6 ng/mL (Table 8). Plasma concentration continued to increase, reached an apparent steady state concentration (~125 ng/mL) at approximately 60-90 minutes, and maintained a steady state level through end of infusion.

TABLE 8

Mean plasma D-Arg-2',6'-Dmt-Lys-Phe-NH$_2$ concentration during a 3.5-h IV infusion (0.05 mg/kg/h) in a porcine model of atherosclerotic renal artery stenosis.

| Time from PTRA (min) | Time from peptide Infusion (min) | Mean peptide Concentration (ng/ml) |
|---|---|---|
| −30 | 0 | BQL |
| PTRA | 30 | 100.6 ± 36.2 |
| 30 | 60 | 118.4 ± 23.7 |
| 60 | 90 | 125.1 ± 21.4 |
| 180 | 210 | 111.3 ± 42.0 |

PTRA: percutaneous transluminal renal angioplasty; BQL: below quantifiable limit (2.5 ng/mL)
NA: not applicable.

Vascular Reactivity

Figure 2C:
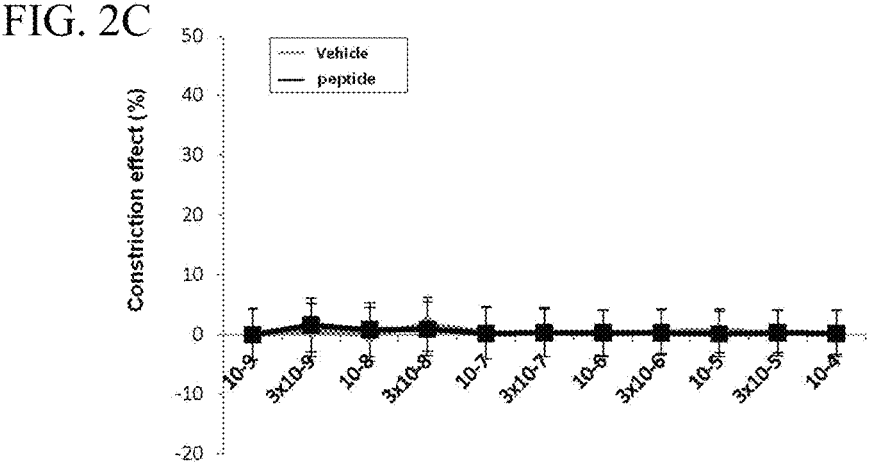
FIGS. 2C and 2D are charts illustrating that neither vasoconstrictor (C) nor vasodilator (D) effects were observed in isolated renal artery rings in response to peptide. #$p<0.05$ vs. ARAS+PTRA+vehicle.
Figure 2D:
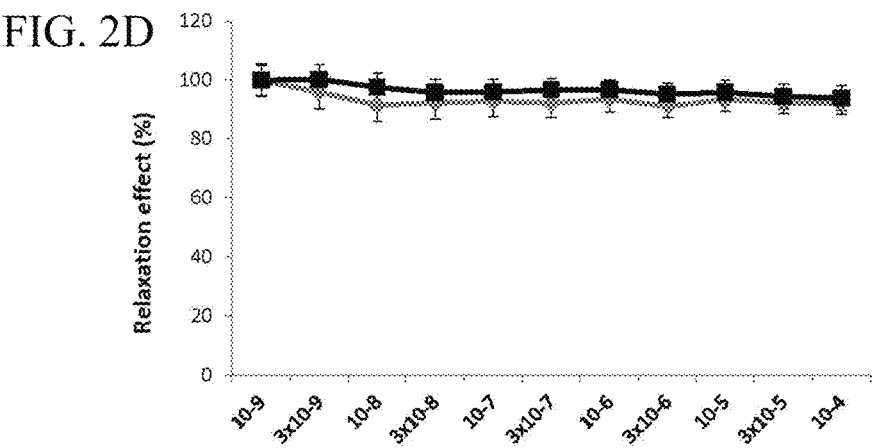

Isolated renal artery rings exposed to increasing doses of D-Arg-2',6'-Dmt-Lys-Phe-NH$_2$ showed no change in diameter (FIG. 2C-D). This results suggests that the peptide does not induce vasoconstriction nor vasodilation.

Renal Function and Structure Four Weeks after PTRA

Figure 3B:
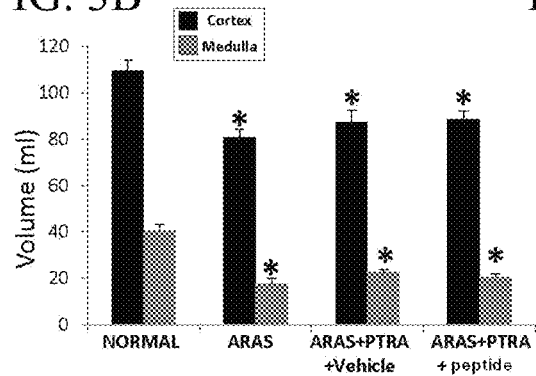
FIG. 3B-E show renal cortical (black) and medullary (gray) volume (B), perfusion (C), renal blood flow (RBF) (D), and glomerular filtration rate (GFR) (E) in normal, ARAS, ARAS+PTRA+vehicle, and ARAS+PTRA+D-Arg-2',6'-Dmt-Lys-Phe-NH$_2$ peptide subjects. Administration of peptide improved renal function in the stenotic revascularized kidney. *$p<0.05$ vs. Normal; ‡$p<0.05$ vs. ARAS+PTRA+D-Arg-2',6'-Dmt-Lys-Phe-NH$_2$ peptide.

Table 9 shows systemic parameters in all groups 4 weeks after PTRA or sham. No residual stenosis was observed in PTRA-treated animals, and MAP decreased to normal levels (FIG. 3B). Serum creatinine levels were elevated in all ARAS compared to normal (all $p<0.05$ vs. normal), but plasma renin activity (PRA) and urinary albumin levels were similar to normal subjects. Total cholesterol levels, high-density lipoprotein (HDL), and low-density lipoprotein (LDL) were higher in all ARAS compared to normal.

D-Arg-2',6'-Dmt-Lys-Phe-NH$_2$ Improved Renal Hemodynamics and Function

Figure 3C:
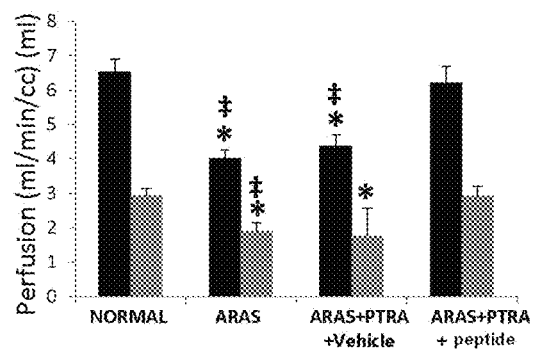
Figure 3D:
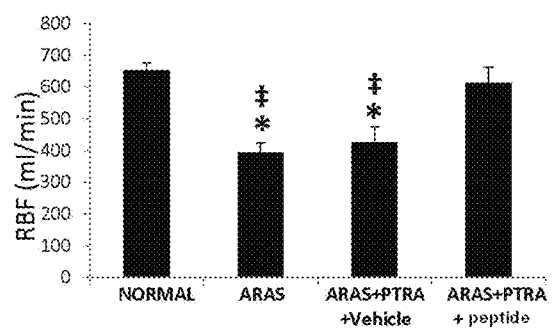
Figure 3E:
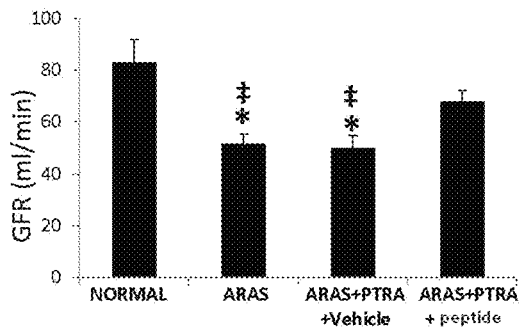

Four weeks after revascularization, cortical and medullary volumes were similarly lower in all ARAS compared to normal animals (FIG. 3B). In contrast, cortical and medullary perfusion, RBF, and GFR that were significantly reduced in ARAS and unchanged by PTRA alone, were restored to normal levels in peptide-treated subjects (FIG. 3C-E, all $p>0.05$ vs. normal).

Figure 4A:
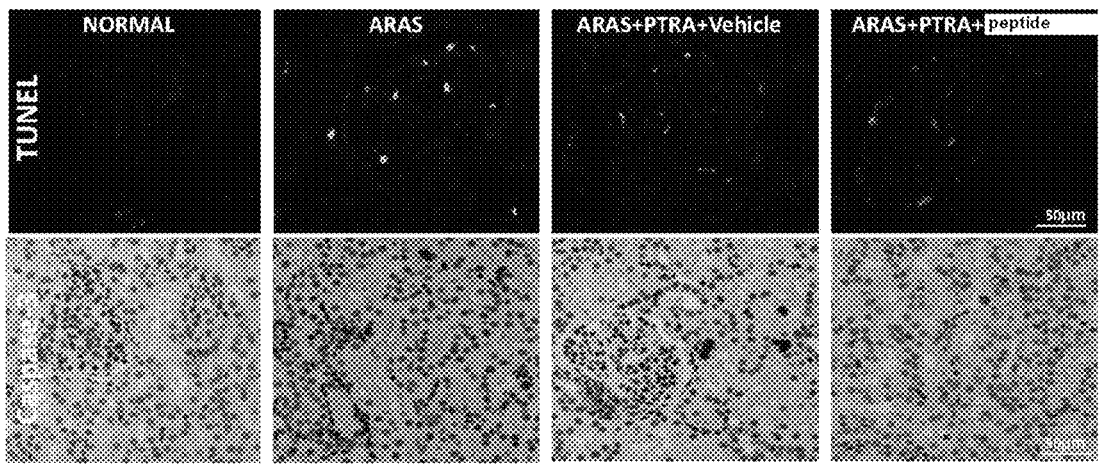
FIG. 4A shows representative terminal deoxynucleotidyl transferase dUTP nick end labeling (TUNEL) (upper panels) and caspase-3 staining (lower panels) in normal, ARAS, ARAS+PTRA+vehicle, and ARAS+PTRA+D-Arg-2',6'-Dmt-Lys-Phe-NH$_2$ peptide subjects.
Figure 4B:
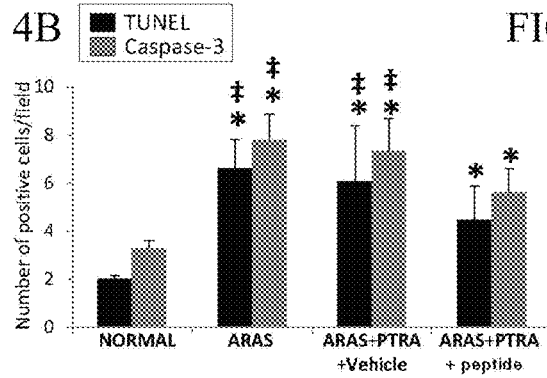
FIG. 4B shows quantification of TUNEL (black) and caspase-3 staining (gray) in normal, ARAS, ARAS+PTRA+vehicle, and ARAS+PTRA+D-Arg-2',6'-Dmt-Lys-Phe-NH$_2$ peptide subjects.

D-Arg-2',6'-Dmt-Lys-Phe-NH$_2$ Decreased Apoptosis and Promoted Mitochondrial Biogenesis The number of apoptotic cells positive for terminal deoxynucleotidyl transferase dUTP nick end labeling (TUNEL) and caspase-3 was elevated in ARAS and ARAS+PTRA+Vehicle compared to normal, but decreased in ARAS+PTRA+peptide subjects (FIG. 4A-B). Renal expression of B-cell lymphoma (Bcl)-2 did not differ among the groups, but treatment with peptide during PTRA significantly reduced the subsequent expression of the pro-apoptotic protein Bcl-2-associated X protein (Bax, FIG. 4C-D).

Figure 4C:
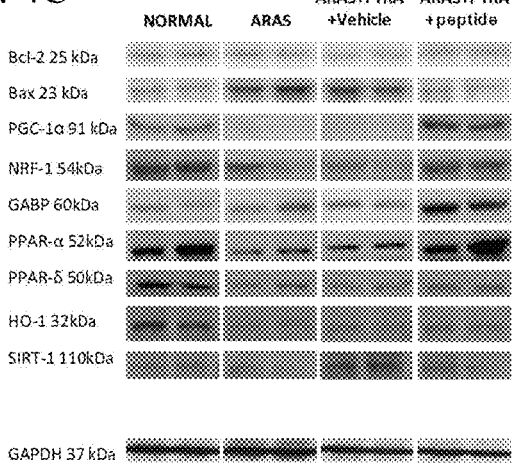
FIG. 4C is a western blot showing expression of B-cell lymphoma (Bcl)-2, Bcl-2-associated X protein (Bax), peroxisome proliferator-activated receptors gamma co-activator (PGC)-1α, nuclear respiratory factor (NRF)-1, GA-binding protein (GABP), peroxisome proliferator-activated receptor (PPAR) α, PPAR-δ, Heme oxygenase (HO)-1, and sirtuin (SIRT)-1 in renal tissue from normal, ARAS, ARAS+PTRA+vehicle, and ARAS+PTRA+D-Arg-2',6'-Dmt-Lys-Phe-NH$_2$ peptide subjects.
Figure 4D:
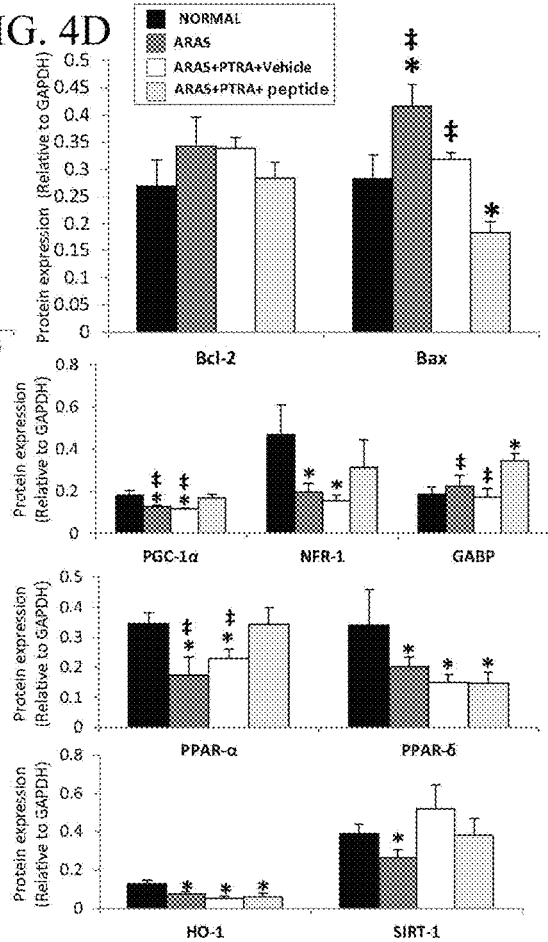
FIG. 4D shows the quantification of these proteins relative to GAPDH.

D-Arg-2',6'-Dmt-Lys-Phe-NH$_2$ also up-regulated the expression of PGC-1α, nuclear respiratory factor (NRF)-1, GA-binding protein (GABP), and peroxisome proliferator-activated receptor (PPAR)-α (FIG. 4C-D). Renal expression of Heme oxygenase (HO)-1 and PPAR-δ remained similarly blunted in all ARAS groups. Revascularization (with or without adjunct peptide) restored the down-regulated expression of sirtuin (SIRT)-1 observed in ARAS to normal levels (FIG. 4C-D, $p>0.05$ vs. normal).

D-Arg-2',6'-Dmt-Lys-Phe-NH$_2$ Improved the Microvascular Network

Figure 5A:
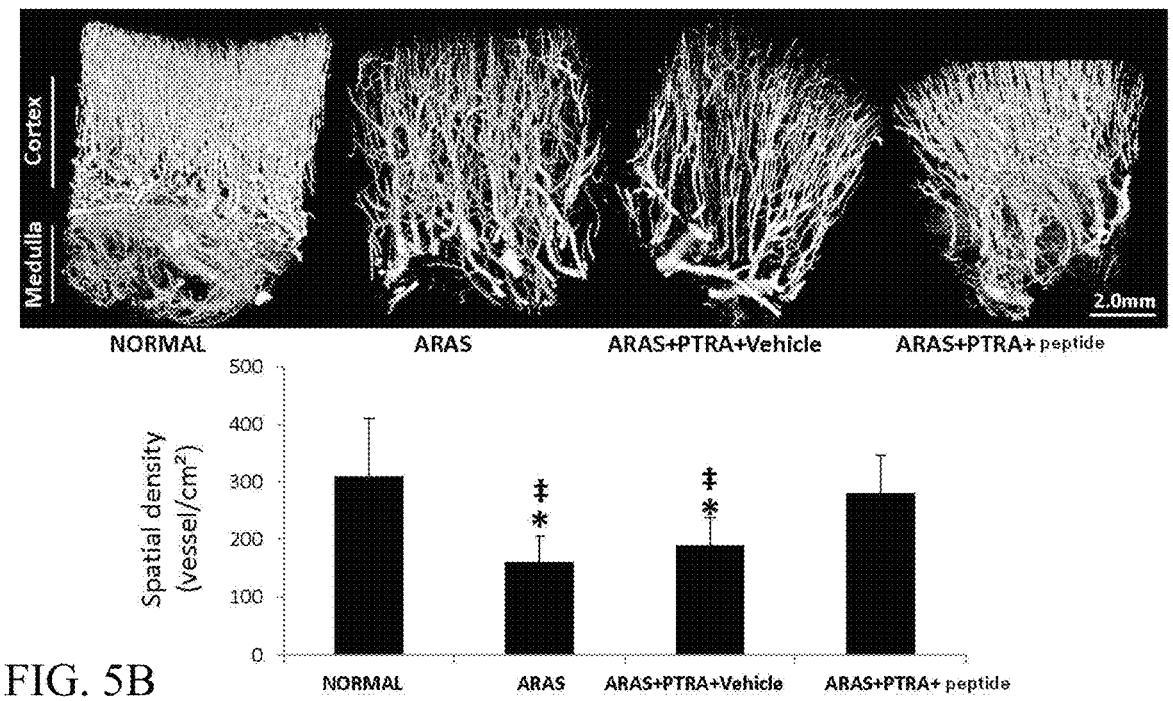
FIG. 5A shows representative three-dimensional micro-CT images in normal, ARAS, ARAS+PTRA+vehicle, and ARAS+PTRA+D-Arg-2',6'-Dmt-Lys-Phe-NH$_2$ peptide subjects (upper panel) and quantification of transmural spatial density of cortical microvessels (lower panel).
Figure 5B:
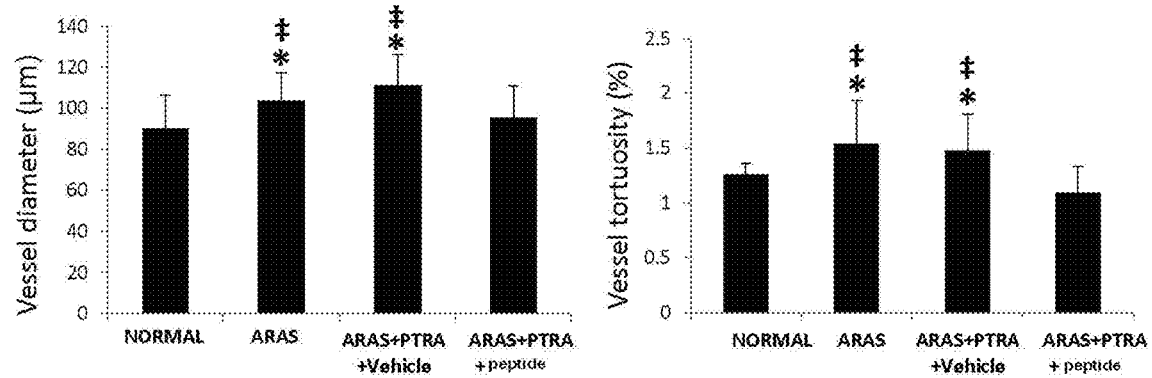
FIG. 5B shows the quantification of average vessel diameter and vessel tortuosity of cortical microvessels.
Figure 5C:
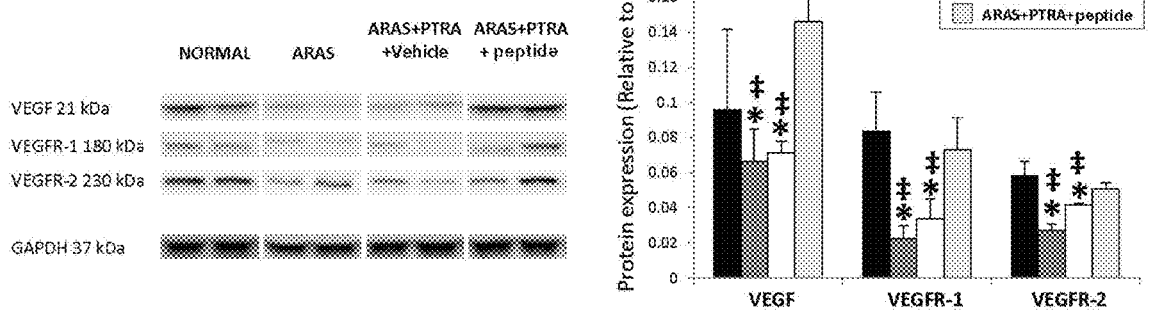
FIG. 5C shows levels of renal expression of vascular endothelial growth factor (VEGF) and its receptors (VEGFR-1 and VEGFR2) in normal, ARAS, ARAS+PTRA+vehicle, and ARAS+PTRA+D-Arg-2',6'-Dmt-Lys-Phe-NH$_2$ peptide subjects. *$p<0.05$ vs. Normal; ‡$p<0.05$ vs. ARAS+PTRA+D-Arg-2',6'-Dmt-Lys-Phe-NH$_2$ peptide.

Spatial density of renal cortical microvessels was similarly low in ARAS and ARAS+PTRA+Vehicle animals, but did not differ from normal levels in subjects treated with peptide during PTRA (FIG. 5A). In addition, average vessel diameter and tortuosity were similarly increased in ARAS and ARAS+PTRA+Vehicle, but improved in peptide-treated subjects (FIG. 5B). Renal expression of VEGF and its receptors (VEGFR-1 and 2) were lower in ARAS compared to normal, and remained reduced in animals treated with PTRA+Vehicle. However, treatment with PTRA+peptide restored them to levels similar to (VEGFR-1 and VEGFR-2) or above (VEGF) normal (FIG. 5C).

Figure 6A:
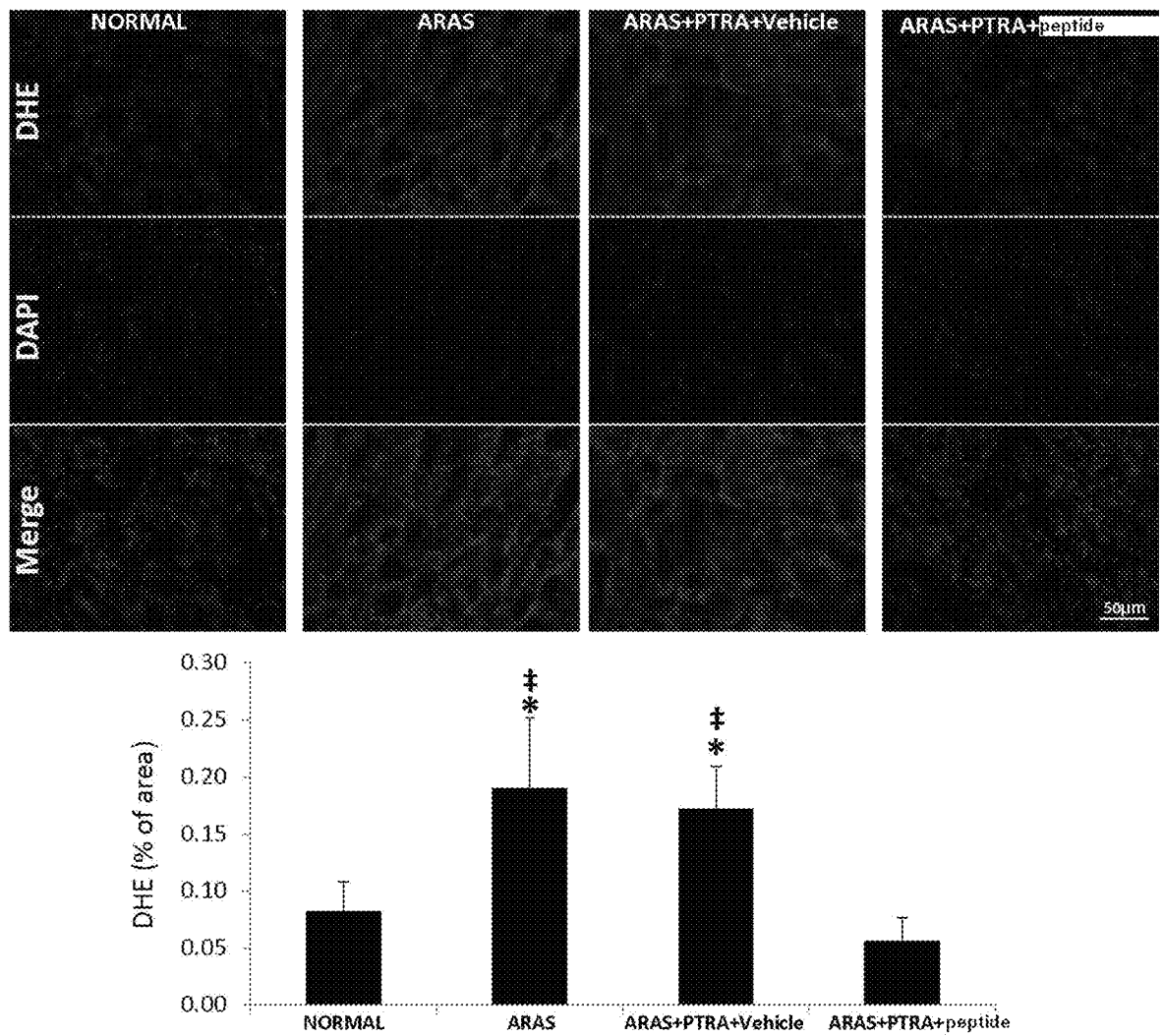
FIG. 6A shows fluorescent dihydroethidium (DHE) and DAPI staining in renal tissues from normal, ARAS, ARAS+PTRA+vehicle, and ARAS+PTRA+D-Arg-2',6'-Dmt-Lys-Phe-NH$_2$ peptide subjects (upper panels) and quantification of the signals (lower panel).
Figure 6B:
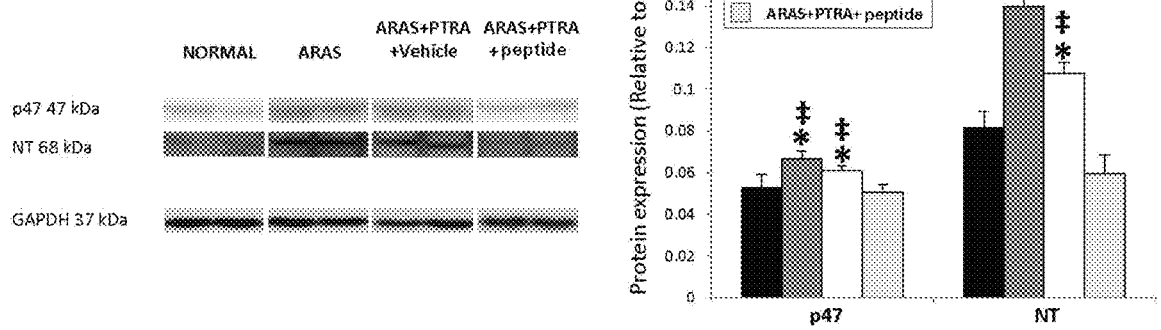
FIG. 6B shows levels of p47 and nitrotyrosine (NT) in renal tissues from normal, ARAS, ARAS+PTRA+vehicle, and ARAS+PTRA+D-Arg-2',6'-Dmt-Lys-Phe-NH$_2$ peptide subjects. *$p<0.05$ vs. Normal; ‡$p<0.05$ vs. ARAS+PTRA+D-Arg-2',6'-Dmt-Lys-Phe-NH$_2$ peptide.

Oxidative Stress Diminished in Animals Treated with D-Arg-2',6'-Dmt-Lys-Phe-NH$_2$ Systemic levels of 8-epi-isoprostane were elevated in ARAS and ARAS+PTRA+Vehicle compared to normal, but decreased to normal levels in ARAS+PTRA+peptide subjects (Table 9, $p>0.05$ vs. normal). Similarly, in-situ production of superoxide anion in the post-stenotic kidney was significantly increased in ARAS and ARAS+PTRA+Vehicle, but decreased to levels not different from normal in animals treated with peptide (FIG. 6A) as did renal expression of p47 and nitrotyrosine (FIG. 6B, both $p>0.05$ vs. normal).

Inflammation Was Abolished in Peptide-Treated Subjects

Figure 7A:
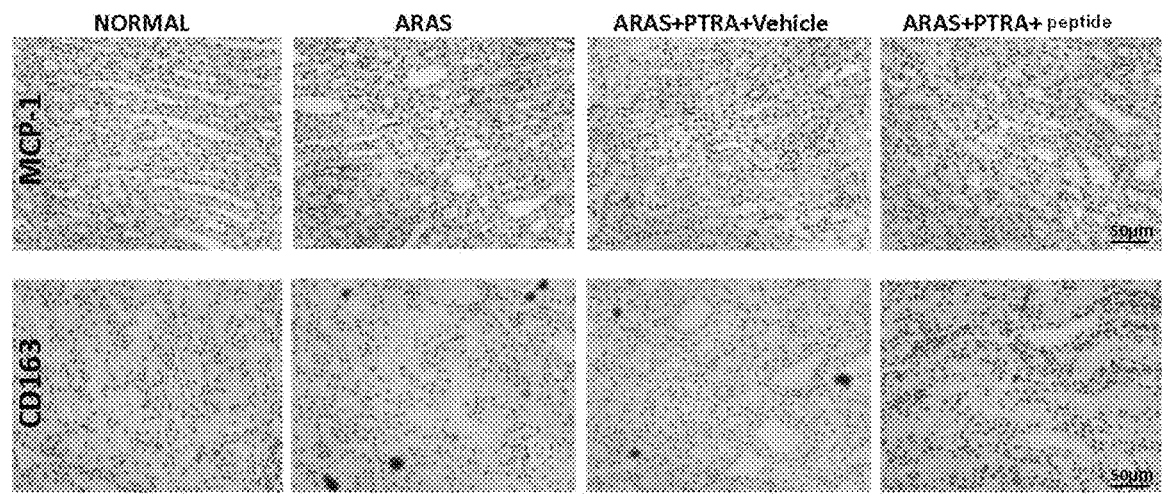
FIG. 7A shows representative MCP-1 (upper panels) and CD163 (lower panels) staining in renal tissue from normal, ARAS, ARAS+PTRA+vehicle, and ARAS+PTRA+D-Arg-2',6'-Dmt-Lys-Phe-NH$_2$ peptide subjects.
Figure 7B:
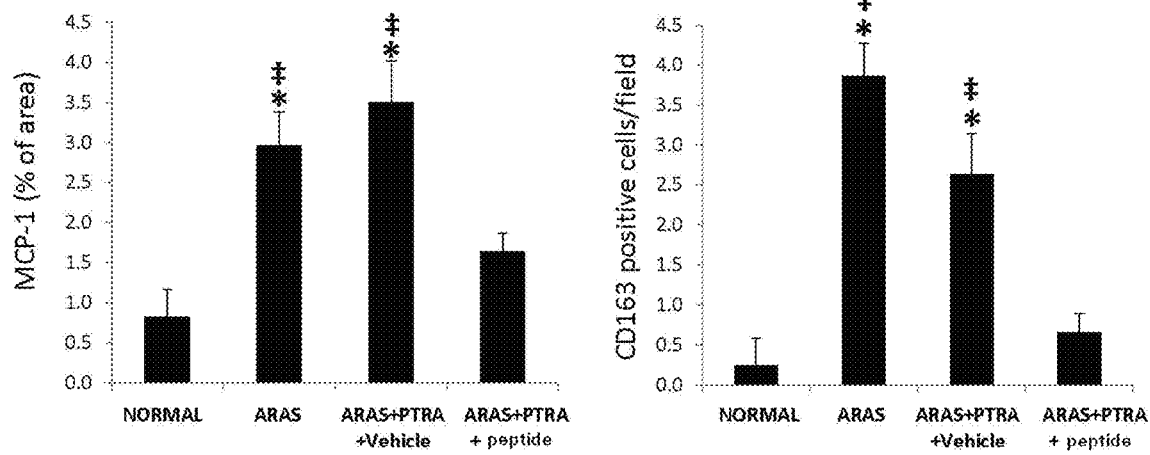
FIG. 7B shows the quantification of MCP-1 and CD163 in renal tissue from normal, ARAS, ARAS+PTRA+vehicle, and ARAS+PTRA+D-Arg-2',6'-Dmt-Lys-Phe-NH$_2$ peptide subjects.
Figure 7C:
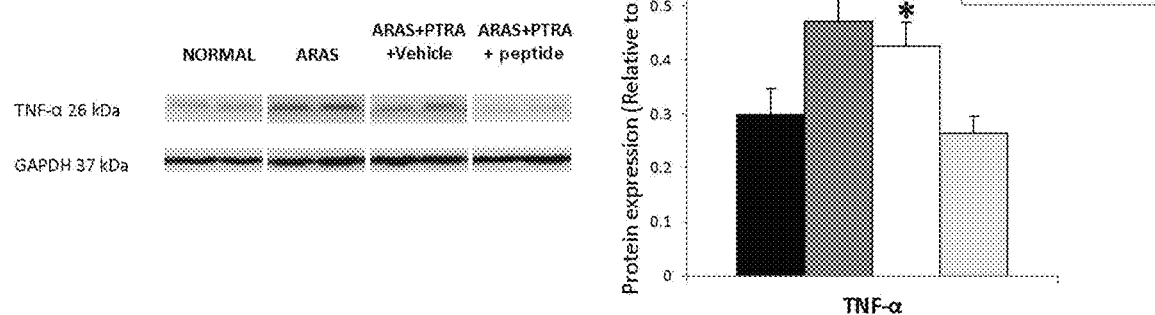
FIG. 7C shows a western blot of TNF-α from renal tissue from normal, ARAS, ARAS+PTRA+vehicle, and ARAS+PTRA+D-Arg-2',6'-Dmt-Lys-Phe-NH$_2$ peptide subjects, and the quantification of TNF-α levels relative to GAPDH. *$p<0.05$ vs. Normal; ‡$p<0.05$ vs. ARAS+PTRA+D-Arg-2',6'-Dmt-Lys-Phe-NH$_2$ peptide.

MCP-1 immunoreactivity was equally up-regulated in ARAS and ARAS+PTRA+Vehicle, but was ameliorated in subjects treated with peptide, as did the number of CD163+ macrophages infiltrating the kidney (FIG. 7A-B). Similarly, elevated renal expression of TNF-α was normalized only in peptide-treated subjects (FIG. 7C).

Inflammatory and Injury Markers During PTRA

Plasma levels of monocyte chemoattractant protein (MCP-1) similarly increased after revascularization in ARAS+PTRA+Vehicle and ARAS+PTRA+peptide animals (FIG. 1B, both $p<0.05$ vs. baseline). However, plasma levels of tumor necrosis factor (TNF)-α, interleukin (IL)-1β, granulocyte colony-stimulating factor (G-CSF), transforming growth factor (TGF)-β, or serum creatinine levels did not change immediately after revascularization (FIG. 1C-G).

Proteinuria as well as urinary levels of 8-isoprostanes and TGF-β remained unchanged after PTRA (FIG. 2A-B).

Treatment with Peptide Decreased Tubular Damage and Renal Scarring

Tubular injury score was higher than normal in all ARAS groups ($p<0.05$ all), but significantly diminished, although not abolished, in ARAS+PTRA+peptide subjects (FIG. 8A).

Figure 9A:
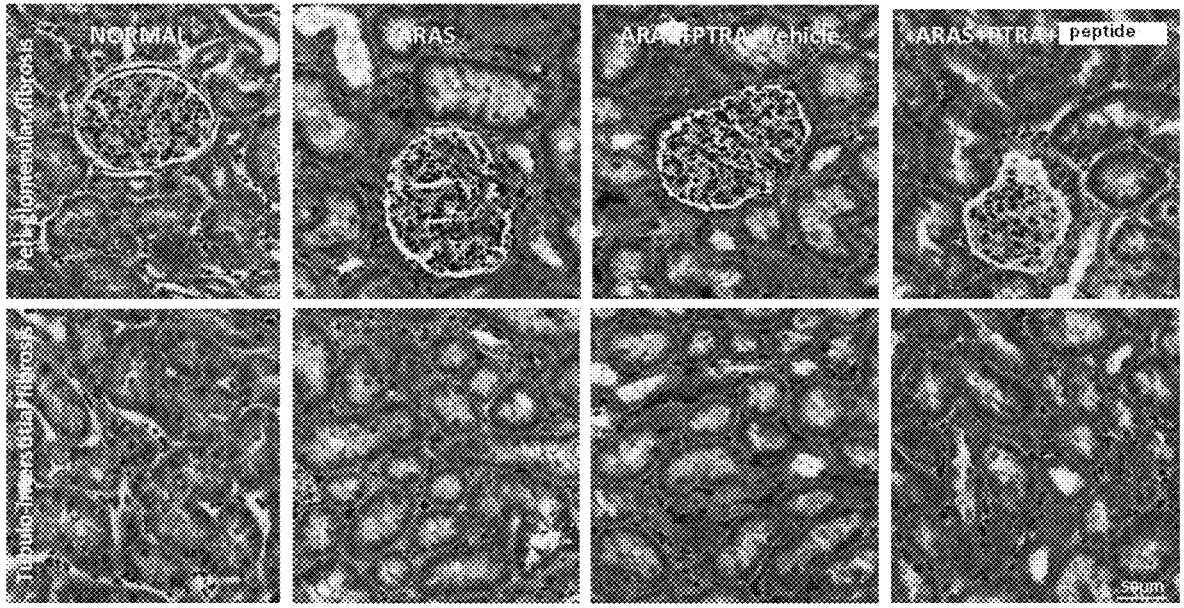
FIG. 9A shows representative trichrome staining in peri-glomerular (upper panels) and tubulo-interstitial (lower panels) renal tissue from normal, ARAS, ARAS+PTRA+vehicle, and ARAS+PTRA+D-Arg-2',6'-Dmt-Lys-Phe-NH$_2$ peptide subjects.
Figure 9B:
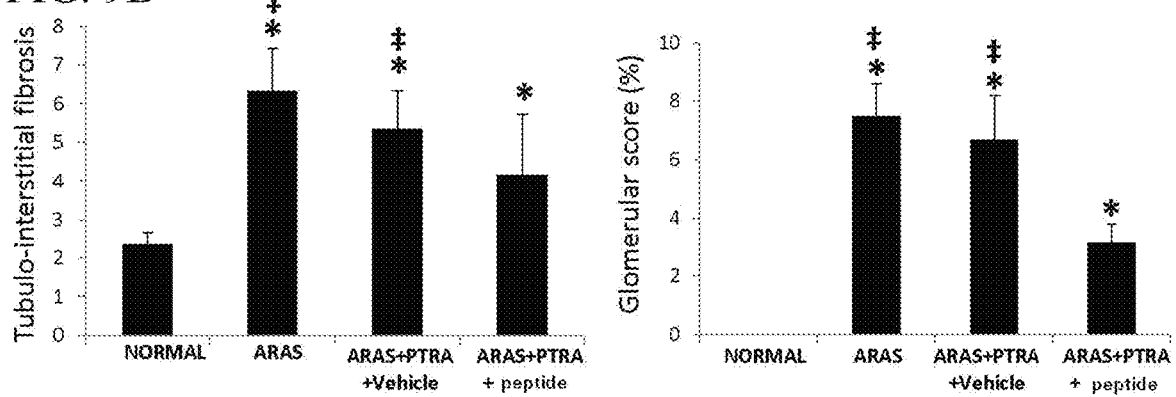
FIG. 9B shows the quantification of tubulo-interstitial fibrosis and glomerular score in normal, ARAS, ARAS+PTRA+vehicle, and ARAS+PTRA+D-Arg-2',6'-Dmt-Lys-Phe-NH$_2$ peptide subjects. Panel 9C shows a western blot of PAI-1 and TGFβ-1 protein from renal tissue of normal, ARAS, ARAS+PTRA+vehicle, and ARAS+PTRA+D-Arg-2',6'-Dmt-Lys-Phe-NH$_2$ peptide subjects and the quantification of PAI-1 and TGFβ-1 levels relative to GAPDH. *$p<0.05$ vs. Normal; ‡$p<0.05$ vs. ARAS+PTRA+D-Arg-2',6'-Dmt-Lys-Phe-NH$_2$ peptide.
Figure 9C:
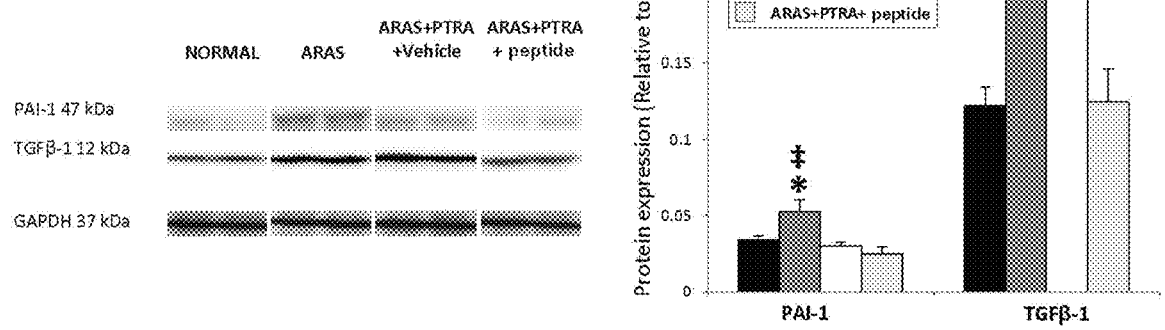

Immunostaining of the pro-fibrotic markers fibronectin and collagen IV was increased in ARAS and ARAS+PTRA+Vehicle, but reduced in peptide-treated subjects (FIG. 8B-C). Tubulo-interstitial fibrosis and glomerular score were also higher in all ARAS compared to normal, but significantly reduced in ARAS+PTRA+peptide subjects (FIG. 9A-B). Renal expression of plasminogen activator inhibitor (PAI)-1 was similarly attenuated in both PTRA groups (both $p>0.05$ vs. normal), but TGF-β1 expression was restored to normal levels only in peptide-treated subjects (FIG. 9C).

E. Discussion

The present study demonstrates the involvement of mPTP opening in attenuated renal response to revascularization in atherosclerotic renovascular disease. Furthermore, it establishes a novel role for mitochondrial-targeted peptides for preserving renal structural and functional outcomes after revascularization of an obstructive renal artery lesion in porcine ARAS. Four weeks after revascularization, mitochondrial biogenesis was upregulated in ARAS+PTRA+peptide subjects, while oxidative stress, cellular apoptosis, microvascular rarefaction, and tissue injury were ameliorated in their post-stenotic kidneys. Furthermore, stenotic-kidney perfusion, RBF, and GFR were normalized in peptide-treated subjects, revealing a renoprotective effect of peptide in conjunction to PTRA for improving renal functional outcomes in atherosclerotic renovascular disease. As such, D-Arg-2',6'-Dmt-Lys-Phe-NH$_2$ is useful in methods to upregulate mitochondrial biogenesis, decrease oxidative stress, cellular apotosis, microvasculare rarefaction and tissue injury in subjects with post-stenotic kidneys. Further, aromatic-cationic peptide D-Arg-2',6'-Dmt-Lys-Phe-NH$_2$ is useful in methods to provide a renoprotective effect in conjunction to PTRA for improving renal functional outcomes in atherosclerotic renovascular disease.

ARAS activates several mechanisms that increase oxidative damage, apoptosis, inflammation, and interstitial fibrosis, leading to renal functional deterioration, and revascularization of the obstructed renal artery has emerged as a potentially definitive therapeutic option. Alas, large randomized controlled clinical trials comparing stenting plus medical therapy with medical therapy alone showed dissociation between improvement in renal artery patency and renal outcomes after revascularization. It has been previously shown that PTRA failed to reverse structural and functional deterioration in the stenotic porcine kidney, which was accompanied by persistent apoptosis and oxidative stress, underscoring the need for more effective strategies in combination with PTRA to improve renal function in ARAS.

One of the mechanisms that perpetuate renal tissue damage during PTRA is acute IRI, which involves production of ROS and activation of inflammatory mechanisms. Furthermore, experimental and clinical data support the role of mPTP formation in accelerating cell-death following IRI. Excessive production of ROS leads to mPTP opening and release of cytochrome c into the cytosol, which triggers not only apoptosis (by activating caspase 3 and 9), but also tubular damage secondary to the release of mitochondrial ROS into the cytosol. Hence, therapeutic interventions that selectively target the mPTP might confer cytoprotection and mitigate the progression to renal failure.

Previous studies in several animal models have documented a protective effect of mitochondrial targeted peptides by inhibiting apoptosis and attenuating oxidative stress. In addition to anti-apoptotic effects (achieved by the inhibition of the opening of the mPTP), their ability to scavenge ROS and concentrate at the inner mitochondrial membrane (a major site for ROS production), provide these small peptides with extraordinary potency to inhibit oxidative stress compared to other anti-oxidant therapies. Indeed, treatment with cyclosporine (a potent inhibitor of mPTP) immediately before revascularization is associated with smaller infarct size in patients with acute myocardial infarction, underscoring the clinical importance of these therapeutic interventions. However, its therapeutic potential is limited by considerable side effects.

D-Arg-2',6'-Dmt-Lys-Phe-NH$_2$ is a cell-permeable tetrapeptide that reaches extremely high concentrations (500-5000-fold) in the inner mitochondrial membrane, exerting both antiapoptotic and antioxidant properties. Unlike other mPTP inhibitors, peptide of the present technology has no known immunosuppressive effects. Recent studies in experimental rodent models have shown beneficial effects of peptide of the present technology in reducing infarct size and attenuating hypertensive cardiomyopathy. Moreover, it prevented interstitial fibrosis and accelerated tubular cell regeneration in rat models of acute ischemia reperfusion injury and unilateral ureteral obstruction, suggesting a potential for this drug to preserve the function and structure of the injured kidney. This study shows for the first time that treatment with D-Arg-2',6'-Dmt-Lys-Phe-NH$_2$ during PTRA restores mitochondrial biogenesis and attenuates apoptosis and oxidative stress, ultimately leading to improved renal function in chronic porcine ARAS.

The potent antiapoptotic effect of D-Arg-2',6'-Dmt-Lys-Phe-NH$_2$ was reflected in this study by reduced number of TUNEL+ and caspase-3+ cells. Furthermore, renal expression of the pro-apoptic protein Bax was substantially decreased in peptide-treated subjects, underlying the effectiveness of therapies oriented to prevent the initiation of apoptosis. Additionally, treatment with PTRA+D-Arg-2',6'-Dmt-Lys-Phe-NH$_2$ reduced systemic levels of the oxidative stress markers 8-isoprostanes as well as renal oxidative stress, as evidenced by decreased ROS production and expression of NAD(P)H-oxidase (p47phox) and nitrotyrosine.

This reduction in systemic and renal oxidative stress after D-Arg-2',6'-Dmt-Lys-Phe-NH$_2$ treatment likely contributed to the preservation of the microvascular network in the stenotic kidney. Augmented or prolonged production of ROS compromises the integrity of the renal microvessels, leading to remodeling or rarefaction, an important determinant of the progression of renal injury and responses to revascularization. In the current study, microvascular loss was blunted in ARAS+PTRA+D-Arg-2',6'-Dmt-Lys-Phe-NH$_2$ subjects, as reflected in the increased spatial density and decreased average diameter of cortical microvessels, while tortuosity, reflecting microvascular immaturity, decreased. Not wishing to be bound by theory, D-Arg-2',6'-Dmt-Lys-Phe-NH$_2$ might have also prevented microvascular loss by blunting vascular cell apoptosis and promoting angiogenesis, suggested by increased renal expression of the angiogenic factor VEGF and its receptors.

Renal inflammation is a critical determinant of disease progression in ARAS. It has been previously shown that increased oxidative stress is associated with infiltration of macrophages and lymphocytes in the stenotic porcine kidney, which was associated with poor renal responses to revascularization and attenuated by chronic antioxidant supplementation. Notably, short-term treatment with D-Arg-2',6'-Dmt-Lys-Phe-NH$_2$ during PTRA abolished renal inflammation 4 weeks later, as evidenced by normalized tubulo-interstitial expression of MCP-1, which may have accounted for reduced infiltration of CD163 macrophages in the stenotic kidney. Its potent anti-inflammatory effect was also supported by normalized renal expression of the pro-inflammatory cytokine TNF-α. Importantly, decreased inflammation, oxidative stress, and apoptosis after treatment with D-Arg-2',6'-Dmt-Lys-Phe-NH$_2$ might have all attenuated tubular damage, reflected by reduced tubular injury score. In accordance, D-Arg-2',6'-Dmt-Lys-Phe-NH$_2$ attenuated acute ischemia-induced tubular damage in rats by preserving tubular brush borders and minimizing tubular cell detachment.

Mitochondrial biogenesis was promoted in animals treated with peptide, disclosed by the restored levels of PGC-1α, NFR-1, GABP, and PPAR-α, implicating activation of this pathway in the amelioration of oxidative stress and inflammation. PGC-1α-mediated activation of NRF-1 and GABP (also known as NRF-2) regulate the expression of a number of genes involved in oxidative stress by binding the human antioxidant response element (hARE), which regulates the expression of detoxifying enzymes such as NAD(P)H:quinone oxidoreductase (NQO1). Furthermore, peptide-induced mitochondrial biogenesis upregulated the expression of PPAR-α, a transcription factor highly expressed in the kidney that regulates macrophage and endothelial cell inflammatory responses by augmenting HO-1 enzymatic activity, although HO-1 expression remained suppressed in the D-Arg-2',6'-Dmt-Lys-Phe-NH$_2$-treated group. Similarly, renal expression of PPAR-δ and SIRT-1 remained downregulated in peptide-treated subjects, which argues against their protective contribution to the D-Arg-2',6'-Dmt-Lys-Phe-NH$_2$-induced attenuated inflammation following PTRA. Taken together, these observations show that adjunctive infusion of D-Arg-2',6'-Dmt-Lys-Phe-NH$_2$ during PTRA might have prevented acute fall in mitochondrial biogenesis which might have accounted for the improved renal function and structure sustained 4 weeks later.

Treatment with PTRA+D-Arg-2',6'-Dmt-Lys-Phe-NH$_2$ decreased tubulo-interstitial and glomerular fibrosis 4 weeks later, which was associated with decreased fibronectin and collagen IV content. Furthermore, renal expression of the fibrogenic factors TGF-β and PAI-1 were normalized in peptide-treated animals, possibly facilitated by decreased renal oxidative stress levels. In turn, these might have contributed to improved renal hemodynamics and function in peptide-treated subjects, evidenced by normalized single-kidney prefusion, RBF, and GFR, underscoring the feasibility of peptide to attenuate renal dysfunction in ARAS. However, these effects are unlikely due to direct regulation of vascular tone, given the lack of renal vascular reactivity response to peptide in-vitro. Despite improvement in stenotic-kidney GFR, serum creatinine levels remained slightly elevated, possibly due to some residual or hypertensive damage in the non-stenotic kidney or kidney dysfunction related to hypercholesterolemia, which may warrant more targeted treatments to lingering dislipemia.

There were no detectable acute changes in inflammatory or oxidative mediators within a 3-hour time frame after PTRA, with the exception of an increase in MCP-1, which was unaffected by D-Arg-2',6'-Dmt-Lys-Phe-NH$_2$. Exposure to D-Arg-2',6'-Dmt-Lys-Phe-NH$_2$ during PTRA was sufficient to confer potent protective effects that were sustained 4 weeks later.

This porcine model of ARAS reproduces the effects of early atherosclerosis and allows studying single-kidney function and structure using clinically-applicable tooks, offering the opportunity to assess the potential effects of peptide for improving renal function, reducing apoptosis and the progression to fibrosis in the ARAS kidney.

Collectively, these results underscore the importance of mPTP opening in revascularization of atherosclerotic renovascular disease, revealing a renoprotective effect of D-Arg-2',6'-Dmt-Lys-Phe-NH$_2$ in conjunction with PTRA for decreasing apoptosis, inflammation, and oxidative stress in porcine ARAS. Moreover, treatment with PTRA+D-Arg-2',6'-Dmt-Lys-Phe-NH$_2$ upregulated mitochondrial biogenesis and improved angiogenesis, and ultimately improved renal hemodynamics and function after revascularization in ARAS. These results uncovered a unique role for D-Arg-2',6'-Dmt-Lys-Phe-NH$_2$ in improving responses after PTRA in chronic renovascular disease.

TABLE 9

Systemic characteristics (mean ± SD) of normal, ARAS, ARAS + PTRA + Vehicle, and ARAS + PTRA + D-Arg-2',6'-Dmt-Lys-Phe-NH$_2$ subjects (n = 7 each) four weeks after PTRA or sham.

| | NORMAL | ARAS | ARAS + PTRA + Vehicle | ARAS + PTRA + D-Arg-2',6'-Dmt-Lys-Phe-NH$_2$ |
|---|---|---|---|---|
| Body weight (Kg) | 46.1 ± 2.1 | 44.7 ± 1.8 | 43.0 ± 1.3 | 46.7 ± 2.2 |
| Degree of stenosis (%) | 0 | 88.7 ± 3.9*‡ | 0 | 0 |
| Mean arterial pressure (mmHg) | 85.9 ± 2.8 | 166.6 ± 2.4* | 90.6 ± 2.8 | 106.8 ± 2.9 |
| Serum creatinine (mg/dl) | 1.45 ± 1.52 | 1.96 ± 0.30* | 1.91 ± 0.43* | 1.98 ± 0.36* |
| PRA (ng/ml/hr) | 0.12 ± 0.05 | 0.16 ± 0.13 | 0.15 ± 0.09 | 0.14 ± 0.11 |
| Total cholesterol (mg/dl) | 92.2 ± 17.9 | 498.9 ± 61.3* | 383.7 ± 80.6* | 469.8 ± 97.0* |
| Triglycerides (mg/dl) | 7.8 ± 2.2 | 9.6 ± 8.5 | 4.6 ± 3.0 | 5.8 ± 2.8 |
| HDL (mg/dl) | 42.8 ± 14.1 | 182.6 ± 55.2* | 192.3 ± 54.0* | 188.6 ± 47.1* |
| LDL cholesterol (mg/dl) | 47.8 ± 9.5 | 314.0 ± 77.5* | 241.4 ± 70.1* | 247.8 ± 142.4* |
| 8-epi-isoprostane (pg/ml) | 94.3 ± 12.5 | 133.2 ± 11.2*‡ | 136.9 ± 13.3*‡ | 118.2 ± 13.9 |
| Urinary albumin (μg/ml) | 4.0 ± 2.6 | 3.8 ± 1.1 | 3.3 ± 3.0 | 3.8 ± 3.3 |

ARAS: Atherosclerotic renal artery stenosis, PTRA: percutaneous transluminal renal angioplasty; PRA: plasma renin activity; HDL: high-density lipoproteins; LDL: low-density lipoproteins.
*p ≤ 0.05 vs. Normal;
‡p < 0.05 vs. ARAS + PTRA + peptide.

These results demonstrate that the peptide D-Arg-2',6'-Dmt-Lys-Phe-NH$_2$ of the present technology is useful in methods for treatment and prevention of renal injury associated with revascularization by PTRA in subjects with RAS. In particular, these results demonstrate that administration of the D-Arg-2',6'-Dmt-Lys-Phe-NH$_2$ protects renal microvasculature against reperfusion-related injury, leading to improved renal function compared to untreated controls, and an improved prognosis for subjects treated for RAS.

Example 2 Reduction of Renal Injury Following Percutaneous Transluminal Renal Angioplasty (ARAS) in Human Atherosclerotic Renal Artery Stenosis (ARAS) by Administration of D-Arg-2',6'-Dmt-Lys-Phe-NH$_2$ A. Summary This example will demonstrate use of the aromatic-cationic peptide D-Arg-2',6'-Dmt-Lys-Phe-NH$_2$ in the prevention and treatment of renal injury associated with renal atherosclerotic artery stenosis (ARAS) in humans. According to the present methods, human subjects with ARAS undergo renal revascularization by percutaneous transluminal renal angioplasty (PTRA). Subjects are administered aromatic-cationic peptide in conjunction with PTRA, including defined time periods before and after the revascularization procedure. Control subjects receive either no infusion, or infusion of control vehicle alone. Multiple aspects of renal function are predicted to improve in subjects receiving the peptide as compared to control subjects, including renal volume, renal blood flow, glomerular filtration rate, renal microvasculature density, average vessel diameter, vessel tortuosity, and renal oxygenation. The results will demonstrate that the peptide D-Arg-2',6'-Dmt-Lys-Phe-NH$_2$ is useful in methods for treating or preventing renal injury associated with revascularization by PTRA in the treatment of ARAS in humans.

B. Overview of Experimental Design

Human subjects with ARAS are randomized into experimental and control groups. Subjects are treated by PTRA with stenting, with adjunct continuous infusion of aromatic-cationic peptide D-Arg-2',6'-Dmt-Lys-Phe-NH$_2$ (0.05 mg/kg IV) from a time point 30 minutes prior to PTRA to 3 hours after PTRA. Briefly, a balloon catheter wrapped by a tantalum stent is engaged in the proximal-middle section of the renal artery under fluoroscopic guidance and inflated, resulting in expansion to full balloon diameter, to restore the luminal opening. The balloon is deflated and removed, leaving the stent embedded in the vascular wall. Experimental subjects are treated with a single continuous intravenous infusion of D-Arg-2',6'-Dmt-Lys-Phe-NH$_2$ 0.50 mg/kg from 30 min before to 3:30 hrs after PTRA. Control subjects receive either no infusion ("non-infusion control") or are infused with saline vehicle only ("vehicle control"). Four weeks after PTRA the degree of stenosis is determined by angiography, and both systemic and renal venous blood samples are collected for plasma renin activity and creatinine measurements. (GammaCoat PRA kit; DiaSorin, Inc., Stillwater, Minn., USA). Renal hemodynamics and function in each kidney are assessed using MDCT and renal oxygenation is assessed by BOLD MRI.

C. Methods

Blood oxygen level-dependent magnetic resonance imaging (BOLD-MM)—Four weeks after PTRA, BOLD-MM is performed at 3 Tesla (Signa Echo Speed; GE Medical Systems, Milwaukee, Wis.) to measure R2* levels in medullary and cortical regions of the kidney using customized abdominal organ protocols. The principle of the BOLD method has been described in detail in previous publications. Briefly, paramagnetic molecules induce magnetic field perturbations. In the blood, oxyhemoglobin is diamagnetic and its concentration has no effect on T2*, but Deoxyhemoglobin is paramagnetic and decreases tissue T2*. Therefore, when the echo time of the gradient echo MRI acquisition increases, the MRI signal attenuation increases with increased concentration of deoxyhemoglobin. The slope of Ln (intensity) vs. echo time equals relaxation time rate R2* (=1/T2) and is directly proportional to the concentration of deoxyhemoglobin. Following the baseline BOLD acquisition, furosemide (20 mg) is administered intravenously and flushed with 2 ml of saline. The BOLD measurements are repeated 15 min later. For data analysis, regions of interest are manually traced in the cortex and medulla on the 7-ms echo time image that gives the best anatomic details in each experimental period. For each echo time, the software automatically computes the average of MR signals within each region of interest. The BOLD signal, as characterized by the relaxivity R2*, is then measured. The change in R2* from baseline to furosemide is determined as "delta-R2*."

Multidetector Computer Tomography (MDCT)—One to two days after BOLD MRI, renal hemodynamics and function in each kidney is assessed using MDCT. MDCT is an ultra-fast scanner that provides accurate and noninvasive quantifications of single kidney volume, regional perfusion, blood flow, glomerular filtration rate (GFR), and tubular function. Briefly, images are obtained after 45 consecutive scans post central venous injection of iopamidol (0.5 mL/kg per 2 seconds). MDCT images are reconstructed and displayed with the Analyze software package (Biomedical Imaging Resource, Mayo Clinic, MN, USA). Regions of interest are selected from cross-sectional images from the aorta, renal cortex, and medulla. Average tissue attenuation in each region is plotted over time and fitted by curve-fitting algorithms to obtain measures of renal function. Cortical and medullary volumes are calculated by Analyze (Biomedical Imaging Resource, Mayo Clinic, MN, USA) and RBF as the sum of the products of cortical and medullary perfusions and corresponding volumes. GFR is calculated from the cortical curve using the slope of the proximal tubular curve. The same procedure is repeated after 15 min toward the end of a 10 min suprarenal infusion of acetylcholine (Ach) (5 µg/kg/min) to test endothelium-dependent microvascular reactivity. A tracker catheter (Prowler Microcatheter, Cordis, Miami, Fla., USA) introduced from the carotid artery is placed above the renal arteries for infusion of Ach. Hemodynamics and function are therefore measured over a stable 3-min observation period at baseline and during Ach infusion.

Plasma Nitrate/Nitrite Levels—Plasma nitrate/nitrite levels are quantified by a two-step assay using a commercially available kit (Nitric Oxide Quantitation Kit, Active Motif, Carlsbad, Calif.) following the manufacturer's instructions.

Pharmacokinetic Analysis

Blood Sample Collection and Handling

1. Control blood sample collection for bioanalytical assay development: 20 mL venous whole blood samples are collected. Venous blood is drawn using syringes into BD Vacutainer® PST™ Plasma Separation Tubes (lavender top) containing K2EDTA, 10 mL/tube. Tubes are gently inverted 8 times and kept in an ice water bath until centrifugation. Within an hour after the blood sample collection, samples are centrifuged in a swing bucket centrifuge at 1000-1300 RCF (or approximately 1500×G) for 15 min at 4° C. Plasma is harvested from individual blood tubes, placed in a single polypropylene vials (or screw-cap tubes), and stored at −70° C.

2. Blood sample collection for PK and biomarker analysis: Venous whole blood samples are collected for PK analysis as well as for biomarker analysis and other inflammatory biomarkers at the time points specified below.

(i) PK analysis: 4 mL venous whole blood is collected using syringes into the pre-chilled BD Vacutainer® PST™ Plasma Separation Tubes (lavender top) containing $K_2EDTA$ at the following time points: immediately before D-Arg-2',6'-Dmt-Lys-Phe-$NH_2$ infusion, immediately before PTRA, and 30, 60 and 180 min post-reperfusion. The PK blood tubes are gently mixed and placed immediately into ice (ice bath or crushed ice). Within 30 minutes of collection, samples are centrifuged at 1500×G for 15 min at 4° C., following which two plasma aliquots (approximately 0.5 mL each) are removed and immediately placed into screw-cap polypropylene tubes. Individual plasma samples are quick frozen over dry ice, and stored at −70° C.±15° C. until analysis.

(ii) Biomarker analysis: 4 mL venous whole blood is collected into the BD Vacutainer® SST™ Serum Separation Tubes at the following time points: immediately before D-Arg-2',6'-Dmt-Lys-Phe-$NH_2$ infusion, immediately before PTRA, and 30, 60 and 180 min post-reperfusion. Tubes are inverted at least 5 times after the filling. Tubes are kept at room temperature approximately one hour to allow the blood to clot, and centrifuged to collect serum samples. If no serum is produced, the following baseline reference is used: After the clotting, centrifugation in a swing bucket is performed at 1000-1300 RCF for 10 min, or 15 minutes in a fixed-angle rotor, at room temperature. Serum is collected into 5 polypropylene tubes, each containing approximately 0.5 mL serum, and stored at −70° C.

Urine Sample Collection and Handling

1. Control urine sample collection for bioanalytical assay development: 10 mL control urine samples are collected from each subject. Samples are centrifuged at approximately 1500×G for 10 minutes to remove any debris. Samples are placed in polypropylene vials and stored at −70° C.

2. Urine sample collection for D-Arg-2',6'-Dmt-Lys-Phe-$NH_2$ measurement: At the end of D-Arg-2',6'-Dmt-Lys-Phe-$NH_2$ infusion (210 min), the urinary bladder is emptied into a pre-weighed container. The combined weight of the sample and container is measured and recorded. After thorough mixing, two 10-mL aliquots are dispensed into labelled screw-cap polypropylene tubes. Individual urine samples are quick frozen over dry ice and stored at −70° C.±15° C. until testing.

Statistical Methods

Results are expressed as mean±SEM. Comparisons within groups are performed using the paired Student t-test and among groups using ANOVA, followed by the Tukey test. Statistical significance for all tests is accepted for p≤0.05.

D. Results

It is expected that following PTRA, all subjects will show a drop on mean arterial pressure to a level comparable to that of normal controls (p>0.05). It is further expected that subjects receiving an infusion of D-Arg-2',6'-Dmt-Lys-Phe-$NH_2$ in conjunction with PTRA will show an improved renal volume, renal blood flow, glomerular filtration rate, renal microvasculature density, average vessel diameter, vessel tortuosity, and renal oxygenation, compared to control subjects.

E. Conclusions

These results will demonstrate that the peptide D-Arg-2', 6'-Dmt-Lys-Phe-$NH_2$ of the present technology is useful in methods for treatment and prevention of renal injury associated with revascularization by PTRA in human subjects with RAS. In particular, these results will demonstrate that administration of the peptide protects renal microvasculature against reperfusion-related injury, leading to improved renal function compared to control subjects, and an improved prognosis for subjects treated for RAS.

Example 3: Reduction of Kidney Deterioration in Porcine Atherosclerotic Renal Artery Stenosis (ARAS) by Administration of D-Arg-2',6'-Dmt-Lys-Phe-$NH_2$ A. Summary This example will demonstrate that administration of D-Arg-2',6'-Dmt-Lys-Phe-$NH_2$ attenuates renal cell apoptosis and inflammation, oxidative stress, fibrosis, and kidney functional-structural deterioration in ARAS subjects untreated with vascular intervention. The results of this example are particularly relevant for ARAS subjects who are not candidates for PTRA.

B. Overview of Experimental Design

Figure 17:
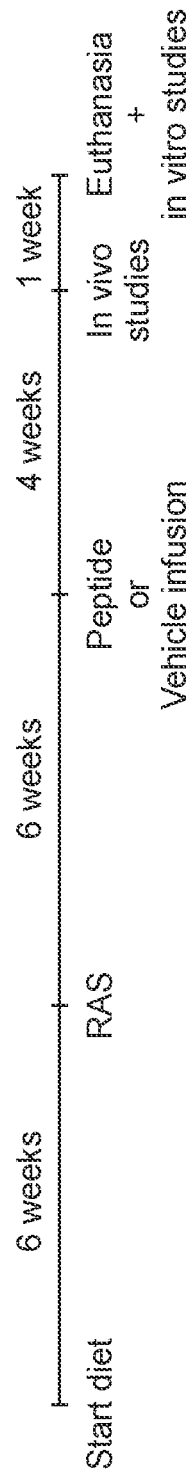
FIG. 17 is a schematic providing an overview of the experimental design (interventions and time points) of Example 3.

Two groups of pigs will be studied in vivo after 10 weeks of ARAS and 4 weeks of chronic subcutaneous (SC) infusion of D-Arg-2',6'-Dmt-Lys-Phe-NH$_2$ or saline vehicle (FIG. 17, Table 10). Single-kidney volume, perfusion, renal blood flow, glomerular filtration rate, and oxygenation will be studied in subjects either untreated or treated with D-Arg-2',6'-Dmt-Lys-Phe-NH$_2$ using multi-detector computer tomography and blood oxygen level-dependent magnetic resonance. Blood pressure will be followed daily using an implantable telemetry transmitter. Effects of D-Arg-2',6'-Dmt-Lys-Phe-NH$_2$ on renal inflammation, apoptosis fibrosis, angiogenesis, and oxidative stress will be assessed using standard in vitro protocols. Effects of D-Arg-2',6'-Dmt-Lys-Phe-NH$_2$ on renal microvascular architecture will be studied ex vivo using micro-computed tomography.

Fourteen pigs (50-60 kg) will be studied during 16 weeks of observation (FIG. 17) after approval by the Institution Animal care and Use Committee (IACUC). At baseline, all subjects will start a high-cholesterol diet consisting of 2% cholesterol and 15% lard in order to simulate the clinical situation in which diffuse early atherosclerosis precedes the stenosis (Table 10). Six weeks later, ARAS subjects will be anesthetized with 0.5 g of intramuscular ketamine and xylazine, and anesthesia then maintained with intravenous ketamine (0.2 mg/kg/min) and xylazine (0.03 mg/kg/min). RAS will be induced by placing a local-irritant coil in the main renal artery which leads to a gradual development of unilateral RAS, as described in Chade et al., FASEB J 2006; 20: 1706-1708.

TABLE 10

Overview of Experimental Design

| Group | N | Treatment |
|---|---|---|
| ARAS + saline | 7 | High cholesterol diet + RAS + sham + saline |
| ARAS + D-Arg-2',6'-Dmt-Lys-Phe-NH$_2$ | 7 | High cholesterol diet + RAS + sham + D-Arg-2',6'-Dmt-Lys-Phe-NH$_2$ |

After induction of RAS (or sham), a telemetry system will be implanted in the left femoral artery to measure MAP and the animals will be followed for 10 additional weeks. The average MAP in the last two weeks before each study will be calculated. Six weeks after induction of RAS, animals will be similarly anesthetized and the degree of stenosis will be determined by angiography. A sham procedure will be performed in all subjects, which involves cannulating the renal artery and selective renal angiography with contrast injections. In addition, 7 ARAS subjects will start treatment with chronic SC infusion of D-Arg-2',6'-Dmt-Lys-Phe-NH$_2$ 0.1 mg/kg in mL saline once daily 5 days per week. A saline vehicle will be administered in the other 7 ARAS subjects (Table 10).

Four weeks later, the subjects will be again similarly anesthetized. The degree of stenosis will be determined by angiography, and both systemic and renal venous blood samples will be collected for plasma renin activity (GammaCoat PRA kit; DiaSorin, Inc., Stillwater, Minn., USA) and creatinine measurements. Renal hemodynamics and function in each kidney will be assessed using multidetector computer tomography (MDCT), and renal oxygenation by blood oxygen level-dependent magnetic resonance imaging (BOLD MRI) (Table 11).

After completion of all studies, subjects will be euthanized with a lethal intravenous dose of 100 mg/kg of sodium pentobarbital (Sleepaway, Fort Dodge Laboratories, Inc., Fort Dodge, Iowa, USA). The kidneys will be removed using a retroperitoneal incision and immediately dissected, and sections will be frozen in liquid nitrogen (and maintained at −80° C.) or preserved in formalin for in vitro studies (Table 11).

C. Methods

Blood oxygen level-dependent magnetic resonance imaging (BOLD-MRI)—Four weeks after infusion, BOLD-MRI will be performed at 3 Tesla (Signa Echo Speed; GE Medical Systems, Milwaukee, Wis., USA) to measure R2* levels in medullary and cortical regions of the kidney using customized abdominal organ protocols, as previously described. MRI examinations will be performed during suspended respiration. The principle of the BOLD method has been described in detail in previous publications. Briefly, paramagnetic molecules induce magnetic field perturbations. In the blood, oxyhemoglobin is diamagnetic and its concentration has no effect on T2*, but Deoxyhemoglobin is paramagnetic and decreases tissue T2*. Therefore, when the echo time of the gradient echo MRI acquisition increases, the MRI signal attenuation increases with increased concentration of deoxyhemoglobin. The slope of Ln (intensity) vs. echo time equals relaxation time rate R2* (=1/T2) and is directly proportional to the concentration of deoxyhemoglobin. Following the baseline BOLD acquisition, furosemide (20 mg) will be administered intravenously into an ear vein catheter and flushed with 2 ml of saline. The BOLD measurements will be repeated 15 min later. For data analysis, regions of interest will be manually traced in the cortex and medulla on the 7-ms echo time image that gives the best anatomic details in each experimental period. For each echo time, the software automatically computed the average of MR signals within each region of interest. The BOLD signal, as characterized by the relaxivity R2*, will then be measured. Finally, the change in R2* from baseline to furosemide will be determined as "delta-R2*."

Multidetector Computer Tomography (MDCT)—One-Two days after BOLD MRI, renal hemodynamics and function in each kidney will be assessed using MDCT. MDCT is an ultra-fast scanner that provides accurate and noninvasive quantifications of single kidney volume, regional perfusion, RBF, GFR, and tubular function. Briefly, images will be obtained after 160 consecutive scans post central venous injection of iopamidol (0.5 mL/kg per 2 seconds). MDCT images will be reconstructed and displayed with the Analyze software package (Biomedical Imaging Resource, Mayo Clinic, MN, USA). Regions of interest will be selected from cross-sectional images from the aorta, renal cortex, and medulla. Average tissue attenuation in each region will be plotted over time and fitted by curve-fitting algorithms to obtain measures of renal function. Cortical and medullary volumes will be calculated by Analyze and RBF as the sum of the products of cortical and medullary perfusions and corresponding volumes. GFR will be calculated from the cortical curve using the slope of the proximal tubular curve. The same procedure will be repeated after 15 min toward the end of a 10 min suprarenal infusion of acetylcholine (Ach) (5 µg/kg/min) to test endothelium-dependent microvascular reactivity. A tracker catheter (Prowler Microcatheter, Cordis, Miami, Fla., USA) introduced from the carotid artery will be placed above the renal arteries for infusion of Ach. Hemodynamics and function will be therefore measured over a stable 3-min observation period at baseline and during acetylcholine (Ach) infusion.

Histology—Midhilar 5-nm cross-sections of each kidney (one per animal) will be examined using a computer-aided image analysis program (MetaMorph, Meta Imaging, Molecular Devices, Sunnyvale, Calif., USA). In each slide, trichrome staining or DHE fluorescence will be semiautomatically quantified in 15-20 fields by the computer program, expressed as fraction of kidney surface area, and the results from all fields will be averaged.

Apoptosis—Apoptosis will be evaluated by the terminal deoxynucleotidyl transferase-mediated dUTP nick end end-labeling (TUNEL) assay, activated caspase-3 staining, and measurement of the levels of the pro-apoptotic Bax and anti-apoptotic Bcl-xL proteins.

Oxidative stress—In-vitro studies will be performed to assess oxidative stress in the kidney. Systemic levels of the oxidative stress biomarkers isoprostanes will be assessed using an EIA kit, as previously described. Renal redox status will be evaluated by assessing the in-situ production of superoxide anion, detected by fluorescence microscopy using dihydroethidium (DHE), as described previously, and by the expression of the radical forming enzyme nicotinamide adenine dinucleotide phosphate hydrogen (NAD(P)H)-oxidase and endothelial nitric oxide synthase (eNOS).

Plasma nitrate/nitrite levels—Plasma nitrate/nitrite levels will be quantified by a two-step assay for the sum of both using a commercially available kit (Nitric Oxide Quantitation Kit, Active Motif, Carlsbad, Calif., USA) following the manufacturer's instructions.

Western Blotting—Western Blotting protocols will be followed using specific polyclonal antibodies against: MMP-9, PAI-1, monocyte chemoattractant protein-1 (MCP-1), VEGF, VEGF receptor-1 (VEGFR1), tumor necrosis factor alpha (TNF-α), and transforming growth factor beta (TGF-β). Protein expression will be determined in each kidney, and the intensities of the protein bands (one per animal) will be quantified.

Micro-computed Tomography Analysis (MCT)—After flushing the kidney, microfil MV122 (an intravascular contrast agent) will be perfused into the stenotic kidney under physiological pressure through a cannula ligated in a branch of the renal artery. Samples will be prepared and scanned, and images analyzed as previously described. The spatial density and average diameter of microvessels (diameters in the range of 20-500 mm) in the inner, middle, and outer thirds of the renal cortex will be also calculated using the software package ANALYZE™.

TABLE 11

In vivo and In vitro Studies

| Parameter | Meaning of Results |
| --- | --- |
| Multidetector Computer Tomography (MDCT) | Renal hemodynamics and function |
| Blood oxygen level-dependent magnetic resonance imaging (BOLD-MRI) | Renal oxygenation |
| Micro-computed Tomography Analysis (MCT) | Microvascular rarefaction |
| TUNEL, activated caspase-3 staining, and protein expression of Bcl-xL and Bax | Apoptosis |
| H&E and Trichrome staining, macrophage CD163, MCP-1, MMP-9, PAI-1, MCP-1, VEGF, TNF-α, TGF-β, and VEGFR1 | Renal morphology, inflammation, and fibrosis |
| Isoprostanes, superoxide production, expression of NAD(P)H oxidase, DHE, NO synthase expression, plasma nitrate/nitrite levels | Oxidative stress |

Statistical methods—Based on preliminary data, power calculations indicate that 6 animals (plus 1 to account for animal loss) per group will be required to detect differences with power of 80%. Results will be expressed as mean±SEM. Comparisons within groups will be performed using the paired Student t test and among groups using ANOVA, followed by the Tukey test. Statistical significance for all tests will be accepted for $p \leq 0.05$.

D. Results

It is expected that administration of D-Arg-2',6'-Dmt-Lys-Phe-NH$_2$ to untreated ARAS subjects will decrease apoptosis, as indicated by a reduction in the levels of Bax, an increase in the levels of Bcl-xL, and a decrease in the number of TUNEL+ cells. It is further expected that administration of D-Arg-2',6'-Dmt-Lys-Phe-NH$_2$ will cause a decrease in renal renal vascular, tubular, and glomerular fibrosis, as indicated by a decrease in the degree of fibrosis trichrome staining and the expression of fibrogenic factors TGF-β and PAI-1. It is further expected that administration of D-Arg-2',6'-Dmt-Lys-Phe-NH$_2$ will decrease renal inflammation as indicated by a decrease in TNF-α, CD163, and MCP-1 levels. It is further expected that administration of D-Arg-2',6'-Dmt-Lys-Phe-NH$_2$ will decrease oxidative stress, as indicated by a reduction in the in situ production of superoxide and NAD(P)H oxidase expression accompanied by increased NO availability (eNOS expression, nitrate/nitrite levels). In addition, it is expected that administration of D-Arg-2',6'-Dmt-Lys-Phe-NH$_2$ will prevent the loss of renal microvasculature, as detected by micro-CT, leading to an increase in microvascular density, renal hemodynamic and oxygenation.

E. Conclusions

This example will demonstrate that the aromatic-cationic peptide D-Arg-2',6'-Dmt-Lys-Phe-NH$_2$ is useful in methods and compositions for the treatment of ARAS in subjects untreated by vascular intervention, such as those who are not candidates for PTRA.

Example 4 Chronic Treatment with D-Arg-2',6'-Dmt-Lys-Phe-NH$_2$ Preserves the Stenotic Kidney in Swine ARVD Summary This example demonstrates use of the aromatic-cationic peptide D-Arg-2',6'-Dmt-Lys-Phe-NH$_2$ in the preservation of the stenotic kidney in swine ARVD. According to the present methods, animal subjects were subjected to a period of ARAS. Subjects were administered aromatic-cationic peptide daily for the last four weeks of the ten week period. Control animals received either no infusion, or infusion of control vehicle alone. Multiple aspects of renal function were improved in subjects receiving the peptide as compared to control subjects, including but not limited to single kidney volume, perfusion, renal blood flow (RBF), glomerular filtration rate (GFR), cortical oxygenation, and renal fibrosis. The results demonstrate that the peptide D-Arg-2', 6'-Dmt-Lys-Phe-NH$_2$ is useful in methods for chronic treatment of ARVD.

Experimental Design

All experiments were performed in accordance with guidelines and approved by the Institutional Animal Care and Use Committee (IACUC). Subjects comprised domestic juvenile female subjects (Manthei Hog Farm, LLC, MN) during 10 weeks of observation. At baseline, animals were randomized in either normal or ARAS groups. Normal animals were fed normal pig chow, and ARAS subjects a high-cholesterol diet (TD-93296, Harlan-Teklad, Indianapolis, Ind., USA), which induces diffuse early-atherosclerosis, characterized by elevated cholesterol levels and renal functional compromise, inflammation and fibrosis in the RAS kidney. See Table 12.

After a period of six weeks, ARAS subjects underwent unilateral RAS, induced by placing a local-irritant coil in the main renal artery, while normal animals were sham-operated. For anesthesia, animals were induced with an intramuscular injection of ketamine and xylazine (0.5 g), and anesthesia was maintained with intravenous ketamine (0.2 mg/kg/min) and xylazine (0.03 mg/kg/min). A telemetry system (Data Sciences International, St Paul, Minn., USA) was implanted in the left femoral artery to continuously measure mean arterial pressure (MAP) for the 10 following weeks.

Ten weeks after induction of RAS, subjects received subcutaneous injections of 0.1 mg/kg D-Arg-2',6'-Dmt-Lys-Phe-NH$_2$ or vehicle 5 days of each week for a period of four weeks.

Following four weeks of treatment with D-Arg-2',6'-Dmt-Lys-Phe-NH$_2$ or vehicle, the subjects were similarly anesthetized and the degree of stenosis determined by angiography. Multi-detector computer tomography (MDCT) studies were performed for assessment of single-kidney renal hemodynamics and function. Following a central venous injection of iopamidol (0.5 mL/kg per 2 seconds), 140 consecutive scans were performed. Cross-sectional images were reconstructed, and analyzed with the Analyze™ software package (Biomedical Imaging Resource, Mayo Clinic, Rochester, Minn.). Regions of interest were selected from cross-sectional images of the renal cortex and medulla. Average tissue attenuation in each region was plotted over time and fitted by curve-fitting algorithms to obtain measures of renal function. Cortical and medullary volumes were calculated by Analyze and RBF as the sum of the products of cortical and medullary perfusions and corresponding volumes. GFR was calculated from the cortical curve using the slope of the proximal tubular curve. The same procedure was repeated after 15 min toward the end of a 10 min suprarenal infusion of Ach (5 µg/kg/min) to test endothelium-dependent microvascular reactivity. A tracker catheter (Prowler Microcatheter, Cordis, Miami, Fla., USA) introduced from the carotid artery was placed above the renal arteries for infusion of Ach. Hemodynamics and function was measured over a stable 3-min observation period at baseline and during Ach infusion. Renal oxygenation was assessed using blood oxygen level-dependent (BOLD) MRI.

TABLE 12

Overview of Experimental Design

| Group | Treatment |
| --- | --- |
| Normal + Vehicle | Normal diet + saline vehicle |
| Normal + Peptide | Normal diet + D-Arg-2',6'-Dmt-Lys-Phe-NH$_2$ |
| ARVD + vehicle | High cholesterol diet + RAS + saline |
| ARVD + peptide | High cholesterol diet + RAS + D-Arg-2',6'-Dmt-Lys-Phe-NH$_2$ |

After the completion of in vivo studies, animals were euthanized with sodium pentobarbital (100 mg/kg, Sleepaway®, Fort Dodge Laboratories, Fort Dodge, Iowa, USA). The kidneys were removed, dissected, and prepared for ex vivo studies.

Renal fibrosis was assessed in 5 µm mid-hilar cross-sections of each kidney stained with Masson's trichrome by using the computer-aided image-analysis program AxioVision® 4.8.2.0 (Carl ZEISS SMT, Oberkochen, Germany). Tubulo-interstitial fibrosis and glomerular score (% of sclerotic out of 100 glomeruli) were quantified in 15-20 fields.

All data were analyzed using JMP software package version 8.0 (SAS Institute Inc., Cary, N.C., USA). The Shapiro-Wilk test was used to test for deviation from normality. Results were expressed as mean±standard deviation (SD) for normally distributed data, and medium (range) for non-normally distributed data. Parametric (ANOVA and unpaired Student t-test) and non-parametric (Wilcoxon and Kruskal Wallis) tests were used as appropriate. Values of $p \leq 0.05$ were considered statistically significant.

Results

Six weeks after the induction of RAS, significant degrees of stenosis was achieved in all ARAS animals (81.0-89.8%), and mean arterial pressure (MAP) was similarly elevated (p<0.05 vs. normal) (Table 13).

Figure 10:
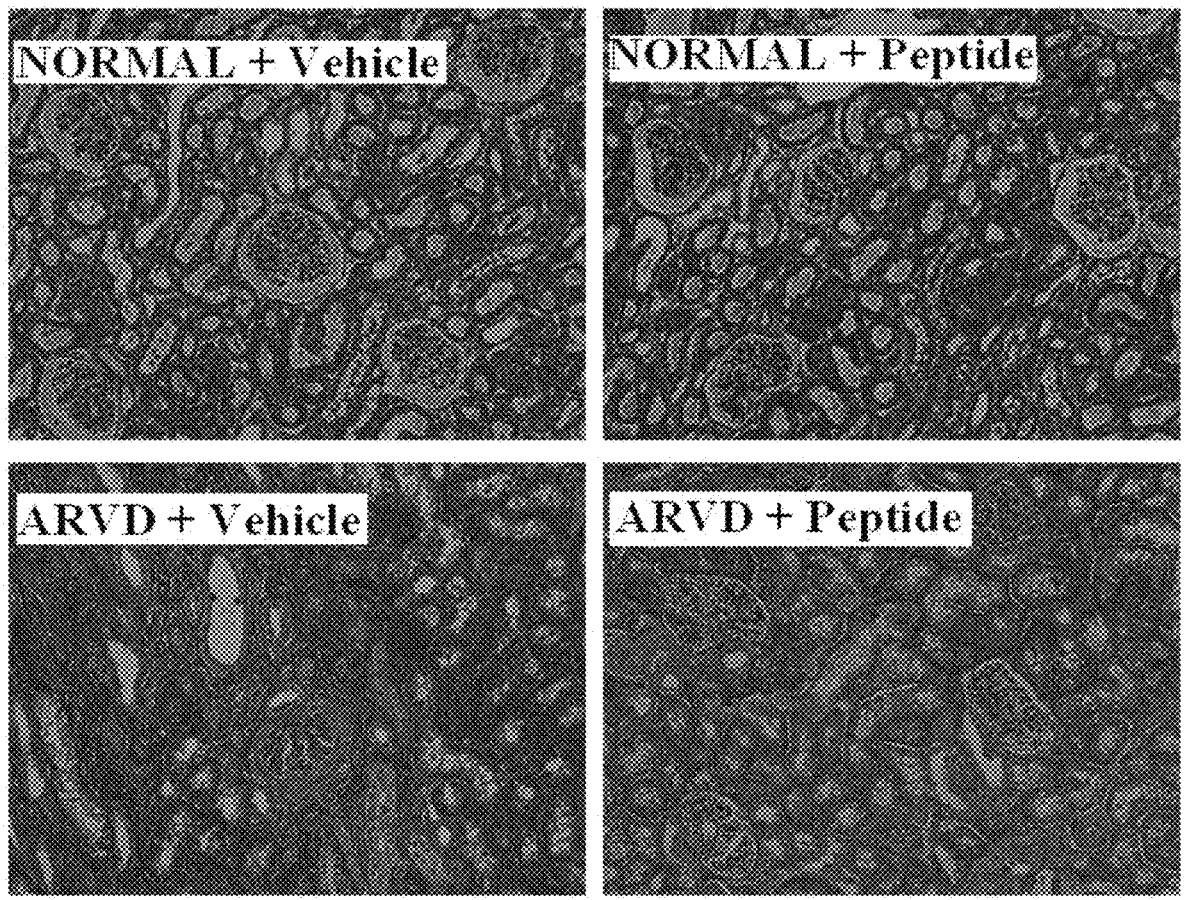
FIG. 10 shows representative trichrome staining (blue; 40× mag.) of renal tissue sections from Normal+vehicle, Normal+peptide, ARVD+vehicle, and ARVD+peptide subjects.
Figure 11:
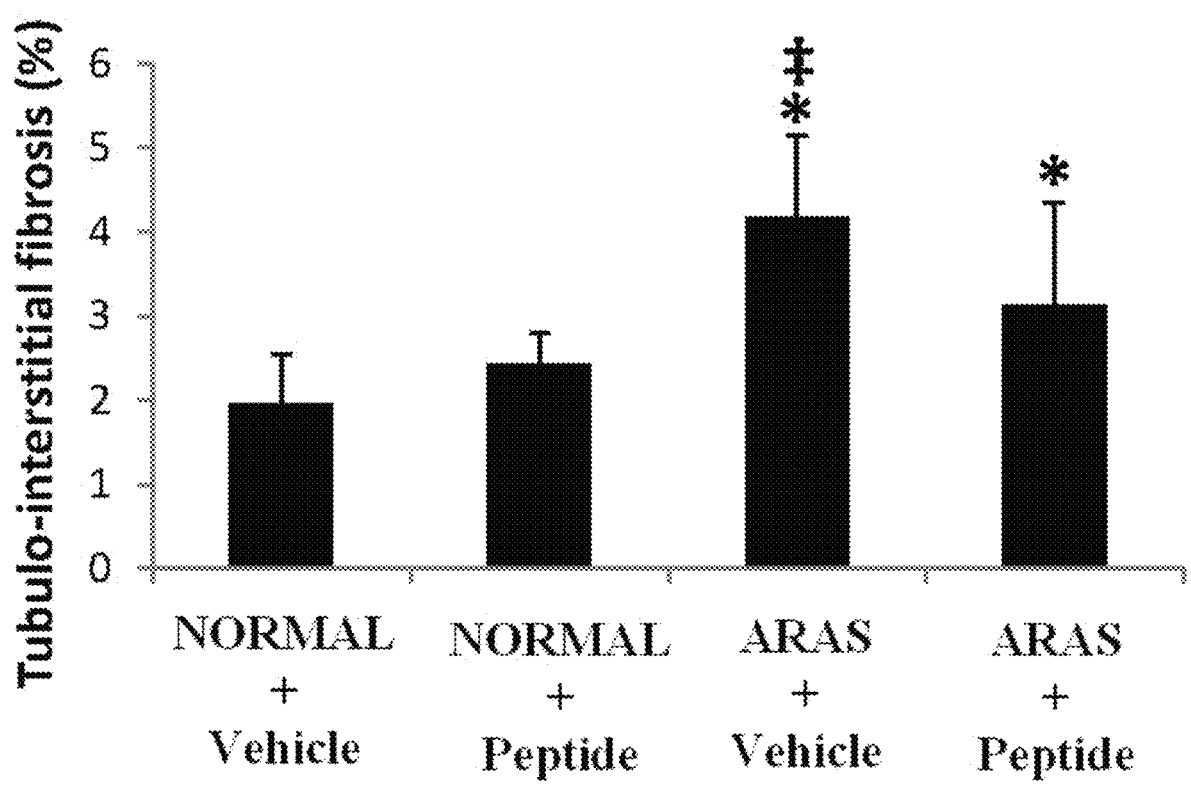
FIG. 11 shows the quantification of trichrome staining in Normal+vehicle, Normal+peptide, ARAS+vehicle, and ARAS+peptide subjects depicted in FIG. 10. *$p<0.05$ vs. Normal; ‡$p<0.05$ vs. ARVD+peptide.
Figure 12:
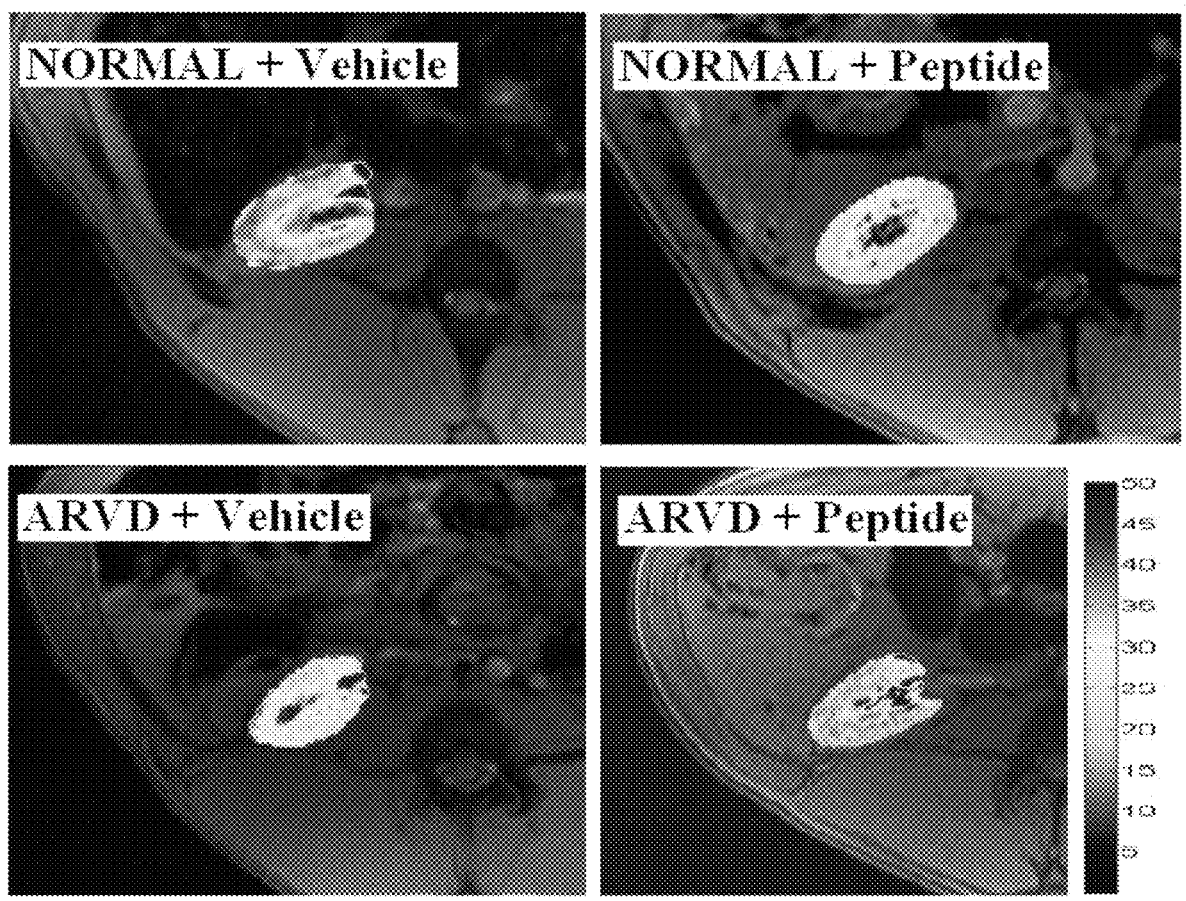
FIG. 12 shows representative BOLD MRI images for Normal+vehicle, Normal+peptide, ARAS+vehicle, and ARAS+peptide subjects.
Figure 13:
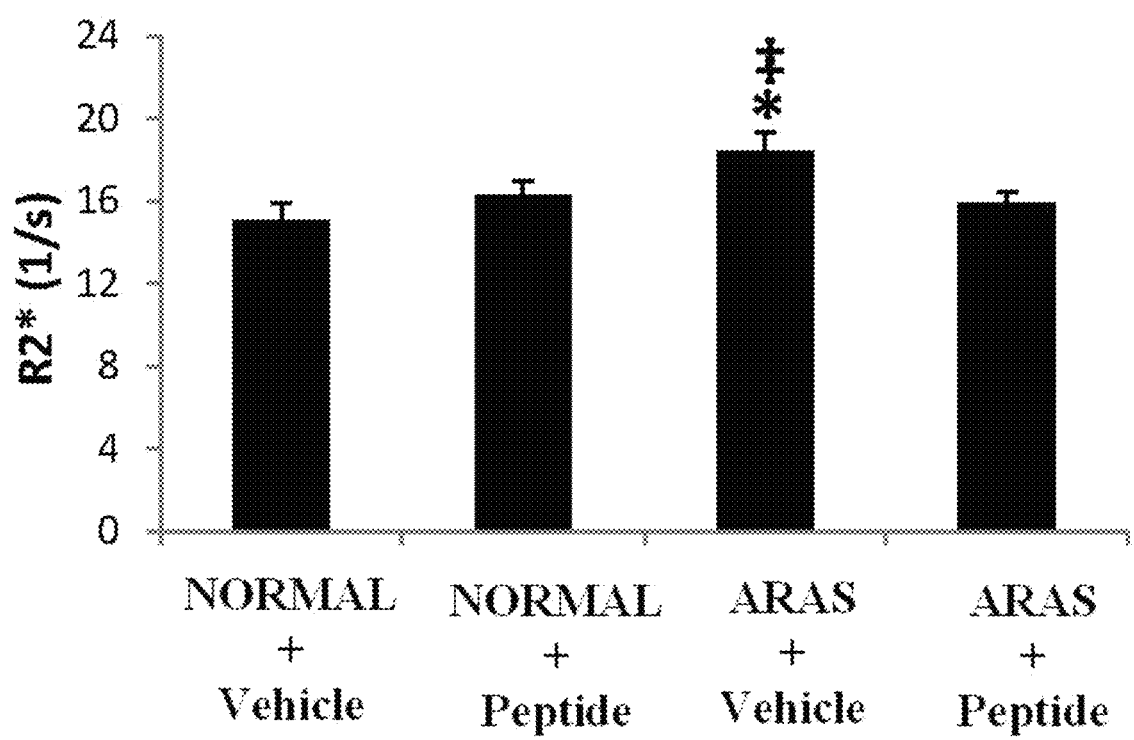
FIG. 13 shows quantification of cortical blood oxygenation index (R2*) in Normal+vehicle, Normal+peptide, ARAS+vehicle, and ARAS+peptide subjects as depicted in FIG. 10. *$p<0.05$ vs. Normal; ‡$p<0.05$ vs. ARVD+peptide.
Figure 14:
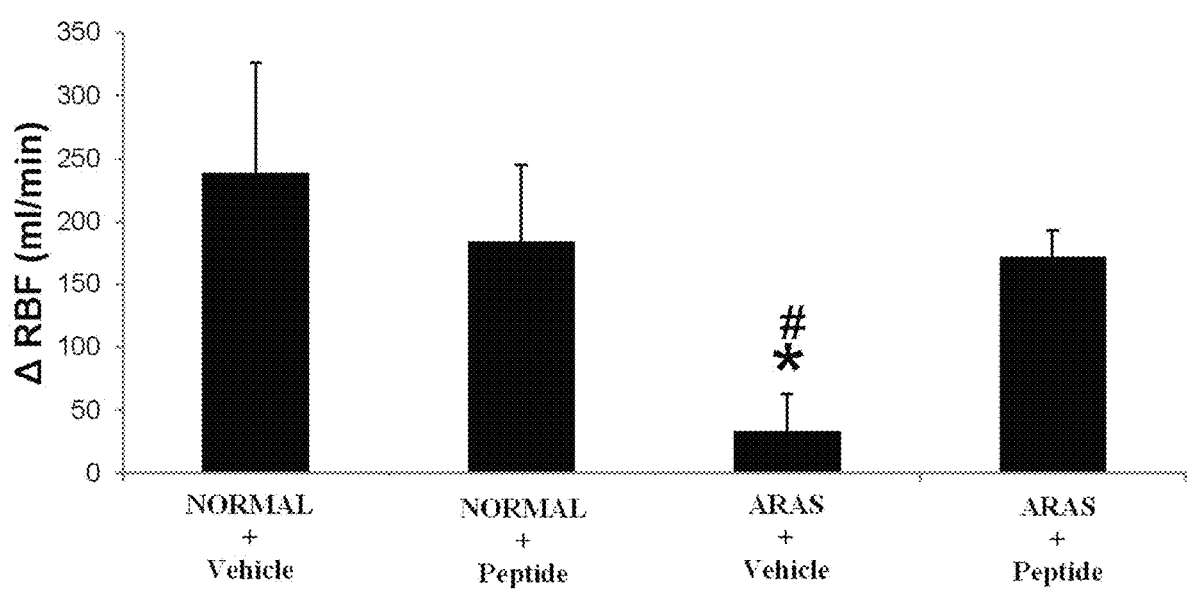
FIG. 14 shows magnitude of change in renal blood flow (ΔRBF) in Normal+peptide, ARAS+vehicle, and ARAS+peptide subjects in response to Ach infusion. *$p<0.05$ vs. Normal; #$p<0.05$ vs. ARVD+peptide.
Figure 15:
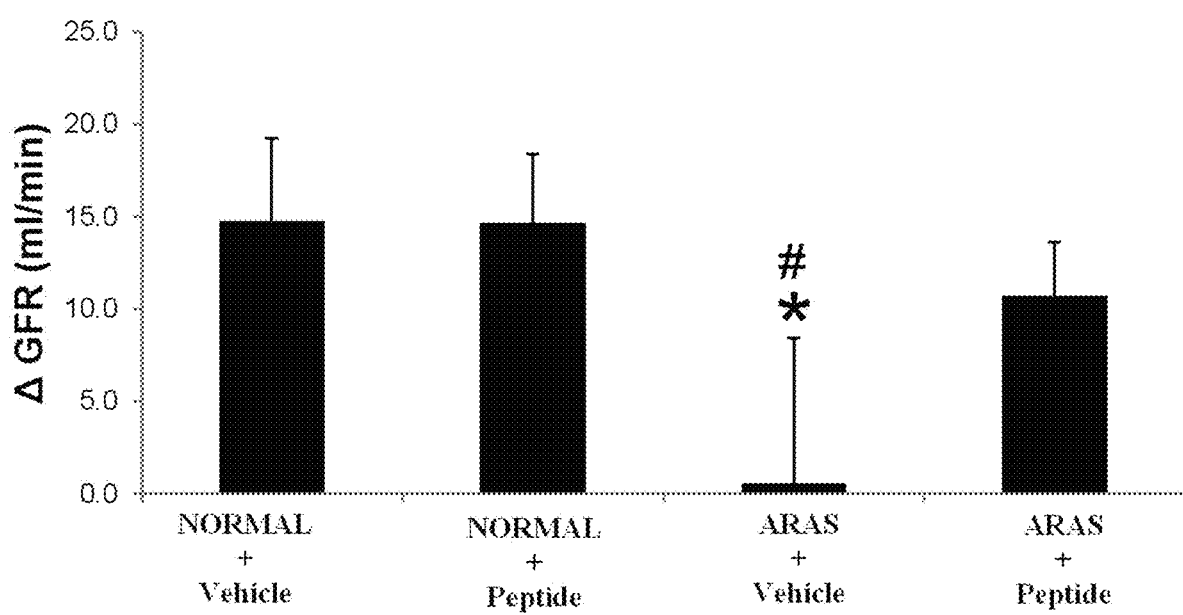
FIG. 15 shows magnitude of change in glomerular filtration rate (ΔGFR) in Normal+peptide, ARAS+vehicle, and ARAS+peptide subjects in response to Ach infusion. *p<0.05 vs. Normal; #p<0.05 vs. ARVD+peptide.
Figure 16A:
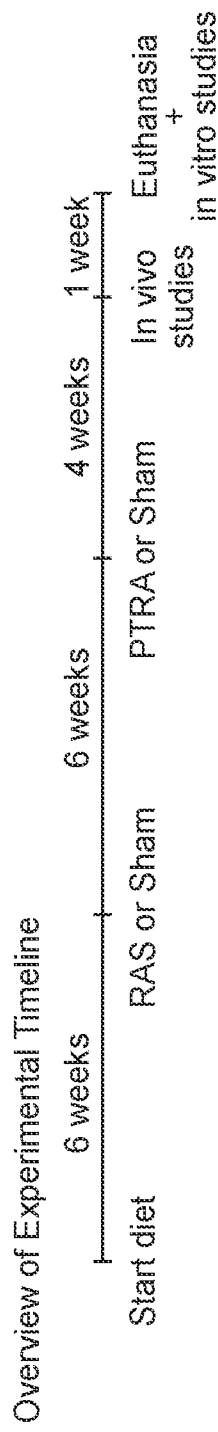
FIGS. 16A-16D are schematics providing a summary of the experimental design (interventions and time points) of Example 1.
Figure 16B:
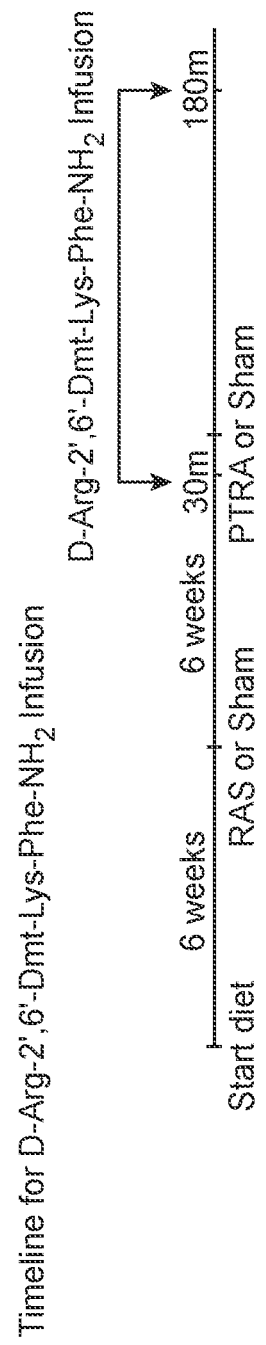
Figure 16C:
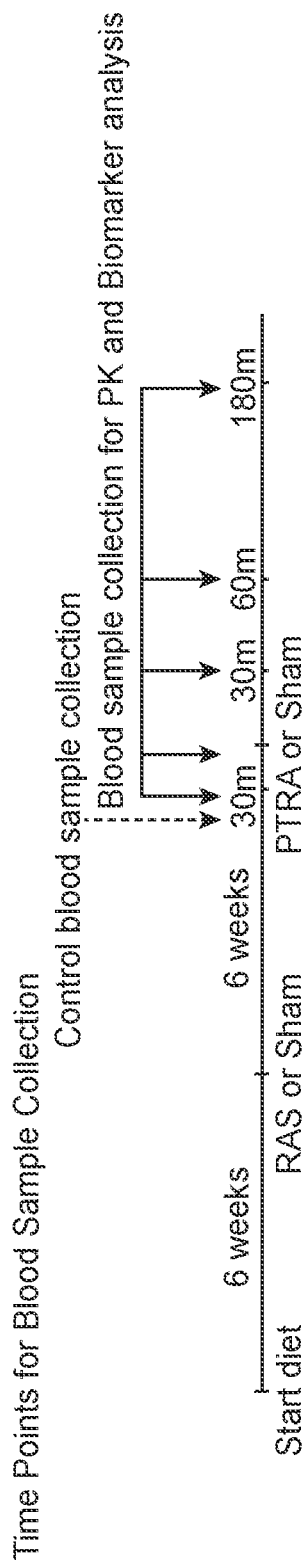
Figure 16D:
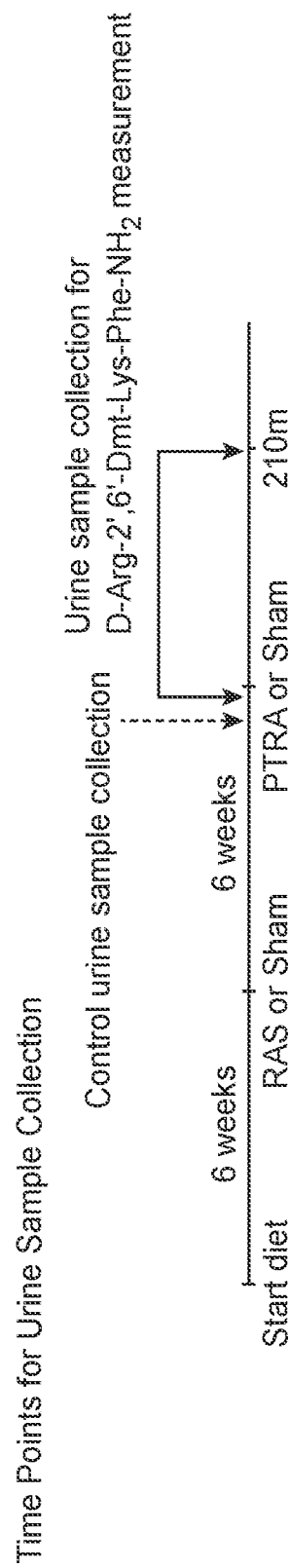

Table 13 shows mean arterial pressure (mmHg), renal volume (cc), cortical perfusion (ml/min/cc), RBF (ml/min), GFR (ml/min), and tubulointerstitial fibrosis (%) in normal and ARAS subjects following treatment with D-Arg-2',6'-Dmt-Lys-Phe-NH$_2$ or vehicle during the last four weeks of a ten week period of ARAS. Trichrome staining of renal tissue sections is shown in FIG. 10 and quantified in FIG. 11. Blood oxygen level-dependent (BOLD) MRI images are shown in FIG. 12, with quantification of cortical blood oxygenation index (R2*) shown in FIG. 13.

Four weeks following induction of ARAS, renal hemodynamic parameters were reduced in ARAS subjects compared to normal controls (Table 13). Likewise, ARAS subjects showed increased tubulointerstitial fibrosis and reduced cortical blood oxygenation compared to normal controls (Table 13; FIGS. 10-13). Vascular reactivity was reduced in ARAS subjects as measured by the magnitude change in RBF and GFR in response to Ach.

Treatment with D-Arg-2',6'-Dmt-Lys-Phe-NH$_2$ reduced tubulointerstitial fibrosis and increased renal volume, cortical perfusion, RBF, and GFR in ARAS subjects compared to untreated controls. (Table 13; FIGS. 10-11). Treatment with D-Arg-2',6'-Dmt-Lys-Phe-NH$_2$ also improved cortical blood oxygenation and vascular reactivity to Ach compared to untreated controls (FIG. 12-15).

TABLE 13

Renal Stenosis, Hemodynamics, and Function In Normal and ARAS Subjects

|  | NORMAL + Vehicle | NORMAL + Bendavia | ARVD + Vehicle | ARVD + Bendavia |
| --- | --- | --- | --- | --- |
| Degree of stenosis (%) | 0 | 0 | 89.8 ± 5.2* | 81.0 ± 5.3* |
| Mean blood pressure (mmHg) | 82.2 ± 41.6 | 84.4 ± 23.7 | 173.4 ± 19.4* | 171.5 ± 15.8* |
| Renal Volume (cc) | 102.9 ± 4.0 | 96.1 ± 6.3 | 66.4 ± 6.3*‡ | 104.9 ± 3.3 |

TABLE 13-continued

Renal Stenosis, Hemodynamics, and Function In Normal and ARAS Subjects

|  | NORMAL + Vehicle | NORMAL + Bendavia | ARVD + Vehicle | ARVD + Bendavia |
| --- | --- | --- | --- | --- |
| Cortical Perfusion (ml/min/cc) | 4.5 ± 0.5 | 4.0 ± 0.3 | 3.1 ± 0.2*‡ | 4.4 ± 0.2 |
| RBF (ml/min) | 553.8 ± 82.8 | 589.7 ± 71.8 | 318.8 ± 61.0*‡ | 535.1 ± 24.9 |
| GFR (ml/min) | 84.0 ± 3.8 | 75.8 ± 6.8 | 48.0 ± 4.0*‡ | 86.6 ± 11.2 |
| Tubulointerstitial fibrosis (%) | 1.9 ± 0.6 | 2.4 ± 0.4 | 4.2 ± 0.9*‡ | 2.8 ± 1.0 |

*p < 0.05 vs. Normal
‡p < 0.05 vs. ARVD + peptide

*p<0.05 vs. Normal
‡p<0.05 vs. ARVD+peptide

These results demonstrate that the D-Arg-2',6'-Dmt-Lys-Phe-$NH_2$ peptide of the present technology is useful in the treatment of subjects with ARAS. In particular, the results show that chronic treatment of ARAS subjects with the D-Arg-2',6'-Dmt-Lys-Phe-$NH_2$ peptide reduces renal tubulointerstitial fibrosis and improves renal hemodynamics and vascular reactivity. The results further show that the D-Arg-2',6'-Dmt-Lys-Phe-$NH_2$ peptide is useful for improving kidney function generally in a subject with ARVD, and improving the subject's prognosis.

Example 5 Improved Renal Function Following Chronic Treatment with D-Arg-2',6'-Dmt-Lys-Phe-$NH_2$ in Human Subjects with ARVD Summary This example will demonstrate use of the aromatic-cationic peptide D-Arg-2',6'-Dmt-Lys-Phe-$NH_2$ in the chronic treatment of human subjects with ARVD.

According to the present methods, human subjects with ARVD are administered D-Arg-2',6'-Dmt-Lys-Phe-$NH_2$ peptide daily for a period of several weeks. Control subjects receive either no infusion, or infusion of control vehicle alone. Multiple aspects of renal function are predicted to improve in subjects receiving the peptide as compared to control subjects, including renal volume, cortical perfusion, RBF, GFR, cortical blood oxygenation, and vascular reactivity. The results will demonstrate that the D-Arg-2',6'-Dmt-Lys-Phe-$NH_2$ peptide is useful in methods for chronic treatment of human subjects with ARVD.

Experimental Design

Human subjects with ARVD are randomized into experimental and control groups. Subjects are treated with D-Arg-2',6'-Dmt-Lys-Phe-$NH_2$ (0.1 mg/kg) peptide or vehicle administered subcutaneously once daily for a period of four weeks. Renal hemodynamics and function in each kidney are assessed using MDCT and renal oxygenation is assessed by BOLD MRI.

Blood oxygen level-dependent magnetic resonance imaging (BOLD-MRI)—Four weeks after PTRA, BOLD-MRI is performed at 3 Tesla (Signa Echo Speed; GE Medical Systems, Milwaukee, Wis.) to measure R2* levels in medullary and cortical regions of the kidney using customized abdominal organ protocols, as previously described. Briefly, paramagnetic molecules induce magnetic field perturbations. In the blood, oxyhemoglobin is diamagnetic and its concentration has no effect on T2*, but Deoxyhemoglobin is paramagnetic and decreases tissue T2*. Therefore, when the echo time of the gradient echo MRI acquisition increases, the MRI signal attenuation increases with increased concentration of deoxyhemoglobin. The slope of Ln (intensity) vs. echo time equals relaxation time rate R2* (=1/T2) and is directly proportional to the concentration of deoxyhemoglobin. Following the baseline BOLD acquisition, furosemide (20 mg) is administered intravenously and flushed with 2 ml of saline. The BOLD measurements are repeated 15 min later. For data analysis, regions of interest are manually traced in the cortex and medulla on the 7-ms echo time image that gives the best anatomic details in each experimental period. For each echo time, the software automatically computes the average of MR signals within each region of interest. The BOLD signal, as characterized by the relaxivity R2*, is then measured. The change in R2* from baseline to furosemide is determined as "delta-R2*."

Multidetector Computer Tomography (MDCT)—One to two days after BOLD MRI, renal hemodynamics and function in each kidney is assessed using MDCT. MDCT is an ultra-fast scanner that provides accurate and noninvasive quantifications of single kidney volume, regional perfusion, blood flow, glomerular filtration rate (GFR), and tubular function. Briefly, images are obtained after 45 consecutive scans post central venous injection of iopamidol (0.5 mL/kg per 2 seconds). MDCT images are reconstructed and displayed with the Analyze software package (Biomedical Imaging Resource, Mayo Clinic, MN, USA). Regions of interest are selected from cross-sectional images from the aorta, renal cortex, and medulla. Average tissue attenuation in each region is plotted over time and fitted by curve-fitting algorithms to obtain measures of renal function. Cortical and medullary volumes are calculated by Analyze (Biomedical Imaging Resource, Mayo Clinic, MN, USA) and RBF as the sum of the products of cortical and medullary perfusions and corresponding volumes. GFR is calculated from the cortical curve using the slope of the proximal tubular curve. The same procedure is repeated after 15 min toward the end of a 10 min suprarenal infusion of acetylcholine (Ach) (5 µg/kg/min) to test endothelium-dependent microvascular reactivity. A tracker catheter (Prowler Microcatheter, Cordis, Miami, Fla., USA) introduced from the carotid artery is placed above the renal arteries for infusion of Ach. Hemodynamics and function are therefore measured over a stable 3-min observation period at baseline and during Ach infusion.

Results are expressed as mean±SEM. Comparisons within groups are performed using the paired Student t-test and among groups using ANOVA, followed by the Tukey test. Statistical significance for all tests is accepted for p≤0.05.

Results

It is expected that following chronic treatment with the peptide D-Arg-2',6'-Dmt-Lys-Phe-$NH_2$ of the present technology, ARVD subjects will show improved renal volume, cortical perfusion, RBF, GFR, cortical blood oxygenation, and vascular reactivity, and reduced mean arterial blood pressure compared to untreated control subjects. It is further expected that treated subjects will show reduced tubulointerstitial fibrosis compared to untreated control subjects. It is expected that values for the aforementioned parameters will be comparable to normal controls. (p<0.05).

These results will demonstrate that the D-Arg-2',6'-Dmt-Lys-Phe-NH$_2$ peptide of the present technology is useful in the treatment of human subjects with ARAS. In particular, the results will show that chronic treatment of human ARAS subjects with the D-Arg-2',6'-Dmt-Lys-Phe-NH$_2$ peptide reduces renal tubulointerstitial fibrosis and improves renal hemodynamics and vascular reactivity. The results will further show that the D-Arg-2',6'-Dmt-Lys-Phe-NH$_2$ peptide is useful for improving kidney function generally in a subject with ARVD, and improving the subject's prognosis.

REFERENCES

Bakker E N, et al., Small artery remodeling depends on tissue-type transglutaminase. Circ Res. 2005; 96:119-126.

Chade A R and Kelsen S, Renal Microvascular Disease Determines the Responses to Revascularization in Experimental Renovascular Disease, Circ Cardiovasc Interv 2010; 3(4): 376-383.

Chade A R, et al., Antioxidant intervention blunts renal injury in experimental renovascular disease, J Am Soc Nephrol 2004; 15: 958-966.

Chade A R, et al., Antioxidant intervention prevents renal neovascularization in hypercholesterolemic pigs, J Am Soc Nephrol 2004; 15: 1816-1825.

Chade A R, et al., Beneficial effects of antioxidant vitamins on the stenotic kidney. Hypertension. 2003; 42:605-612.

Chade A R, et al., Comparison of acute and chronic antioxidant interventions in experimental renovascular disease, Am J Physiol Renal Physiol 2004; 286: F1079-1086.

Chade A R, et al., Distinct renal injury in early atherosclerosis and renovascular disease, Circulation 2002; 106: 1165-1171.

Chade A R, et al., Endothelin-1 receptor blockade prevents renal injury in experimental hypercholesterolemia, Kidney Int 2003; 64: 962-969.

Chade A R, et al., Mechanisms of renal structural alterations in combined hypercholesterolemia and renal artery stenosis, Arterioscler Thromb Vasc Biol 2003; 23: 1295-1301.

Chade A R, et al., Simvastatin promotes angiogenesis and prevents microvascular remodeling in chronic renal ischemia, FASEB J 2006; 20: 1706-1708.

Cho S, et al., A novel cell-permeable antioxidant peptide, SS31, attenuates ischemic brain injury by down-regulating CD36, J Biol Chem 2007; 282: 4634-4642.

Daemen M A, et al., Inhibition of apoptosis induced by ischemia-reperfusion prevents inflammation, J Clin Invest 1999; 104: 541-549.

Dai D F, et al., Mitochondrial targeted antioxidant peptide ameliorates hypertensive cardiomyopathy. J Am Coll Cardiol. 2011.

Epstein F H and Prasad P, Effects of furosemide on medullary oxygenation in younger and older subjects, Kidney Int 2000; 57: 2080-2083.

Epstein F H, et al., Effect of diabetes on renal medullary oxygenation during water diuresis, Diabetes Care 2002; 25: 575-578.

Favreau F, et al., Revascularization of swine renal artery stenosis improves renal function but not the changes in vascular structure, Kidney Int. 2010; 78(11): 1110-1118.

Gerwins P, et al., Function of fibroblast growth factors and vascular endothelial growth factors and their receptors in angiogenesis. Crit Rev Oncol Hematol. 2000; 34:185-194.

Gloviczki M L, et al., Comparison of 1.5 and 3 T BOLD M R to study oxygenation of kidney cortex and medulla in human renovascular disease, Invest Radiol 2009; 44: 566-571.

Gloviczki M L, et al., Preserved oxygenation despite reduced blood flow in poststenotic kidneys in human atherosclerotic renal artery stenosis, Hypertension 55: 961-966.

Gomez S I, et al., Increased hypoxia and reduced renal tubular response to furosemide detected by BOLD magnetic resonance imaging in swine renovascular hypertension, Am J Physiol Renal Physiol 2009; 297: F981-986.

Hansen K J, et al., Prevalence of renovascular disease in the elderly: a population-based study, J Vasc Surg 2002; 36: 443-451.

Heil M and Schaper W. Influence of mechanical, cellular, and molecular factors on collateral artery growth (arteriogenesis). Circ Res. 2004; 95:449-458.

Hricik D E, et al., Captopril-induced functional renal insufficiency in patients with bilateral renal-artery stenoses or renal-artery stenosis in a solitary kidney. N Engl J Med.

Juillard L, et al., Blood oxygen level-dependent measurement of acute intra-renal ischemia, Kidney Int 2004; 65: 944-950.

Kalra P A, et al., Atherosclerotic renovascular disease in United States patients aged 67 years or older: risk factors, revascularization, and prognosis, Kidney Int 2005; 68: 293-301.

Langille B L and Dajnowiec D. Cross-linking vasomotor tone and vascular remodeling: A novel function for tissue transglutaminase? Circ Res. 2005; 96:9-11.

Lavi R, et al., Simvastatin decreases endothelial progenitor cell apoptosis in the kidney of hypertensive hypercholesterolemic pigs, Arterioscler Thromb Vasc Biol 30: 976-983.

Lerman L O, et al., Noninvasive evaluation of a novel swine model of renal artery stenosis, J Am Soc Nephrol 1999; 10: 1455-1465.

Mizuguchi Y, et al., A novel cell-permeable antioxidant peptide decreases renal tubular apoptosis and damage in unilateral ureteral obstruction, Am J Physiol Renal Physiol 2008; 295: F1545-1553.

Nogae S, et al., Induction of apoptosis in ischemia-reperfusion model of mouse kidney: possible involvement of Fas, J Am Soc Nephrol 1998; 9: 620-631.

Orrenius S, Reactive oxygen species in mitochondria-mediated cell death, Drug Metab Rev 2007; 39: 443-455.

Plouin P F, et al., Blood pressure outcome of angioplasty in atherosclerotic renal artery stenosis: a randomized trial, Essai Multicentrique Medicaments vs Angioplastie (EMMA) Study Group, Hypertension 1998; 31: 823-829.

Prasad P V and Epstein F H, Changes in renal medullary pO2 during water diuresis as evaluated by blood oxygenation level-dependent magnetic resonance imaging: effects of aging and cyclooxygenase inhibition, Kidney Int 1999; 55: 294-298.

Prasad P V, et al., Noninvasive evaluation of intrarenal oxygenation with BOLD MRI, Circulation 1996; 94: 3271-3275.

Rosenberger C, et al., Up-regulation of hif in experimental acute renal failure: Evidence for a protective transcriptional response to hypoxia. Kidney Int. 2005; 67:531-542.

Sachse A and Wolf G. Angiotensin ii-induced reactive oxygen species and the kidney. J Am Soc Nephrol. 2007; 18:2439-2446.

Shanley P F. The pathology of chronic renal ischemia. Semin Nephrol. 1996; 16:21-32.

Stulak J M, et al., Renal vascular function in hypercholesterolemia is preserved by chronic antioxidant supplementation. J Am Soc Nephrol. 2001; 12:1882-1891.

Szeto H H, et al., Mitochondria-targeted peptide accelerates atp recovery and reduces ischemic kidney injury. J Am Soc Nephrol. 2011; 22:1041-1052.

Szeto H H, Mitochondria-targeted cytoprotective peptides for ischemia-reperfusion injury, Antioxid Redox Signal 2008; 10: 601-619.

Textor S C and Wilcox C S, Renal artery stenosis: a common, treatable cause of renal failure?, Annu Rev Med 2001; 52: 421-442.

van Jaarsveld B C, et al., The effect of balloon angioplasty on hypertension in atherosclerotic renal-artery stenosis. Dutch Renal Artery Stenosis Intervention Cooperative Study Group, N Engl J Med 2000; 342: 1007-1014.

Vedder N B, et al., Inhibition of leukocyte adherence by anti-CD18 monoclonal antibody attenuates reperfusion injury in the rabbit ear, Proc Natl Acad Sci USA 1990; 87: 2643-2646.

Verhoeff B J et al., Influence of percutaneous coronary intervention on coronary microvascular resistance index. Circulation. 2005; 111:76-82.

Webster J, et al., Randomised comparison of percutaneous angioplasty vs continued medical therapy for hypertensive patients with atheromatous renal artery stenosis. Scottish and Newcastle Renal Artery Stenosis Collaborative Group, J Hum Hypertens 1998; 12: 329-335.

Wheatley K, et al., Revascularization versus medical therapy for renal-artery stenosis. N Engl J Med. 2009; 361:1953-1962.

Yao E H, et al., Oxidative stress on progenitor and stem cells in cardiovascular diseases. Curr Pharm Biotechnol. 2006; 7:101-108.

Zhu X Y, et al., Antioxidant intervention attenuates myocardial neovascularization in hypercholesterolemia, Circulation 2004; 109: 2109-2115.

Zhu X Y, et al., Cortical microvascular remodeling in the stenotic kidney: role of increased oxidative stress, Arterioscler Thromb Vasc Biol 2004; 24: 1854-1859.

Zhu X Y, et al., Redox-sensitive myocardial remodeling and dysfunction in swine diet-induced experimental hypercholesterolemia, Atherosclerosis 2007; 193: 62-69.

Zhu X Y, et al., Simvastatin prevents coronary microvascular remodeling in renovascular hypertensive pigs, J Am Soc Nephrol 2007; 18: 1209-1217.

Zhu, et al., The chemokine monocyte chemoattractant protein-1 contributes to renal dysfunction in swine renovascular hypertension, J Hypertens 2009; 27: 2063-2073.

What is claimed is:

1. A method for improving vascular reactivity in a subject in need thereof, the method comprising administering to the subject a therapeutically effective amount of a peptide D-Arg-2',6'-Dmt-Lys-Phe-$NH_2$ or a pharmaceutically acceptable salt thereof, wherein the subject is diagnosed with atherosclerotic renovascular disease (ARVD).

2. The method of claim 1, wherein the ARVD comprises reduced renal blood flow (RBF) as compared to a normal control subject.

3. The method of claim 1, wherein the ARVD comprises reduced glomerular filtration rate (GFR) as compared to a normal control subject.

4. The method of claim 1, further comprising the step of performing a revascularization procedure on the subject.

5. The method of claim 4, wherein the revascularization procedure comprises percutaneous transluminal renal angioplasty.

6. The method of claim 4, wherein the subject is administered the peptide prior to the revascularization procedure, after the revascularization procedure, during and after the revascularization procedure or continuously before, during, and after the revascularization procedure.

7. The method of claim 6, wherein the subject is administered the peptide for at least 3 hours after the revascularization procedure, for at least 5 hours after the revascularization procedure, for at least 8 hours after the revascularization procedure, for at least 12 hours after the revascularization procedure, or for at least 24 hours after the revascularization procedure.

8. The method of claim 6, wherein the subject is administered the peptide starting at least 8 hours before the revascularization procedure, starting at least 4 hours before the revascularization procedure, starting at least 2 hours before the revascularization procedure, starting at least 1 hour before the revascularization procedure, or starting at least 10 minutes before the revascularization procedure.

9. The method of claim 4, wherein the revascularization procedure comprises removal of a renal artery occlusion.

10. The method of claim 4, wherein the revascularization procedure comprises administration of one or more thrombolytic agents.

11. The method of claim 10, wherein the one or more thrombolytic agents are selected from the group consisting of: tissue plasminogen activator, urokinase, prourokinase, streptokinase, acylated form of plasminogen, acylated form of plasmin, and acylated streptokinase-plasminogen complex.

* * * * *